(12) United States Patent
Fredriksson et al.

(10) Patent No.: US 8,293,501 B2
(45) Date of Patent: Oct. 23, 2012

(54) METHODS AND COMPOSITIONS FOR PERFORMING LOW BACKGROUND MULTIPLEX NUCLEIC ACID AMPLIFICATION REACTIONS

(75) Inventors: Johan Erik Simon Fredriksson, Uppsala (SE); Carl Oscar Fredrik Dahl, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 654 days.

(21) Appl. No.: 12/440,716

(22) PCT Filed: Sep. 11, 2007

(86) PCT No.: PCT/US2007/019893
§ 371 (c)(1),
(2), (4) Date: Jul. 7, 2009

(87) PCT Pub. No.: WO2008/033442
PCT Pub. Date: Mar. 20, 2008

(65) Prior Publication Data
US 2011/0212490 A1    Sep. 1, 2011

Related U.S. Application Data

(60) Provisional application No. 60/844,259, filed on Sep. 12, 2006.

(51) Int. Cl.
*C12P 19/34* (2006.01)
(52) U.S. Cl. .................................................. 435/91.2
(58) Field of Classification Search .................. None
See application file for complete search history.

(56) References Cited

U.S. PATENT DOCUMENTS

2003/0165979 A1* 9/2003 Chui et al. ................... 435/6

FOREIGN PATENT DOCUMENTS

WO        2005/111236        11/2005

OTHER PUBLICATIONS

Hill et al. (2002) Appl. Environ. Microbiol. vol. 68(6):3055-3066.*
Broude; et al., "Multiplex allele-specific target amplification based on PCR suppression", PNAS (2001), 48 (1):206-211.
Dahl; et al., "Multiplex amplification enabled by selective circularization of large sets of genomic DNA fragments", Nucleic Acids Research (2005), 33(8) e71, 7 pages.
Stenberg; et al., "PieceMaker: selection of DNA fragments for selector-guided multiplex amplification", Nucleic Acids Research (2005), 33(8) e72, 6 pages.
Syvanen, Ann-Christine, "Toward Genome-wide SNP genotyping", Nature Genetics (2005), 37:S5-S10.

* cited by examiner

*Primary Examiner* — Gary Benzion
*Assistant Examiner* — Suchira Pande
(74) *Attorney, Agent, or Firm* — Bozicevic, Field & Francis LLP; Bret E. Field

(57) ABSTRACT

Methods and compositions for performing low background multiplex nucleic acid amplification reactions are provided. Aspects of the invention include contacting a nucleic acid sample with two or more primer pairs for two or more target nucleic acids under template dependent primer extension reaction conditions, e.g., polymerase chain reaction (PCR) conditions. The resultant amplified composition is then contacted with target nucleic acid circularizing reagents, and product circularized target nucleic acids are then selected, e.g., for further amplification. Also provided are systems and kits that find use in practicing embodiments of the inventions.

15 Claims, 16 Drawing Sheets

Figure 12

| Forward Primer | SEQ ID NO: | Reverse Primer | SEQ ID NO: | Gene-Collector probe | SEQ ID NO: |
|---|---|---|---|---|---|
| AKT-1 | | | | | |
| TCAGCTTCCTTTGCTTCTCC | 65 | CAGACCCTGGGGCTACTACC | 237 | negative control (no probe) | |
| CGAGGGTCTGACGGGTAG | 66 | CCTGGTGGGCAAAGAGG | 238 | negative control (no probe) | |
| GTGGGTGGTATGCAAGGG | 67 | GAGGATGCTACAGGCAGAG | 239 | CUCUGCCUGUAGCCAUCCUGUGGGUGGUAUGCAAGGG | 409 |
| GTGAAAGACGTGGGGTGG | 68 | CAGCCCTCCACAGTCCAAG | 240 | GUCGGGAGGUGUCAGGUUCGUGAAAGACGUGGGGUGG | 410 |
| CAGCTGGGCACTGTTGG | 69 | CATCGTCCCCTAGAGACAGC | 241 | GUAGCAGGGGAUCUCUGUCGCAGCUGGGCACUGUUGG | 411 |
| GTATCAAGCAGCGTGGTGTC | 70 | TCTGGTGCCATGGAGAGTAG | 242 | AGACCAOGGUACCUCUCAUCGUAUCAAGCAGCGU GGUGUC | 412 |
| ACCCGGTCTGAGAAACC | 71 | GCTCAGGACGTGGGGAC | 243 | CGAGUCCUGCACCCCUGACCCGGUCUGAGAAACCC | 413 |
| CAAGCACGTCACACCCTCC | 72 | CTGGGGATGAGGGGGATG | 244 | GACCCUACUCCCCUACCAAGCACGUCACACCCUCC | 414 |
| TACATCACAGAGGAAGGGG | 73 | AGTGTGGATATGTGGGGAGC | 245 | UCACACCUAUACACCCCUGUACACAUCACAGAGG AAGGGG | 415 |
| ACACTTGAGGGTGTGCTGG | 74 | TGAACACTGCAGGCCTCTC | 246 | ACUUGUGACGUCCGGAGAGACACUUGAGGGUGU GCUGG | 416 |
| GTGGGTGGGTGGAGGTG | 75 | AATACAGATCATGGCACGAGG | 247 | UUAUGUCUAGUACCGUGCCUGCGUGGGUGGGUGG AGGUG | 417 |
| AKT-2 | | | | | |
| ATGTCCTGCTGCCCTGAG | 76 | GCACAGCTTTCCAGGAGGAG | 248 | CUCCUCCUGGAAAGCUGUGCAUGUCCUGCUGCC CUGAG | 418 |
| ACCTGGGACATCACTCAACC | 77 | AAGTCCCACACAAGCCCTAAG | 249 | CUUAGGGCUUGUGUGGGACUUACCUGGGACAUCA CUCAACC | 419 |
| CTGCAGGCTAGCAGGGC | 78 | CCTTTTCTCCTCACACCAGG | 250 | CCUGGUGUGAGGAGAAAAGGCUGCAGGCUAGCA GGGC | 420 |
| ATTTGTTGCCTGTTGCTG | 79 | AGGGCAGCCTTGTCTCTCAG | 251 | CUGAGAGACAAGGCUGCCCUAUUUGCCUUGCUG UUGCUG | 421 |
| GTTAAAATTTCCTCCCACGG | 80 | CTCAGGGTCAGGCTCCAG | 252 | CUGGAGCCUGACCCUGAGGUUAAAAUUUCCUCCC ACGG | 422 |
| GAGTGGGCAGGTGTGGTG | 81 | TCTGAGCTCTGTCAAAGGC | 253 | GCCUUUGACAGAGCUCAGAGAGUGGGCAGGUG UGGUG | 423 |
| CAGCAGAGCCCTCCTCC | 82 | CATCTCACCCACAGTCCTC | 254 | GAGGAGCGUGUGGGUGAGAUGCAGCAGAGCCCUC CUCC | 424 |
| AAGGTGAGGCAGGTGG | 83 | AACTTCCCCAGTGTGAGTCC | 255 | GGACUCACACUGGGGAAGUUAAGGUGAGGCAGG UGG | 425 |
| TTCCCTGGAAGGAAAGGC | 84 | CAGGGACAGTGGCAGCAG | 256 | CUGCUGCCACUGUCCCUGUUCCUGGAAGGAAA GGC | 426 |

Figure 12 (cont.)

| | | | | |
|---|---|---|---|---|
| CTCCGAAAGCCGTCTG | | | GAGGGAUGGGAUCUGCUCUCUCGAAAGCCCGUCUG | 427 |
| GTTTCCCCAGGGAGTCTGG | | | CAUCACCCGCCUGGGGUGUUUCCCAGGGAGUCUGG | 428 |
| APC | | | | |
| TTTTGTTTCCTTTACCCCTTTC | 87 | GCCATTGGAGTTTACACTTATTTC | 259 | GAAAAUAAGUGUAAAACUCCAAUGCUUUUGUUUCCUUUUACCCCUUUC | 429 |
| TAAGGTGCGTGCTTTGAGAG | 88 | ACCAACACCCAAATCGAGAG | 260 | CUCUCGAUUUGGGGUGUGGUUAAGGUGCGUGCUUUGAGAG | 430 |
| TGTTTTCAGTCATGTATATTTGTGG | 89 | GCAATCAATAACATGCTATCTTTGAG | 261 | CUCAAAGAUGAUGCAUGUAUUGAUUGCUGUUUUCAGUCAUGUAUAUUUGUGG | 431 |
| TGCTCTTCTGCAGTCTTATTAGC | 90 | CAGGGCCTAAAGTTGGGTAAAAC | 262 | GUUUUACCCAACUUUAGGCCUGUGCUCUCUCUGCAGUCUUUAUUAGC | 432 |
| TCATGCACCATGACTGACG | 91 | AGAGCCAAAATAAACACAGCC | 263 | GGCUGUGUUUAUUUUGGCUCUUCAUGCACCAUGACUGACG | 433 |
| TGCGGTGAGCTGAGATTATG | 92 | GGGGTTTCTGGAGTAAACACAG | 264 | CUGUGUUUACUCCAGAAACCCUGCGGUGAGCUGAGAUUAUG | 434 |
| CCTTGGGCTAAGAAAGCCTAC | 93 | TTCTTAGAACCATCTTGCTTCATAC | 265 | GUAUGAAGCAAGAUGGUUCUAAGAACCUUGGGCUAAGAAAGCCUAC | 435 |
| TGCTCATATGCAAGAAACTCTC | 94 | AGAGATGGGGTTTTGCCAC | 266 | GUGGCAAAACCCCAUCUCUCGUUCUCACAUGCAAGAAACUCUC | 436 |
| CACTGATTACTTCATCCTGGAAAG | 95 | TGGCTGATATGAATTTTCTCCTC | 267 | GAGGAGAAAAUUCAUAUCAGCCACACUGAUUACUUCAUCCUGGAAAG | 437 |
| AGGGTTTATATTAGTGATCCTGC | 96 | TTGGTGGCCTTATATCCTAATTC | 268 | GAAUUAGGAUAUAAGGCCACCAAAGGGUUAUAUUAGUGAUCCUGC | 438 |
| TGGCATAAAATGGAATAATTGTC | 97 | AGCGAATGTGAAGCACAG | 269 | CCUGUGCUUCACAUUCCGUUGGCAUAAAAUGGAAUAAUUGUC | 439 |
| AAAGCTTGGCTTCAAGTTGTC | 98 | AGTGAGACCCTGCCTCAAAG | 270 | CUUUGAGGCAGGGUCUCACUAAAGCUUGGCUUCAAGUUGUC | 440 |
| TGTTACCCAGAAGGTCTTGAAC | 99 | GAAATCTCATGCTAAAAGAAGG | 271 | CCUUCUUUUUAGCAUGAGAUUUCUGUUACCCAGAAGGUCUUGAAC | 441 |
| AGTGAGGGACGGGCAATAG | 100 | CCTCCACCTATGGGCTACAC | 272 | GUGUAGCCCAUAGGUGGAGGGACGGGCAAUAG | 442 |
| TTTGTTGTTACTGCATACACATTG | 101 | GGGTAACACTGTAGTATTCAAATATGG | 273 | CCAUAUUUGAAUACUACAGUGUUACCCUUUGUUGUUACUGCAUACACAUUG | 443 |
| AAGCAGAGACACAAGCAAAGTC | 102 | CAATCGAGGGTTTCATTTGAC | 274 | GUCAAAUGAAACCCUCGAUUGAAGCAGAGACACAAGCAAAGUC | 444 |
| AAGTCGGAAAATTCAAATAGGAC | 103 | TTCAGAGTAACGTTCACTATATAATTGG | 275 | CCAAUUAUAUAGUGAACGUUACUCUGAAAAGUCGGAAAAUUCAAAUAGGAC | 445 |
| TTCTCCATACAGGTCACGGG | 104 | CCTGTGTCGTCTGATTACATCC | 276 | GGAUGUAAUCAGAACGACACAGGUUCUCCAUACAGGUCACGGG | 446 |
| TGCAAAGTTCTTCTTATTAACCAAG | 105 | CGCTTGGTTTGAGCTGTGTTTG | 277 | CAAACAGCUCAAACCAAGCGUGCAAAGUUCUUCUUAUUAACCAAG | 447 |
| AGCCCCAGTGATCTTCCAG | 106 | AGCTGACTTGGGTTTCCTTGC | 278 | GCAAGGAAACCCAAGUCAGCUAGCCCCAGUGAUCUUCCAG | 448 |

Figure 12 (cont.)

| | | | | |
|---|---|---|---|---|
| AAAAGGACCTATTAGATGATTCAGATG | 107 | TTTGTTGGGTGCAGAAGAAAG | 279 | CUUCUUCUGCACCCAACAAAAAGGACCUAUUAGAUGAUUCAGAUG | 449 |
| ATTCTGCTATGCCCAAAGGG | 108 | GCTGACCTGGATTTATTGGC | 280 | GCCAAUAAAUCGAGGUCAGCAUUCUGCUAUGCCCAAAGGG | 450 |
| AATAAGGAATCAGAGGCTAAAGTTAC | 109 | AAGTGTCAGATCTTCACCTAATATGC | 281 | GCAUUAGGUGAAGAUCUGACACUUAAUAAGGAAUCAGAGGCUAAAGUUAC | 451 |
| GATGACCTGTTGCAGGAATG | 110 | GAATCATTGTCCTGCTCG | 282 | CGAGGCAGGACAAUGAUUCGAUGACCUGUUGCAGGAAUG | 452 |
| AAAGTTTGATTACTGGAAAAGTTCG | 111 | TCCTTTGGAGGCAGACTCAC | 283 | GUGAGUCUGCCUCCAAAGGAAAAGUUUGAUUACUGGAAAGUUCG | 453 |
| TCAACTAAGTCCTCAGGTTCTGG | 112 | ACGTTTCCAGGTTCTGACC | 284 | GGUCAGGAACCUGGAAACGUUCAACUAAGUCCUCAGGUCUGG | 454 |
| CTCCCACCTAATCTCAGTCC | 113 | ATGGGAACACTGCCATTACC | 285 | GGUAAUGCCAGUGUUCCCAUCCCACCUAAUCUCAGUCCC | 455 |
| TTATCAAATGGCACCTGCTG | 114 | AAACCCTCTAACAAGAATCAAACC | 286 | GGUUUGAUUCUUGUUAGAGGGUUUUAUCAAAUGGCACCUGCUG | 456 |
| EGFR | | | | | |
| CCCCTGACTCCGTCCAG | 115 | AAACAGGAAAGGACGGGC | 2 | GCCCGUCCUUUCCUGUUUCCCUGACUCCGUCC AG | 457 |
| ACCTGGACCTTGAGGGATTG | 3 | CTTCAAGTGGAATTCTGCCC | 4 | GGGCAGAAUUCCACUUGAAGACCUGGACCUUGAGGGAUUG | 458 |
| CCCTGGACCCATTTTAGACC | 5 | CCATCGGAACTGCTGTCTG | 6 | CAGACAGCAGUCCGAUGCCCUGGACCCAUUUUAGACC | 459 |
| AGCACACATGCATCCTTCATGG | 7 | AGTGCTGTAGAGCTCATGG | 8 | GGGGACAGCUCUACAGCACUAGCACAUGCAUCCUUCAUGG | 460 |
| GAAAGGGCGTCATCAGTTTC | 9 | CAAGTGAAGGAAGAGAGGGG | 10 | CCCCUCUCUUCCUUCACUUGGAAAGGGCGUCAUCAGUUUC | 461 |
| CCCTGGGAAATGATCCTACC | 11 | GTCTTCTGTCCTGGTGTGGG | 12 | CCCACACCAGGACAGAAGACCCCUGGGAAAUGAUCCUACC | 462 |
| CGCTTCCTCCCGTGTGTG | 13 | AGGAGACAGAGCGGGACAAG | 14 | CUUGUCCCGCUCUGUCUCCUCGGACCUCCCCGUGUGUG | 463 |
| CTCAAGAGGACCTGGACCG | 15 | GAGCCCAGCCTCAGCAG | 16 | CUGCUGAGGCUGGGCUCUCAAGAGGACCUGGACCG | 464 |
| GGATCCCTAGCTATTCTTAATCCAAC | 17 | GGAAATATGTCGAAAAGTTCTCTC | 18 | GAGAGAGAACUUUUCGACAUUUCCGGAUCCCUAGCUAUUCUUAAUCCAAC | 465 |
| CAGAGTCCCTGAGAGTCTAGAGTAATG | 19 | GAGCTCTGTGCCCTATCTTAGC | 20 | GCUAAGAUAGGGCACAGAGCUCCAGAGUCUAGAGUAAUG | 466 |
| CTCCCACAGCATGACTGACCTACC | 21 | GGAATTCACATGGTAATTTCACAG | 22 | CUGUGAAAUUACCAUGUGAAUUCCUCCCACAGCAUGACCUACC | 467 |
| AAGGTGCCGTCTCCTCC | 23 | GCTATAACAACAACCTGGAGCC | 24 | GGCUCCAGGUUGUUGUUAUAGCAAGGUGCCGUCUCCUCC | 468 |
| AGAGGTGATTTGTGTTCCTGC | 127 | TCATCACTGTTCGGCTTCTG | 299 | CAGAAGCCGAACAGUGAUGAAGAGGUGAUUUGUGUUCCUGC | 469 |
| TATCATTGGCCTTTCCCAC | 128 | ATTTGTTGCCGAAAACTTG | 300 | CAAGUUUUCGGCAACAAAUUAUCAUUGGCCUUUCCCCAC | 470 |

Figure 12 (cont.)

| | | | | | |
|---|---|---|---|---|---|
| TCTCCAAAATATGCCAAGAAG | 129 | CCACAGCAGTGTGGTCATTC | 301 | GAAUGACCACACUGCUGUGGUCUCCAAAAUAUAU GCCAAAGAAG | 471 |
| GGCCATGGAATCTGTCAGC | 130 | AACTGCTAATGGCCCGTTC | 302 | GAACGGGGCCAUUAGCAGUUGGCCAUGGAAUCUG UCAGC | 472 |
| TTTCCAGCATGGTGAGGG | 131 | ACAGCTTGCAAGGACTCTGG | 303 | CCAGAGUCCUUGCAAGCUGUUUUCCAGCAUGGU GAGGG | 473 |
| AGCATGTGGCACCATCTCAC | 132 | AGACATGAGAAAAGGTGGGC | 304 | GCCCACCUUUUCUGAGUCUAGGCAUGUGGCACCA UCUCAC | 474 |
| CATGTGCCCCTCCTTCTG | 133 | CTATCCCAGGAGCGCAGAC | 305 | GUCUGCGCUCCUGGGAUAGGCAUGUCCCCUCCU UCUG | 475 |
| AATTCGGATGCAGAGCTTC | 134 | TACAGCTAGTGGGAAGGCAG | 306 | CUGCCUUCCCACUAGCUGUAAAUUCGGAUGCAGA GCUUC | 476 |
| TCGTCTGTGTGTGTCACTCG | 135 | AAGAAAATACTTGCATGTCAGAGG | 307 | CCUCUGACAUGCAAGUAUUUCUUUUCGUCUGUG UGUGUCACUCG | 477 |
| GCAAGGGATTGTGATTGTTC | 136 | CTGTTTGGCTAAGAGAGCAGCC | 308 | GGCUGCUCUUAGCCAAACAGGCAAGGGAUUGUGA UUGUUC | 478 |
| GCAATGCCATCTTTATCATTTC | 137 | CAGAACACAGTGACATGAGATGC | 309 | GCAUCAUGUCACUGUGUUCUGCAAUGCCAUC UUUAUCAUUUC | 479 |
| AGACCCCTGCTCCTATAGCC | 138 | GAGTTTCACTAGATGTTATTTTCCC | 310 | GGGAAAAUAACCAUCUAGUGAAACUCAGACCCCU GCUCCUAUAGCC | 480 |
| CCTGCATTCAGGAAAAGTGG | 139 | TCCATGTAAAATAGAGCCATAGTG | 311 | CACUAUGGCUCUAUUUUACAUUGGACCUGCAUUCA GGAAAAGUGG | 481 |
| TTGCAAACACTGAAGTTGGG | 140 | TTGGACACTGGAGACTGGC | 312 | GCCAGUCUCCAGUCCAAUGCAAACACUGAAG UUGGG | 482 |
| ATCCTGCATGGGATGGTG | 141 | GTGGCTTGGTCCTGGGTATC | 313 | GAUACCCAGGACCAAGCCACAUCCUGCAUGGGAU GGUG | 483 |
| FRAP | | | | | |
| AGATCTGTGTTGGGTGACCAG | 142 | TGATGGTACATTTAGCCCCACAC | 314 | GUGUGGGCUAAAUGUACCAUCAAGAUCUGUUUG GGUGACCAG | 484 |
| CACTCCCACCACCACAGTTAG | 143 | TAAGTGGCAGACACAGGGTG | 315 | CACCCUGUGUCUGCCACUUACACUCCCACCACCA CAGUUAG | 485 |
| AGTCTGCGTACTTTCCTGGC | 144 | AGAAGGAAGCAAAAGACCCC | 316 | GGGGUCUUUUGCUUCCUUCUCUAGUCCUGCGUACUU GCCUGGC | 486 |
| TCCTGAGAGAACAAAACTCTGG | 145 | AGGCCAGGTGATTCTCTACG | 317 | CGUAGAGAAUCACCUGCCUUCCUGAGAACAA AACUCUGG | 487 |
| ATGGGATGGGCCTGTATTC | 146 | CGCTCACAGAATGGTACACG | 318 | CGUGUACCAUUCUGUGAGCGAUGGAUGGGCCU GUAUUC | 488 |
| GTAGAATCCACAGTGCCAG | 147 | CCTGTTCCCTGTTTACCCTG | 319 | CAGGGUAAACAGGGAACAGGGUAGAAUCCACAGU GCCCAG | 489 |
| GCTTTATAGGACCTTGACTGTTG | 148 | AGCGTCCTTCCTCTCCAAC | 320 | GGUUGGAGAGGAAGGACGCUGCUUUAUAGGACC UUUGACUGUUG | 490 |
| CAAGGTGATTTTGAGCTGGG | 149 | TAACAGTCCAACACTGGGG | 321 | CCCCAGUGUUGGGACUGUUACAAGGUGAUUUUG AGGUGGG | 491 |
| GAGAAAGCTGTTCTTCCCAAG | 150 | TTCCCAAAGTTTCCAGCATC | 322 | GAUGCUGGAAACUUUGGGAAGAAGAAAGCUGUUUC UUCCCAAG | 492 |

Figure 12 (cont.)

| | | | | |
|---|---|---|---|---|
| CAAGCTGCAGACCTACCTGTC | 151 | CTGGGCTACTCCCAATTGTCC | 323 | GGACAAUUGGGAGUAGCCAGCAAGCUGCAGACCU ACCUGUC |
| TGGAGGTAGAAGGTGGGAAG | 152 | TCAAGCAGTTCTCACAGCG | 324 | CGCUGUGAGAACUGCUUGAUGGAGGUAGAAGCU GGGAAG |
| TTTTCTGTTGGACACAGTCTCTC | 153 | TCCCCATATGAGCTGATGAC | 325 | GUCAUCAGCUCAUAUGGGGAUUUUCUGUUGGACA CAGUCUCUC |
| TTATGACTGAGATGGTCTCTTGG | 154 | GAGGTTAGTTCTTTTCCACCC | 326 | GGGUGGAAAAGAAACUAACUCUCUAUGACUGAGA UGGUCUCUUGG |
| CCCGGCCTCCAAATAC | 155 | AAAGAGAAGCAAAGTCCCTGG | 327 | CCAGGGACUUUGCUUCUCUUUCCCGGCCUCCAAA AUAC |
| GAAACCTCTTTTCTTCTTACAGCC | 156 | GCAACCATCTCTCTCTTGCC | 328 | GGCAAGAGAGAUGGUUGCGAAACUCUUUUCU UCUUACAGCC |
| GCAAGGGCTCTGTGAGTGAG | 157 | GCAAGGCTCTGTGAGTGAAG | 329 | CUCACUCACAGAGCCCUUGCGCAAGGGCUCUGU GAGUGAG |
| TAACCATGCTCTGCCTGAAG | 158 | GATCTGTGCATGTGTGGTGC | 330 | GCACCACACAGCAUGCACAGAUCAACCAUGCUCUGC CUGAAG |
| AGCTTAAGGTAAGCCTGGGG | 159 | TTCAAACTTGCTTCTGAGCC | 331 | GGCUCAGAAGCAAGUUUGAAAGCUUAAGGUAAGC CUGGGG |
| CTTTTCTGGGCATCTTGATTC | 160 | CCAGGGACTCAGAGGAAATC | 332 | GAUUUCCUCUGAGUCCCUGGCUUUUCUGGCCAU CUUGAUUC |
| TGTCCTTAGATACTTGGGACCTG | 160 | GCCTTGGGAACTTAAGAAATGAAC | 333 | GUUCAUUUCUUAAGUUCCCAAGCUCUGUCCUUAGAU ACUUGGGACCUG |
| CCCTCAGTCAGGTCTCTTCC | 162 | TGGGTCACAGAGACAAAGTCTTC | 334 | GAAGACUUUGUCUCUGUGAGCCACCCUCAGUCACGU CUCUUCC |
| CCAGAAGAAATGGTCATAATGTAG | 163 | CACAAACTCCCATAGCCAAG | 335 | CUUGGCUAUGGGAGUUUGUGCCAGAAGAAAUG GUCAUAAUGUAG |
| TCTACCAGGTCTCGCACCTCC | 164 | CTGGTTTTCGGGTTGCCC | 336 | GGGCAACCCGAAAACCAGUCUACCAGGUCUGCAC UCC |
| AGGGGAATTTTATCGTGAAAG | 165 | CCAGCCCCCTTGATTATTACTTC | 337 | GAAGUAAUAAUCAAGGGGCUGGAGGGGAAUUUUA UCGUGAAAG |
| AGTGTGACTTTGAGGCAGC | 166 | GCAGTGGGAGAAGAGAGGTC | 338 | GACCUCUCUUCUCCCACUGCAGGUGUGACUUUGA GGCAGC |
| CCCACATCTCTACCCTCAG | 167 | TGAAGGTCAGGGGCCAATAAC | 339 | GUUAUUGGCCCCUGACCUUCACCCACAUCUCCUAC CCUCAG |
| GCGTACAGCAGCACATTAGG | 168 | AAGTGAGAACTCCGTGTGTGGG | 340 | CCCACACGGAGUUCUCACUUGCGUACAGCAGCAC AUUAGG |
| GGGCAGGAGAGGAAGATTG | 169 | GAGCCCCTAGCCTCACTCAC | 341 | GUGAGUGAGGCUAGGGGCUCGGCCAGGAGAGGA AGAUUG |
| CTGCCTTTAGCCAACCAG | 170 | TCTTTACCAAAGCACCGTGG | 342 | CCACGGUGCUUUGGUAAAGACUGCCUUUAGCCCA ACCAG |
| CTGTAGCTAGTTGGGGTGCC | 171 | GTCCTTGGAAGGGGTAGGG | 343 | CCCUACCCCUUCCAAGGACCUGUAGCUAGUUGGG GUGCC |
| ACAGAGCAAGACTCTGCCAC | 172 | GCAGAGCGAAGCAGATTAGG | 344 | CCUAAUCUGCUUCGCUCUGCACAGAGCAAGACUC UGCCAC |
| GAACGGTAGCTCCCTTCCTC | 173 | GCAGAAGCTGCTGGGATG | 345 | CAUCCCAGCAGCUUCUGCGAACGGUAGCUCCCUU CCUC |

| | 493 |
| | 494 |
| | 495 |
| | 496 |
| | 497 |
| | 498 |
| | 499 |
| | 500 |
| | 501 |
| | 502 |
| | 503 |
| | 504 |
| | 505 |
| | 506 |
| | 507 |
| | 508 |
| | 509 |
| | 510 |
| | 511 |
| | 512 |
| | 513 |
| | 514 |
| | 515 |

Figure 12 (cont.)

| | | | | |
|---|---|---|---|---|
| TTAGGAGGGCTGTTTTGAGG | 174 | TCAGCTGTAACCACGAGCAC | 346 | GUGCUCGUGGUUACAGCUGAUUAGGAGGGCUGUUUUGAGG | 516 |
| GTTCCTCAGCATGGACCTTG | 175 | CTCAGAGAGCCTGGCACC | 347 | GGUGCCAGGCUCUCUGAGGUUCCUCAGCAUCGA | 517 |
| CCACCCTTGAAGTAGGTACAG | 176 | AGGGTCAGGAAGGGAAAGAG | 348 | CUCUUUCCCUUCUGACCCUCACCCUUUGAAGUAGGUACAG | 518 |
| CTGCCAGCTCTCTTCTCAGG | 177 | AGCTTTTGGAAAAGGCTGACC | 349 | GGUCAGCCUUUUCAAAAGCUCUGCCAGCUCUCUUCUCAGG | 519 |
| ATACCAGCTCTTCCCCAACC | 178 | CCCACCAGCTAAGGGACC | 350 | GGUCCCUUAGCUGGUGGGAUACCAGCUCUUCCC CAACC | 520 |
| TTCCTCTGACTGCTGGAAATAG | 179 | TGGGTCACGTCCTTTCATTC | 351 | GAAUGAAAGGACGUGACCCAUUCCUCUGACUGCU GGAAAUAG | 521 |
| ATATCTCAGTCAGCCTGGG | 180 | CCAGATGCTTTGGAATGAGTG | 352 | CACUCAUUCCAAAGCAUCUGGAUAUCUGCAGUCA GCCUGGG | 522 |
| GCGTTTAAATTCTTCCCTGG | 181 | GAAGAGGGAAGGGGTCTCAG | 353 | CUGAGACCCCUUCCUCUUCGCGUUUAAUUCUU CCCUGG | 523 |
| CAGCTGAAGAGCTGAGGACC | 182 | ATGACTACACGAGACAAATGTAGG | 354 | CCUACAUUUGUCUCGUGUAGUCAUCAGCUGAAGA GCUGAGGACC | 524 |
| TCTGCCTGTGTTCTGAGCTG | 183 | AGCAGGGCTACGGAGATTC | 355 | GAAUCCCGUAGCGCUGCUUGCCCUGUGUUCU GAGCUG | 525 |
| ACCCCAAGCCTTGTTCTTC | 184 | CATCCTATTGCGAGTGGGG | 356 | CCCCACUCGCAAUAGGAUGACCCCAAGCCUUGUU UCUUC | 526 |
| CTCGGTTCTCAAAGTACAAACC | 185 | AAACCAAATGAAACCATTCAGG | 357 | CCUGAAUGGUUUCAUUUGGUUUCUCGCUCUCAAA AGUACAAACC | 527 |
| CGTTTGCCAACTCCTAGCTTAC | 186 | TGGGCTTAAGTCTGCCTACAG | 358 | CUGUAGGCAGACUUUCCUCACGUUUGCCAACUC CUAGCUUAC | 528 |
| AGAGGAAAAGCCACCTGCTC | 187 | AAGGCTGTAACTGTCCTGATCC | 359 | GGAUCAGGACAGUUACAGCCUUAGAGGAAAAGCCA CCUGCUC | 529 |
| ACATGGCCTGTGTCTGCTTC | 188 | CAAGCAACTCCTCTGCCTTG | 360 | CAAGGCAGAGGAGUUGCUUGACAUGGCCUGUGU CUGCUUC | 530 |
| GACTGGAAGAAAATAACCAAGTTTC | 189 | ACAAACACTCTGCACAAGGG | 361 | CCCUUGUGCAGAGUGUUUGUGACUGGAAGAAAAU AACCAAGUUUC | 531 |
| ATGCTAACACCAACAGTGGC | 190 | TCAGAGAGGAAAGTGTGCTCAG | 362 | CUGAGCACACUUCCUCUCUGAAUGCUAACACCA ACAGUGGC | 532 |
| AGGGAACAAGAAGTGCATCG | 191 | TTTGTACTCTGGCTTTGGG | 363 | CCCAAAGCCAGAGUACAAAGGGAACAAGAAGU GCAUCG | 533 |
| KRas | | | | | |
| TTAAAAGGTACTGGTGGAGTATTTG | 192 | CCTTTATCTGTATCAAAGAATGGTC | 364 | GACCAUUCUUUGAUACAGAUAAAGGUUAAAAGGU ACUGGUGGAGUAUUUG | 534 |
| TCTTTGGAGCAGGAGAACAATG | 193 | TGCATGGCATTAGCAAAGAC | 365 | GUCUUUGCUAAUGCCAUGCAUUGUUCUCCUGAGCAGGA ACAAUG | 535 |
| AGAAGGAAGGAAAATTTGGTG | 194 | AGAAGCAAATGCCCTCTCAAG | 366 | CUUGAGAGGGCAUUGCUUCUAGAGGAAGGAAAA UUUGGUG | 536 |
| AACTTCTCTGCACATGGCTTTC | 195 | GTGGTTGCCACCTTGTTACC | 367 | GGUAACAAGGUGGCAACCACAACUUCUGCACAU GGCUUC | 537 |

Figure 12 (cont.)

| MARK-3 | | | | |
|---|---|---|---|---|
| CCTAGGGCTGTGCTGTTTG | 196 | GAGGAGCACGAATGCCAC | 368 | GUGGCAUUGUGCUCCUCCCUAGGGCUGUGCUG UUUUG | 538 |
| TGGTTAAATTCCTTTGAAGTGC | 197 | ATGGTGTGAACCCGGGAG | 369 | CUCCCGGGUUCACACCAUUGGUUAAAUUCCUUUG AAGUGC | 539 |
| TGCCATATATCTTGGCATTTATC | 198 | TTAGATGGCAATTAGCACCG | 370 | CCGUGCUAAUUGCCAUCUAAUGCCAUAUAUCUUG GCAUUUAUC | 540 |
| AAGCTTTTAACCTGTCTTCAGC | 199 | AAGCTTTAACCTGTCTTCAGC | 371 | GCUGAAGACAGGUUAAAAGCUUAAUGGAAGCAU UUGGAAUAC | 541 |
| TGCATGGTTTGTGCATACAG | 200 | CCATATGGGCAGTATGGTTG | 372 | CAACCAUACUGCCCAUAUGGUGCAUGUGUUGUGC AUACAG | 542 |
| CAAATTCCACATATTTCTGGCTAAC | 201 | AAACACTTGTTTGCTTCAGGG | 373 | CCCUGAAGCAGAAAACAAGUGUUUCAAAUCCACAUA UUUCUGGCUAAC | 543 |
| ATTTTCATCTTAATTACGAATCTGC | 202 | TGACCACTGAGAGAACTGCAC | 374 | GUGCAGUUCUCUCAGUGGUCAAUUUUCAUCUUAA UUACGAAUCUGC | 544 |
| AAAGCTTTTCTAAAATGCCTAATCC | 203 | CAGAGAGAAAGAAAACGAGTAAGTC | 375 | GACUUACUCGUUUUCUUCCUCUGAAAGCUUUUC UAAAAUGCCUAAUCC | 545 |
| AACATTATATCAGTGCGGGG | 204 | CCATTATTCACATTTTAGGCACAG | 376 | CUGUGCCUAAAAAUGUGAAUAAUGGAACAUUAUAU CAGUGCGGGG | 546 |
| TTGCTTGAATCTGGGAGGTG | 205 | GCCAATATCCATCATTAAGGG | 377 | CCCUUAAUGAUGGAUAUUGGCUUGCUUGAAUCUG GGAGGUG | 547 |
| ATAAGCCATTTGGGTTCGTG | 206 | AGGAGACCTCTTGCTGGAC | 378 | GUCCAGCAAGAGGUCUCCUAUAAGCCAUUUGGG UUCGUG | 548 |
| TGGTTACTGTCACAAAATAAAACTTG | 207 | CCTGTGTCTCAGCTGGTTCC | 379 | GGAACCAGCUAGACACCAGGUGGUUACUGUCACA AAAUAAAACUUG | 549 |
| GGTGACAGAGTAAGACCTTGCC | 208 | GCAGTAAATAACATGCTTCCATTTC | 380 | GAAAUGGAAGCAUGUAUUAUACUGCGGUGACAGA GUAAGACCUUGCC | 550 |
| TTTATACCGATTTTCTCCACTG | 209 | CCAGGTAGCAGTGGCTTCAC | 381 | GUGAAGCCACUGCUACCUGGUUUAUACCGAUUU UCUCCACUG | 551 |
| CATTTATGGTGTTGGTGTTGG | 210 | AAAATAGTCGCCTCTGCCAC | 382 | GUGGCAGAGGCGACUAUUUUCAUUUAUGGUGU UGGUGUUGG | 552 |
| TGAAGTGTAAGAGAGGTTGATTTTCC | 211 | ACATTTCCATCAGTGTTCAGG | 383 | CCUGAACACUGAUGGAAAUGUUGAAGUGUAAGAG GUUGAUUUUCC | 553 |

| SMAD-4 | | | | |
|---|---|---|---|---|
| CAAAGGATCAAAAATTGCTTCAG | 212 | GTAGCTTGAAAGGAAACGTAGC | 384 | GCUACGUUUCCUUUCAAGGAUCAAAGGAUCAAA AUUGCUUCAG | 554 |
| CTGAGTTGGTAGGATTGTGAGG | 213 | GTCGCGGGCTATCTTCC | 385 | GGAAGAUAGCCCGCGACCUGAGUUGGUAGGAUU GUGAGG | 555 |
| GCGTTTATGCTACTTCTGAATTG | 214 | TTAATGTTACTGCCTGCCGC | 386 | GCGGCAGGCAGUAACAUUAAGCGUUUAUGCUACU UCUGAAUUG | 116 |
| CCGCTGAATAAATGACTTTTGC | 215 | TTCCAAGTGATTGTGCATACC | 387 | GGUAUGCACAAUCACUUGGAACCGCUGAAUAAAU GACUUUUGC | 117 |
| CCCATCTTTATAGTTGTGCATTATC | 216 | AAAACAGAAAAACAAAGCCCTACC | 388 | GGUAGGGCUUUGUUUUUCUGUUUUUCCAUCUUUA UAGUUGUGCAUUAUC | 118 |

Figure 12 (cont.)

| | | | | |
|---|---|---|---|---|
| TTGGCAGATAGCACTGAAATG | 217 | TTAAAGCCTGTGTTTGTGCG | 389 | CGGCACAAACACAGGCUUUAAUUGGCAGAUAGCAC UGAAAUG | 119 |
| TGTGGAGTCAAGTGAAGC | 218 | TGTACATGGGAAAACATAACCTTG | 390 | CAAGGUAUGUGUUCCCAUGUACAUGUGGAGUGC AAGUGAAAGC | 120 |
| GAATTCATACTACATGCTCCTGACAC | 219 | TTTTCATTCCTTCCACCC | 391 | GGGUGGAAGGAAUGGAAAAGAAUUCAUACUACAU GCUCUGACAC | 121 |
| TCCAAGCCACCTTTCCTAAC | 220 | ACAGAAGAACAGATTTTACCAATTC | 392 | GAAUUGGUAAAAUCUGUUUCUCUUCCUUCCAAGCCA CCUUUCCUAAC | 122 |
| AGGATGGGAAGAGATCACCC | 221 | CAGGATTGTATTTTGTAGTCCACC | 393 | GGUGGACUACAAAAUACAAUCCUGAGGAUGGGAA GAGAUCACCC | 123 |

TGF-beta R2

| | | | | |
|---|---|---|---|---|
| CATCTGGCCCGCACATC | 222 | GAAACTTCCTCGTTTTCGGC | 394 | GCGGAAACGAGGAAAGUUUCCAUCUGGCCCGCAC AUC | 124 |
| TTCAGGAATTCATTGGCAGG | 223 | GGAAAGGGAAATGGAACAGG | 395 | CCUGUUCCCAUUUCCCUUUCCUUCAGGAAUUCAUU GGCAGG | 125 |
| TTCCAGATTGCCTTTCTGTC | 224 | ATGCAATCCACCACAGGAG | 396 | CUCCUGUGGUGGAUUGCAUUUCCAGAUUGCCUU UCUGUC | 126 |
| GCATGAACCCACTTCCTGAC | 225 | CATGCTTCAGATTGATGTCTGAG | 397 | CUCAGACAUCAAUCUGAAGCAUGGGUCAUGAACCCA CUUCCUGAC | 287 |
| AGAGCAGTTTGAGACAGTGGC | 226 | AAGAGGTAGGGTGAGGCCAG | 398 | CUGGCCUCACCCUACCUCUUAGAGACAGUUUGAGA CAGUGGC | 288 |
| TCTGCACGTGTCAGGG | 227 | CCCTGGAATAATGCTCGAAG | 399 | CUUCGAGCAUUAUUCCAGGGGCUCACCUGUCA GGGG | 289 |
| CATGCTCATTTCCTTTGGC | 228 | TTCCAGAATTCTCTGCCACC | 400 | GGUGGCAGAGAAUUCUGGAACAUGCUCAUUUCCU UUGGC | 290 |
| TAGCAACAAGGTCAGCAGGC | 229 | CTGTTCTTTGGGTGAGAGGGG | 401 | CCCCUCUCACCCAAAGAACAGUAGCAACAAGGUCA GCAGGC | 291 |

TP53

| | | | | |
|---|---|---|---|---|
| ATGCTGGATCCCCACTTTTC | 230 | GACCAGGTCGTCAGCCC | 402 | GGGCUGAGGACCUGGUCAUCCUGGAUCCCCACU UUUC | 292 |
| GACAAGGGTTGGGCTGG | 231 | CCAAAGGGTGAAGAGGAATC | 403 | GAUUCCUCUUCACCCUUUGGGACAAGGGGUUGGG CUGG | 293 |
| TCTTTGCTGCGCGTCTTCC | 232 | AGGGCCACTGACAACCAC | 404 | GUGGUUGUCAGUGGCCCUCUUGACUGCUGCCGUCU UCC | 294 |
| TGCTTGCCACAGGTCTCC | 233 | GTCAGAGGCAAGCAGAGGC | 405 | GCCUCUGCUUGCCUCUGGACAAGGCUUGCCACAGGU CUCC | 295 |
| GGACAGGTAGGACCTGATTTCC | 234 | AAACAGTCAAGAAGAAAACGGC | 406 | GCCGUUUUCUUCUUGACUGUUUGGACAGGUAGG ACCUGAUUUCC | 296 |
| AACTTGAACCATCTTTTAACTCAGG | 235 | GGAATCCTATGGCTTTCCAAC | 407 | GUUGGAAAGCCAUAGGAUUCCAACUUGAACCAUC UUUUAACUCAGG | 297 |
| AGGGGCACAGACCCTCTC | 236 | AGACCCAAAACCCAAAATGG | 408 | CCAUUUUGGGUUUUGGGUCUAGGGGCACAGACC CUCUC | 298 |

SEQUENCE LISTING

<160> NUMBER OF SEQ ID NOS: 555

<210> SEQ ID NO 1
<211> LENGTH: 18
<212> TYPE: DNA
<213> ORGANISM: Artificial Sequence
<220> FEATURE:
<223> OTHER INFORMATION: synthetic primer

<400> SEQUENCE: 1
atcctgcatg ggatggtg                                                    18

<210> SEQ ID NO 2
<211> LENGTH: 18
<212> TYPE: DNA
<213> ORGANISM: Artificial Sequence
<220> FEATURE:
<223> OTHER INFORMATION: synthetic primer

<400> SEQUENCE: 2
aaacaggaaa ggacgggc                                                    18

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
acctggacct tgagggattg                                                  20

<210> SEQ ID NO 4
<211> LENGTH: 20
<212> TYPE: DNA
<213> ORGANISM: Artificial Sequence
<220> FEATURE:
<223> OTHER INFORMATION: synthetic primer

<400> SEQUENCE: 4
cttcaagtgg aattctgccc                                                  20

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
ccctggaccc attttagacc                                                  20

<210> SEQ ID NO 6
<211> LENGTH: 19
<212> TYPE: DNA
<213> ORGANISM: Artificial Sequence
<220> FEATURE:
<223> OTHER INFORMATION: synthetic primer

<400> SEQUENCE: 6
ccatcggaac tgctgtctg                                                   19

<210> SEQ ID NO 7
<211> LENGTH: 20
<212> TYPE: DNA

```
<213> ORGANISM: Artificial Sequence
<220> FEATURE:
<223> OTHER INFORMATION: synthetic primer

<400> SEQUENCE: 7
agcacatgca tccttcatgg                                               20

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
agtgctgtag agctgtcccc                                               20

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
gaaagggcgt catcagtttc                                               20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
caagtgaagg aagagagggg                                               20

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
ccctgggaaa tgatcctacc                                               20

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
gtcttctgtc ctggtgtggg                                               20

<210> SEQ ID NO 13
<211> LENGTH: 17
<212> TYPE: DNA
<213> ORGANISM: Artificial Sequence
<220> FEATURE:
<223> OTHER INFORMATION: synthetic primer

<400> SEQUENCE: 13
cgcttcctcc gtgtgtg                                                  17
```

<210> SEQ ID NO 14
<211> LENGTH: 20
<212> TYPE: DNA
<213> ORGANISM: Artificial Sequence
<220> FEATURE:
<223> OTHER INFORMATION: synthetic primer

<400> SEQUENCE: 14
aggagacaga gcgggacaag					20

<210> SEQ ID NO 15
<211> LENGTH: 19
<212> TYPE: DNA
<213> ORGANISM: Artificial Sequence
<220> FEATURE:
<223> OTHER INFORMATION: synthetic primer

<400> SEQUENCE: 15
ctcaagagga cctggaccg					19

<210> SEQ ID NO 16
<211> LENGTH: 17
<212> TYPE: DNA
<213> ORGANISM: Artificial Sequence
<220> FEATURE:
<223> OTHER INFORMATION: synthetic primer

<400> SEQUENCE: 16
gagcccagcc tcagcag					17

<210> SEQ ID NO 17
<211> LENGTH: 26
<212> TYPE: DNA
<213> ORGANISM: Artificial Sequence
<220> FEATURE:
<223> OTHER INFORMATION: synthetic primer

<400> SEQUENCE: 17
ggatccctag ctattcttaa tccaac					26

<210> SEQ ID NO 18
<211> LENGTH: 26
<212> TYPE: DNA
<213> ORGANISM: Artificial Sequence
<220> FEATURE:
<223> OTHER INFORMATION: synthetic primer

<400> SEQUENCE: 18
ggaaatatgt cgaaaagttc tctctc					26

<210> SEQ ID NO 19
<211> LENGTH: 27
<212> TYPE: DNA
<213> ORGANISM: Artificial Sequence
<220> FEATURE:
<223> OTHER INFORMATION: synthetic primer

<400> SEQUENCE: 19
cagagtccct gagagtctag agtaatg					27

<210> SEQ ID NO 20
<211> LENGTH: 22
<212> TYPE: DNA
<213> ORGANISM: Artificial Sequence
<220> FEATURE:
<223> OTHER INFORMATION: synthetic primer

```
<400> SEQUENCE: 20
gagctctgtg ccctatctta gc                                              22

<210> SEQ ID NO 21
<211> LENGTH: 20
<212> TYPE: DNA
<213> ORGANISM: Artificial Sequence
<220> FEATURE:
<223> OTHER INFORMATION: synthetic primer

<400> SEQUENCE: 21
ctcccacagc atgacctacc                                                 20

<210> SEQ ID NO 22
<211> LENGTH: 24
<212> TYPE: DNA
<213> ORGANISM: Artificial Sequence
<220> FEATURE:
<223> OTHER INFORMATION: synthetic primer

<400> SEQUENCE: 22
ggaattcaca tggtaatttc acag                                            24

<210> SEQ ID NO 23
<211> LENGTH: 17
<212> TYPE: DNA
<213> ORGANISM: Artificial Sequence
<220> FEATURE:
<223> OTHER INFORMATION: synthetic primer

<400> SEQUENCE: 23
aaggtgccgt ctcctcc                                                    17

<210> SEQ ID NO 24
<211> LENGTH: 22
<212> TYPE: DNA
<213> ORGANISM: Artificial Sequence
<220> FEATURE:
<223> OTHER INFORMATION: synthetic primer

<400> SEQUENCE: 24
gctataacaa caacctggag cc                                              22

<210> SEQ ID NO 25
<211> LENGTH: 76
<212> TYPE: DNA
<213> ORGANISM: Artificial Sequence
<220> FEATURE:
<223> OTHER INFORMATION: synthetic primer

<400> SEQUENCE: 25
gcccguccuu uccuguuugc aauggaacua agggcaggug gguacuugug uucaacgcau     60
ccugcauggg auggug                                                     76

<210> SEQ ID NO 26
<211> LENGTH: 80
<212> TYPE: DNA
<213> ORGANISM: Artificial Sequence
<220> FEATURE:
<223> OTHER INFORMATION: synthetic primer

<400> SEQUENCE: 26
gggcagaauu ccacuugaag gcaauggaac uaagggcagg uggguacuug uguucaacgc     60
accuggaccu ugagggauug                                                 80
```

<210> SEQ ID NO 27
<211> LENGTH: 79
<212> TYPE: DNA
<213> ORGANISM: Artificial Sequence
<220> FEATURE:
<223> OTHER INFORMATION: synthetic primer

<400> SEQUENCE: 27
cagacagcag uuccgauggg caauggaacu aagggcaggu ggguacuugu guucaacgcc    60
ccuggaccca uuuuagacc                                                79

<210> SEQ ID NO 28
<211> LENGTH: 80
<212> TYPE: DNA
<213> ORGANISM: Artificial Sequence
<220> FEATURE:
<223> OTHER INFORMATION: synthetic primer

<400> SEQUENCE: 28
ggggacagcu cuacagcacu gcaauggaac uaagggcagg uggguacuug uguucaacgc    60
agcacaugca uccuucaugg                                               80

<210> SEQ ID NO 29
<211> LENGTH: 80
<212> TYPE: DNA
<213> ORGANISM: Artificial Sequence
<220> FEATURE:
<223> OTHER INFORMATION: synthetic primer

<400> SEQUENCE: 29
ccccucucuu ccuucacuug gcaauggaac uaagggcagg uggguacuug uguucaacgc    60
gaaagggcgu caucaguuuc                                               80

<210> SEQ ID NO 30
<211> LENGTH: 80
<212> TYPE: DNA
<213> ORGANISM: Artificial Sequence
<220> FEATURE:
<223> OTHER INFORMATION: synthetic primer

<400> SEQUENCE: 30
cccacaccag gacagaagac gcaauggaac uaagggcagg uggguacuug uguucaacgc    60
cccugggaaa ugauccuacc                                               80

<210> SEQ ID NO 31
<211> LENGTH: 77
<212> TYPE: DNA
<213> ORGANISM: Artificial Sequence
<220> FEATURE:
<223> OTHER INFORMATION: synthetic primer

<400> SEQUENCE: 31
cuugucccgc ucugucuccu gcaauggaac uaagggcagg uggguacuug uguucaacgc    60
cgcuuccucc gugugug                                                  77

<210> SEQ ID NO 32
<211> LENGTH: 76
<212> TYPE: DNA
<213> ORGANISM: Artificial Sequence
<220> FEATURE:
<223> OTHER INFORMATION: synthetic primer

<400> SEQUENCE: 32

```
cugcugaggc ugggcucgca auggaacuaa gggcaggugg guacuugugu ucaacgccuc    60
aagaggaccu ggaccg                                                    76
```

<210> SEQ ID NO 33
<211> LENGTH: 92
<212> TYPE: DNA
<213> ORGANISM: Artificial Sequence
<220> FEATURE:
<223> OTHER INFORMATION: synthetic primer

<400> SEQUENCE: 33

```
gagagagaac uuuucgacau auuccgcaa uggaacuaag ggcagguggg uacuuguguu    60
caacgcggau cccuagcuau ucuuaaucca ac                                  92
```

<210> SEQ ID NO 34
<211> LENGTH: 89
<212> TYPE: DNA
<213> ORGANISM: Artificial Sequence
<220> FEATURE:
<223> OTHER INFORMATION: synthetic primer

<400> SEQUENCE: 34

```
gcuaagauag ggcacagagc ucgcaaugga acuaagggca ggugguacu uguguucaac     60 gccagagucc cugagagucu agaguaaug                                      89
```

<210> SEQ ID NO 35
<211> LENGTH: 84
<212> TYPE: DNA
<213> ORGANISM: Artificial Sequence
<220> FEATURE:
<223> OTHER INFORMATION: synthetic primer

<400> SEQUENCE: 35

```
cugugaaauu accaugugaa uuccgcaaug gaacuaaggg cagguggua cuuguguuca     60 acgccuccca cagcaugacc uacc                                           84
```

<210> SEQ ID NO 36
<211> LENGTH: 79
<212> TYPE: DNA
<213> ORGANISM: Artificial Sequence
<220> FEATURE:
<223> OTHER INFORMATION: synthetic primer

<400> SEQUENCE: 36

```
ggcuccaggu uguuguuaua gcgcaaugga acuaagggca gguggguacu uguguucaac    60
gcaaggugcc gucuccucc                                                 79
```

<210> SEQ ID NO 37
<211> LENGTH: 42
<212> TYPE: DNA
<213> ORGANISM: Artificial Sequence
<220> FEATURE:
<223> OTHER INFORMATION: synthetic primer

<400> SEQUENCE: 37

```
gcgttgaaca caagtaccca uuccugcccu taguuccauu gc                       42
```

<210> SEQ ID NO 38
<211> LENGTH: 20
<212> TYPE: DNA
<213> ORGANISM: Artificial Sequence
<220> FEATURE:
<223> OTHER INFORMATION: synthetic primer

```
<400> SEQUENCE: 38 cctgcccttagttccattgc                                          20

<210> SEQ ID NO 39
<211> LENGTH: 20
<212> TYPE: DNA
<213> ORGANISM: Artificial Sequence
<220> FEATURE:
<223> OTHER INFORMATION: synthetic primer

<400> SEQUENCE: 39 tgggtacttgtgttcaacgc                                          20

<210> SEQ ID NO 40
<211> LENGTH: 23
<212> TYPE: DNA
<213> ORGANISM: Artificial Sequence
<220> FEATURE:
<223> OTHER INFORMATION: synthetic primer

<400> SEQUENCE: 40 ggaggctgagaaaatgatcttca                                       23

<210> SEQ ID NO 41
<211> LENGTH: 21
<212> TYPE: DNA
<213> ORGANISM: Artificial Sequence
<220> FEATURE:
<223> OTHER INFORMATION: synthetic primer

<400> SEQUENCE: 41 ccaaggcacgagtaacaagct                                         21

<210> SEQ ID NO 42
<211> LENGTH: 20
<212> TYPE: DNA
<213> ORGANISM: Artificial Sequence
<220> FEATURE:
<223> OTHER INFORMATION: synthetic primer

<400> SEQUENCE: 42 cccagcctctcaccctgtaa                                          20

<210> SEQ ID NO 43
<211> LENGTH: 23
<212> TYPE: DNA
<213> ORGANISM: Artificial Sequence
<220> FEATURE:
<223> OTHER INFORMATION: synthetic primer

<400> SEQUENCE: 43 gatgcaaataaaaccggactgaa                                       23

<210> SEQ ID NO 44
<211> LENGTH: 22
<212> TYPE: DNA
<213> ORGANISM: Artificial Sequence
<220> FEATURE:
<223> OTHER INFORMATION: synthetic primer

<400> SEQUENCE: 44 tgtagagctgtcccccatagga                                        22

<210> SEQ ID NO 45
<211> LENGTH: 21
<212> TYPE: DNA
```

```
<213> ORGANISM: Artificial Sequence
<220> FEATURE:
<223> OTHER INFORMATION: synthetic primer

<400> SEQUENCE: 45
cacctgggca gctgtaagtg t                                              21

<210> SEQ ID NO 46
<211> LENGTH: 21
<212> TYPE: DNA
<213> ORGANISM: Artificial Sequence
<220> FEATURE:
<223> OTHER INFORMATION: synthetic primer

<400> SEQUENCE: 46
ttttacattt caggccaaaa g                                              21

<210> SEQ ID NO 47
<211> LENGTH: 23
<212> TYPE: DNA
<213> ORGANISM: Artificial Sequence
<220> FEATURE:
<223> OTHER INFORMATION: synthetic primer

<400> SEQUENCE: 47
ggctgttcac tgacttacgt ttc                                            23

<210> SEQ ID NO 48
<211> LENGTH: 19
<212> TYPE: DNA
<213> ORGANISM: Artificial Sequence
<220> FEATURE:
<223> OTHER INFORMATION: synthetic primer

<400> SEQUENCE: 48
agcagtcact gggggactt                                                 19

<210> SEQ ID NO 49
<211> LENGTH: 20
<212> TYPE: DNA
<213> ORGANISM: Artificial Sequence
<220> FEATURE:
<223> OTHER INFORMATION: synthetic primer

<400> SEQUENCE: 49
ctcacaggga acctttgctc                                                20

<210> SEQ ID NO 50
<211> LENGTH: 22
<212> TYPE: DNA
<213> ORGANISM: Artificial Sequence
<220> FEATURE:
<223> OTHER INFORMATION: synthetic primer

<400> SEQUENCE: 50
aggtggcacc aaagctgtat tt                                             22

<210> SEQ ID NO 51
<211> LENGTH: 19
<212> TYPE: DNA
<213> ORGANISM: Artificial Sequence
<220> FEATURE:
<223> OTHER INFORMATION: synthetic primer

<400> SEQUENCE: 51
gagacgaagc cacgtgcaa                                                 19
```

```
<210> SEQ ID NO 52
<211> LENGTH: 20
<212> TYPE: DNA
<213> ORGANISM: Artificial Sequence
<220> FEATURE:
<223> OTHER INFORMATION: synthetic primer

<400> SEQUENCE: 52
gggccgacag ctatgagatg                                              20

<210> SEQ ID NO 53
<211> LENGTH: 20
<212> TYPE: DNA
<213> ORGANISM: Artificial Sequence
<220> FEATURE:
<223> OTHER INFORMATION: synthetic primer

<400> SEQUENCE: 53
ggcccttcgc acttcttaca                                              20

<210> SEQ ID NO 54
<211> LENGTH: 20
<212> TYPE: DNA
<213> ORGANISM: Artificial Sequence
<220> FEATURE:
<223> OTHER INFORMATION: synthetic primer

<400> SEQUENCE: 54
tgtggagatc gccactgatg                                              20

<210> SEQ ID NO 55
<211> LENGTH: 28
<212> TYPE: DNA
<213> ORGANISM: Artificial Sequence
<220> FEATURE:
<223> OTHER INFORMATION: synthetic primer

<400> SEQUENCE: 55
ctcactctcc ataaatgcta cgaatatt                                     28

<210> SEQ ID NO 56
<211> LENGTH: 23
<212> TYPE: DNA
<213> ORGANISM: Artificial Sequence
<220> FEATURE:
<223> OTHER INFORMATION: synthetic primer

<400> SEQUENCE: 56
ccatgccttt gagaacctag aaa                                          23

<210> SEQ ID NO 57
<211> LENGTH: 24
<212> TYPE: DNA
<213> ORGANISM: Artificial Sequence
<220> FEATURE:
<223> OTHER INFORMATION: synthetic primer

<400> SEQUENCE: 57
gctgtggtca acttactgtt gctt                                         24

<210> SEQ ID NO 58
<211> LENGTH: 26
<212> TYPE: DNA
<213> ORGANISM: Artificial Sequence
<220> FEATURE:
<223> OTHER INFORMATION: synthetic primer
```

```
<400> SEQUENCE: 58
ccaaaattat aagcaacaga ggtgaa                                         26

<210> SEQ ID NO 59
<211> LENGTH: 25
<212> TYPE: DNA
<213> ORGANISM: Artificial Sequence
<220> FEATURE:
<223> OTHER INFORMATION: synthetic primer

<400> SEQUENCE: 59
gacccattag aaccaactcc ataaa                                          25

<210> SEQ ID NO 60
<211> LENGTH: 15
<212> TYPE: DNA
<213> ORGANISM: Artificial Sequence
<220> FEATURE:
<223> OTHER INFORMATION: synthetic primer

<400> SEQUENCE: 60
aggttgccta atgcc                                                     15

<210> SEQ ID NO 61
<211> LENGTH: 15
<212> TYPE: DNA
<213> ORGANISM: Artificial Sequence
<220> FEATURE:
<223> OTHER INFORMATION: synthetic primer

<400> SEQUENCE: 61
gctggtaagc tgtaa                                                     15

<210> SEQ ID NO 62
<211> LENGTH: 15
<212> TYPE: DNA
<213> ORGANISM: Artificial Sequence
<220> FEATURE:
<223> OTHER INFORMATION: synthetic primer

<400> SEQUENCE: 62
ggcattaggc aacct                                                     15

<210> SEQ ID NO 63
<211> LENGTH: 15
<212> TYPE: DNA
<213> ORGANISM: Artificial Sequence
<220> FEATURE:
<223> OTHER INFORMATION: synthetic primer

<400> SEQUENCE: 63
ttacagctta ccagc                                                     15

<210> SEQ ID NO 64
<211> LENGTH: 30
<212> TYPE: DNA
<213> ORGANISM: Artificial Sequence
<220> FEATURE:
<223> OTHER INFORMATION: synthetic primer

<400> SEQUENCE: 64
gctggtaagc tgtaaaggtt gcctaatgcc                                     30

<210> SEQ ID NO 65
<211> LENGTH: 20
<212> TYPE: DNA
```

<213> ORGANISM: Artificial Sequence
<220> FEATURE:
<223> OTHER INFORMATION: synthetic primer

<400> SEQUENCE: 65
tcagcttcct ttgcttctcc                    20

<210> SEQ ID NO 66
<211> LENGTH: 18
<212> TYPE: DNA
<213> ORGANISM: Artificial Sequence
<220> FEATURE:
<223> OTHER INFORMATION: synthetic primer

<400> SEQUENCE: 66
cgagggtctg acgggtag                      18

<210> SEQ ID NO 67
<211> LENGTH: 18
<212> TYPE: DNA
<213> ORGANISM: Artificial Sequence
<220> FEATURE:
<223> OTHER INFORMATION: synthetic primer

<400> SEQUENCE: 67
gtgggtggta tgcaaggg                      18

<210> SEQ ID NO 68
<211> LENGTH: 18
<212> TYPE: DNA
<213> ORGANISM: Artificial Sequence
<220> FEATURE:
<223> OTHER INFORMATION: synthetic primer

<400> SEQUENCE: 68
gtgaaagacg tggggtgg                      18

<210> SEQ ID NO 69
<211> LENGTH: 17
<212> TYPE: DNA
<213> ORGANISM: Artificial Sequence
<220> FEATURE:
<223> OTHER INFORMATION: synthetic primer

<400> SEQUENCE: 69
cagctgggca ctgttgg                       17

<210> SEQ ID NO 70
<211> LENGTH: 20
<212> TYPE: DNA
<213> ORGANISM: Artificial Sequence
<220> FEATURE:
<223> OTHER INFORMATION: synthetic primer

<400> SEQUENCE: 70
gtatcaagca gcgtggtgtc                    20

<210> SEQ ID NO 71
<211> LENGTH: 18
<212> TYPE: DNA
<213> ORGANISM: Artificial Sequence
<220> FEATURE:
<223> OTHER INFORMATION: synthetic primer

<400> SEQUENCE: 71
acccggtctg agaaaccc                      18

```
<210> SEQ ID NO 72
<211> LENGTH: 18
<212> TYPE: DNA
<213> ORGANISM: Artificial Sequence
<220> FEATURE:
<223> OTHER INFORMATION: synthetic primer

<400> SEQUENCE: 72
caagcacgtc acacctcc                                                    18

<210> SEQ ID NO 73
<211> LENGTH: 20
<212> TYPE: DNA
<213> ORGANISM: Artificial Sequence
<220> FEATURE:
<223> OTHER INFORMATION: synthetic primer

<400> SEQUENCE: 73
tacatcacag gaggaagggg                                                  20

<210> SEQ ID NO 74
<211> LENGTH: 19
<212> TYPE: DNA
<213> ORGANISM: Artificial Sequence
<220> FEATURE:
<223> OTHER INFORMATION: synthetic primer

<400> SEQUENCE: 74
acacttgagg gtgtgctgg                                                   19

<210> SEQ ID NO 75
<211> LENGTH: 17
<212> TYPE: DNA
<213> ORGANISM: Artificial Sequence
<220> FEATURE:
<223> OTHER INFORMATION: synthetic primer

<400> SEQUENCE: 75
gtgggtgggt ggaggtg                                                     17

<210> SEQ ID NO 76
<211> LENGTH: 18
<212> TYPE: DNA
<213> ORGANISM: Artificial Sequence
<220> FEATURE:
<223> OTHER INFORMATION: synthetic primer

<400> SEQUENCE: 76
atgtcctgct gccctgag                                                    18

<210> SEQ ID NO 77
<211> LENGTH: 20
<212> TYPE: DNA
<213> ORGANISM: Artificial Sequence
<220> FEATURE:
<223> OTHER INFORMATION: synthetic primer

<400> SEQUENCE: 77
acctgggaca tcactcaacc                                                  20

<210> SEQ ID NO 78
<211> LENGTH: 17
<212> TYPE: DNA
<213> ORGANISM: Artificial Sequence
<220> FEATURE:
<223> OTHER INFORMATION: synthetic primer
```

<400> SEQUENCE: 78
ctgcaggcta gcagggc                                                        17

<210> SEQ ID NO 79
<211> LENGTH: 19
<212> TYPE: DNA
<213> ORGANISM: Artificial Sequence
<220> FEATURE:
<223> OTHER INFORMATION: synthetic primer

<400> SEQUENCE: 79
atttgcttgc ctgttgctg                                                      19

<210> SEQ ID NO 80
<211> LENGTH: 20
<212> TYPE: DNA
<213> ORGANISM: Artificial Sequence
<220> FEATURE:
<223> OTHER INFORMATION: synthetic primer

<400> SEQUENCE: 80
gttaaaattt cctcccacgg                                                     20

<210> SEQ ID NO 81
<211> LENGTH: 18
<212> TYPE: DNA
<213> ORGANISM: Artificial Sequence
<220> FEATURE:
<223> OTHER INFORMATION: synthetic primer

<400> SEQUENCE: 81
gagtgggcag gtgtggtg                                                       18

<210> SEQ ID NO 82
<211> LENGTH: 17
<212> TYPE: DNA
<213> ORGANISM: Artificial Sequence
<220> FEATURE:
<223> OTHER INFORMATION: synthetic primer

<400> SEQUENCE: 82
cagcagagcc ctcctcc                                                        17

<210> SEQ ID NO 83
<211> LENGTH: 17
<212> TYPE: DNA
<213> ORGANISM: Artificial Sequence
<220> FEATURE:
<223> OTHER INFORMATION: synthetic primer

<400> SEQUENCE: 83
aaggtgaggg caggtgg                                                        17

<210> SEQ ID NO 84
<211> LENGTH: 18
<212> TYPE: DNA
<213> ORGANISM: Artificial Sequence
<220> FEATURE:
<223> OTHER INFORMATION: synthetic primer

<400> SEQUENCE: 84
ttccctggaa ggaaaggc                                                       18

<210> SEQ ID NO 85
<211> LENGTH: 17
<212> TYPE: DNA

-continued

```
<213> ORGANISM: Artificial Sequence
<220> FEATURE:
<223> OTHER INFORMATION: synthetic primer

<400> SEQUENCE: 85
ctccgaaagc ccgtctg                                                        17

<210> SEQ ID NO 86
<211> LENGTH: 19
<212> TYPE: DNA
<213> ORGANISM: Artificial Sequence
<220> FEATURE:
<223> OTHER INFORMATION: synthetic primer

<400> SEQUENCE: 86
gtttccccag ggagtctgg                                                      19

<210> SEQ ID NO 87
<211> LENGTH: 22
<212> TYPE: DNA
<213> ORGANISM: Artificial Sequence
<220> FEATURE:
<223> OTHER INFORMATION: synthetic primer

<400> SEQUENCE: 87
ttttgtttcc tttacccctt tc                                                  22

<210> SEQ ID NO 88
<211> LENGTH: 20
<212> TYPE: DNA
<213> ORGANISM: Artificial Sequence
<220> FEATURE:
<223> OTHER INFORMATION: synthetic primer

<400> SEQUENCE: 88
taaggtgcgt gctttgagag                                                     20

<210> SEQ ID NO 89
<211> LENGTH: 25
<212> TYPE: DNA
<213> ORGANISM: Artificial Sequence
<220> FEATURE:
<223> OTHER INFORMATION: synthetic primer

<400> SEQUENCE: 89
tgttttcagt catgtatatt tgtgg                                               25

<210> SEQ ID NO 90
<211> LENGTH: 24
<212> TYPE: DNA
<213> ORGANISM: Artificial Sequence
<220> FEATURE:
<223> OTHER INFORMATION: synthetic primer

<400> SEQUENCE: 90
tgctcttctg cagtctttat tagc                                                24

<210> SEQ ID NO 91
<211> LENGTH: 19
<212> TYPE: DNA
<213> ORGANISM: Artificial Sequence
<220> FEATURE:
<223> OTHER INFORMATION: synthetic primer

<400> SEQUENCE: 91
tcatgcacca tgactgacg                                                      19
```

<210> SEQ ID NO 92
<211> LENGTH: 20
<212> TYPE: DNA
<213> ORGANISM: Artificial Sequence
<220> FEATURE:
<223> OTHER INFORMATION: synthetic primer

<400> SEQUENCE: 92
tgcggtgagc tgagattatg                                            20

<210> SEQ ID NO 93
<211> LENGTH: 21
<212> TYPE: DNA
<213> ORGANISM: Artificial Sequence
<220> FEATURE:
<223> OTHER INFORMATION: synthetic primer

<400> SEQUENCE: 93
ccttgggcta agaaagccta c                                          21

<210> SEQ ID NO 94
<211> LENGTH: 22
<212> TYPE: DNA
<213> ORGANISM: Artificial Sequence
<220> FEATURE:
<223> OTHER INFORMATION: synthetic primer

<400> SEQUENCE: 94
tgctcatatg caagaaactc tc                                         22

<210> SEQ ID NO 95
<211> LENGTH: 24
<212> TYPE: DNA
<213> ORGANISM: Artificial Sequence
<220> FEATURE:
<223> OTHER INFORMATION: synthetic primer

<400> SEQUENCE: 95
cactgattac ttcatcctgg aaag                                       24

<210> SEQ ID NO 96
<211> LENGTH: 23
<212> TYPE: DNA
<213> ORGANISM: Artificial Sequence
<220> FEATURE:
<223> OTHER INFORMATION: synthetic primer

<400> SEQUENCE: 96
agggttatat tagtgatccc tgc                                        23

<210> SEQ ID NO 97
<211> LENGTH: 23
<212> TYPE: DNA
<213> ORGANISM: Artificial Sequence
<220> FEATURE:
<223> OTHER INFORMATION: synthetic primer

<400> SEQUENCE: 97
tggcataaaa tggaataatt gtc                                        23

<210> SEQ ID NO 98
<211> LENGTH: 21
<212> TYPE: DNA
<213> ORGANISM: Artificial Sequence
<220> FEATURE:
<223> OTHER INFORMATION: synthetic primer

<400> SEQUENCE: 98
aaagcttggc ttcaagttgt c                                    21

<210> SEQ ID NO 99
<211> LENGTH: 22
<212> TYPE: DNA
<213> ORGANISM: Artificial Sequence
<220> FEATURE:
<223> OTHER INFORMATION: synthetic primer

<400> SEQUENCE: 99
tgttacccag aaggtcttga ac                                   22

<210> SEQ ID NO 100
<211> LENGTH: 19
<212> TYPE: DNA
<213> ORGANISM: Artificial Sequence
<220> FEATURE:
<223> OTHER INFORMATION: synthetic primer

<400> SEQUENCE: 100
agtgagggac gggcaatag                                       19

<210> SEQ ID NO 101
<211> LENGTH: 24
<212> TYPE: DNA
<213> ORGANISM: Artificial Sequence
<220> FEATURE:
<223> OTHER INFORMATION: synthetic primer

<400> SEQUENCE: 101
tttgttgtta ctgcatacac attg                                 24

<210> SEQ ID NO 102
<211> LENGTH: 22
<212> TYPE: DNA
<213> ORGANISM: Artificial Sequence
<220> FEATURE:
<223> OTHER INFORMATION: synthetic primer

<400> SEQUENCE: 102
aagcagagac acaagcaaag tc                                   22

<210> SEQ ID NO 103
<211> LENGTH: 23
<212> TYPE: DNA
<213> ORGANISM: Artificial Sequence
<220> FEATURE:
<223> OTHER INFORMATION: synthetic primer

<400> SEQUENCE: 103
aagtcggaaa attcaaatag gac                                  23

<210> SEQ ID NO 104
<211> LENGTH: 20
<212> TYPE: DNA
<213> ORGANISM: Artificial Sequence
<220> FEATURE:
<223> OTHER INFORMATION: synthetic primer

<400> SEQUENCE: 104
ttctccatac aggtcacggg                                      20

<210> SEQ ID NO 105
<211> LENGTH: 25
<212> TYPE: DNA

```
<213> ORGANISM: Artificial Sequence
<220> FEATURE:
<223> OTHER INFORMATION: synthetic primer

<400> SEQUENCE: 105
tgcaaagttt cttctattaa ccaag                                              25

<210> SEQ ID NO 106
<211> LENGTH: 19
<212> TYPE: DNA
<213> ORGANISM: Artificial Sequence
<220> FEATURE:
<223> OTHER INFORMATION: synthetic primer

<400> SEQUENCE: 106
agccccagtg atcttccag                                                     19

<210> SEQ ID NO 107
<211> LENGTH: 27
<212> TYPE: DNA
<213> ORGANISM: Artificial Sequence
<220> FEATURE:
<223> OTHER INFORMATION: synthetic primer

<400> SEQUENCE: 107
aaaaggacct attagatgat tcagatg                                            27

<210> SEQ ID NO 108
<211> LENGTH: 20
<212> TYPE: DNA
<213> ORGANISM: Artificial Sequence
<220> FEATURE:
<223> OTHER INFORMATION: synthetic primer

<400> SEQUENCE: 108
attctgctat gcccaaaggg                                                    20

<210> SEQ ID NO 109
<211> LENGTH: 26
<212> TYPE: DNA
<213> ORGANISM: Artificial Sequence
<220> FEATURE:
<223> OTHER INFORMATION: synthetic primer

<400> SEQUENCE: 109
aataaggaat cagaggctaa agttac                                             26

<210> SEQ ID NO 110
<211> LENGTH: 20
<212> TYPE: DNA
<213> ORGANISM: Artificial Sequence
<220> FEATURE:
<223> OTHER INFORMATION: synthetic primer

<400> SEQUENCE: 110
gatgacctgt tgcaggaatg                                                    20

<210> SEQ ID NO 111
<211> LENGTH: 25
<212> TYPE: DNA
<213> ORGANISM: Artificial Sequence
<220> FEATURE:
<223> OTHER INFORMATION: synthetic primer

<400> SEQUENCE: 111
aaagtttgat tactggaaaa gttcg                                              25
```

<210> SEQ ID NO 112
<211> LENGTH: 23
<212> TYPE: DNA
<213> ORGANISM: Artificial Sequence
<220> FEATURE:
<223> OTHER INFORMATION: synthetic primer

<400> SEQUENCE: 112
tcaactaagt cctcaggttc tgg                                              23

<210> SEQ ID NO 113
<211> LENGTH: 21
<212> TYPE: DNA
<213> ORGANISM: Artificial Sequence
<220> FEATURE:
<223> OTHER INFORMATION: synthetic primer

<400> SEQUENCE: 113
ctcccaccta atctcagtcc c                                                21

<210> SEQ ID NO 114
<211> LENGTH: 20
<212> TYPE: DNA
<213> ORGANISM: Artificial Sequence
<220> FEATURE:
<223> OTHER INFORMATION: synthetic primer

<400> SEQUENCE: 114
ttatcaaatg gcacctgctg                                                  20

<210> SEQ ID NO 115
<211> LENGTH: 17
<212> TYPE: DNA
<213> ORGANISM: Artificial Sequence
<220> FEATURE:
<223> OTHER INFORMATION: synthetic primer

<400> SEQUENCE: 115
cccctgactc cgtccag                                                     17

<210> SEQ ID NO 116
<211> LENGTH: 43
<212> TYPE: DNA
<213> ORGANISM: Artificial Sequence
<220> FEATURE:
<223> OTHER INFORMATION: synthetic primer

<400> SEQUENCE: 116
gcggcaggca guaacauuaa gcguuuaugc uacuucugaa uug                        43

<210> SEQ ID NO 117
<211> LENGTH: 43
<212> TYPE: DNA
<213> ORGANISM: Artificial Sequence
<220> FEATURE:
<223> OTHER INFORMATION: synthetic primer

<400> SEQUENCE: 117
gguaugcaca aucacuugga accgcugaau aaaugacuuu ugc                        43

<210> SEQ ID NO 118
<211> LENGTH: 48
<212> TYPE: DNA
<213> ORGANISM: Artificial Sequence
<220> FEATURE:
<223> OTHER INFORMATION: synthetic primer

<400> SEQUENCE: 118
gguagggcuu uguuuucugu uucccaucu uuauaguugu gcauuauc        48

<210> SEQ ID NO 119
<211> LENGTH: 41
<212> TYPE: DNA
<213> ORGANISM: Artificial Sequence
<220> FEATURE:
<223> OTHER INFORMATION: synthetic primer

<400> SEQUENCE: 119
cgcacaaaca caggcuuuaa uuggcagaua gcacugaaau g        41

<210> SEQ ID NO 120
<211> LENGTH: 44
<212> TYPE: DNA
<213> ORGANISM: Artificial Sequence
<220> FEATURE:
<223> OTHER INFORMATION: synthetic primer

<400> SEQUENCE: 120
caagguuaug uuucccaug uacaugugga gugcaaguga aagc        44

<210> SEQ ID NO 121
<211> LENGTH: 45
<212> TYPE: DNA
<213> ORGANISM: Artificial Sequence
<220> FEATURE:
<223> OTHER INFORMATION: synthetic primer

<400> SEQUENCE: 121
ggguggaagg aauggaaaag aauucauacu acaugcuccu gacac        45

<210> SEQ ID NO 122
<211> LENGTH: 45
<212> TYPE: DNA
<213> ORGANISM: Artificial Sequence
<220> FEATURE:
<223> OTHER INFORMATION: synthetic primer

<400> SEQUENCE: 122
gaauugguaa aaucuguucu ucuguuccaa gccaccuuuc cuaac        45

<210> SEQ ID NO 123
<211> LENGTH: 44
<212> TYPE: DNA
<213> ORGANISM: Artificial Sequence
<220> FEATURE:
<223> OTHER INFORMATION: synthetic primer

<400> SEQUENCE: 123
gguggacuac aaaauacaau ccugaggaug ggaagagauc accc        44

<210> SEQ ID NO 124
<211> LENGTH: 37
<212> TYPE: DNA
<213> ORGANISM: Artificial Sequence
<220> FEATURE:
<223> OTHER INFORMATION: synthetic primer

<400> SEQUENCE: 124
gcggaaacga ggaaaguuuc caucuggccc gcacauc        37

<210> SEQ ID NO 125
<211> LENGTH: 40
<212> TYPE: DNA

```
<213> ORGANISM: Artificial Sequence
<220> FEATURE:
<223> OTHER INFORMATION: synthetic primer

<400> SEQUENCE: 125
ccuguuccau uucccuuucc uucaggaauu cauuggcagg                                40

<210> SEQ ID NO 126
<211> LENGTH: 39
<212> TYPE: DNA
<213> ORGANISM: Artificial Sequence
<220> FEATURE:
<223> OTHER INFORMATION: synthetic primer

<400> SEQUENCE: 126
cuccuguggu ggauugcauu uccagauugc cuuucuguc                                 39

<210> SEQ ID NO 127
<211> LENGTH: 21
<212> TYPE: DNA
<213> ORGANISM: Artificial Sequence
<220> FEATURE:
<223> OTHER INFORMATION: synthetic primer

<400> SEQUENCE: 127
agaggtgatt tgtgttcctg c                                                   21

<210> SEQ ID NO 128
<211> LENGTH: 20
<212> TYPE: DNA
<213> ORGANISM: Artificial Sequence
<220> FEATURE:
<223> OTHER INFORMATION: synthetic primer

<400> SEQUENCE: 128
tatcatttgg ctttccccac                                                     20

<210> SEQ ID NO 129
<211> LENGTH: 24
<212> TYPE: DNA
<213> ORGANISM: Artificial Sequence
<220> FEATURE:
<223> OTHER INFORMATION: synthetic primer

<400> SEQUENCE: 129
tctccaaaat atatgccaaa gaag                                                24

<210> SEQ ID NO 130
<211> LENGTH: 19
<212> TYPE: DNA
<213> ORGANISM: Artificial Sequence
<220> FEATURE:
<223> OTHER INFORMATION: synthetic primer

<400> SEQUENCE: 130
ggccatggaa tctgtcagc                                                      19

<210> SEQ ID NO 131
<211> LENGTH: 18
<212> TYPE: DNA
<213> ORGANISM: Artificial Sequence
<220> FEATURE:
<223> OTHER INFORMATION: synthetic primer

<400> SEQUENCE: 131
tttccagcat ggtgaggg                                                       18
```

<210> SEQ ID NO 132
<211> LENGTH: 20
<212> TYPE: DNA
<213> ORGANISM: Artificial Sequence
<220> FEATURE:
<223> OTHER INFORMATION: synthetic primer

<400> SEQUENCE: 132
agcatgtggc accatctcac                                               20

<210> SEQ ID NO 133
<211> LENGTH: 18
<212> TYPE: DNA
<213> ORGANISM: Artificial Sequence
<220> FEATURE:
<223> OTHER INFORMATION: synthetic primer

<400> SEQUENCE: 133
catgtgcccc tccttctg                                                 18

<210> SEQ ID NO 134
<211> LENGTH: 19
<212> TYPE: DNA
<213> ORGANISM: Artificial Sequence
<220> FEATURE:
<223> OTHER INFORMATION: synthetic primer

<400> SEQUENCE: 134
aattcggatg cagagcttc                                                19

<210> SEQ ID NO 135
<211> LENGTH: 20
<212> TYPE: DNA
<213> ORGANISM: Artificial Sequence
<220> FEATURE:
<223> OTHER INFORMATION: synthetic primer

<400> SEQUENCE: 135
tcgtctgtgt gtgtcactcg                                               20

<210> SEQ ID NO 136
<211> LENGTH: 20
<212> TYPE: DNA
<213> ORGANISM: Artificial Sequence
<220> FEATURE:
<223> OTHER INFORMATION: synthetic primer

<400> SEQUENCE: 136
gcaagggatt gtgattgttc                                               20

<210> SEQ ID NO 137
<211> LENGTH: 22
<212> TYPE: DNA
<213> ORGANISM: Artificial Sequence
<220> FEATURE:
<223> OTHER INFORMATION: synthetic primer

<400> SEQUENCE: 137
gcaatgccat ctttatcatt tc                                            22

<210> SEQ ID NO 138
<211> LENGTH: 20
<212> TYPE: DNA
<213> ORGANISM: Artificial Sequence
<220> FEATURE:
<223> OTHER INFORMATION: synthetic primer

```
<400> SEQUENCE: 138 agaccctgc tcctatagcc                                              20

<210> SEQ ID NO 139
<211> LENGTH: 20
<212> TYPE: DNA
<213> ORGANISM: Artificial Sequence
<220> FEATURE:
<223> OTHER INFORMATION: synthetic primer

<400> SEQUENCE: 139
cctgcattca ggaaaagtgg                                             20

<210> SEQ ID NO 140
<211> LENGTH: 20
<212> TYPE: DNA
<213> ORGANISM: Artificial Sequence
<220> FEATURE:
<223> OTHER INFORMATION: synthetic primer

<400> SEQUENCE: 140
ttgcaaacac tgaagttggg                                             20

<210> SEQ ID NO 141
<211> LENGTH: 18
<212> TYPE: DNA
<213> ORGANISM: Artificial Sequence
<220> FEATURE:
<223> OTHER INFORMATION: synthetic primer

<400> SEQUENCE: 141
atcctgcatg ggatggtg                                               18

<210> SEQ ID NO 142
<211> LENGTH: 21
<212> TYPE: DNA
<213> ORGANISM: Artificial Sequence
<220> FEATURE:
<223> OTHER INFORMATION: synthetic primer

<400> SEQUENCE: 142
agatctgtgt tgggtgacca g                                           21

<210> SEQ ID NO 143
<211> LENGTH: 21
<212> TYPE: DNA
<213> ORGANISM: Artificial Sequence
<220> FEATURE:
<223> OTHER INFORMATION: synthetic primer

<400> SEQUENCE: 143
cactcccacc accacagtta g                                           21

<210> SEQ ID NO 144
<211> LENGTH: 20
<212> TYPE: DNA
<213> ORGANISM: Artificial Sequence
<220> FEATURE:
<223> OTHER INFORMATION: synthetic primer

<400> SEQUENCE: 144
agtctgcgta ctttcctggc                                             20

<210> SEQ ID NO 145
<211> LENGTH: 22
<212> TYPE: DNA
```

```
<213> ORGANISM: Artificial Sequence
<220> FEATURE:
<223> OTHER INFORMATION: synthetic primer

<400> SEQUENCE: 145
tcctgagaga acaaaactct gg                                              22

<210> SEQ ID NO 146
<211> LENGTH: 19
<212> TYPE: DNA
<213> ORGANISM: Artificial Sequence
<220> FEATURE:
<223> OTHER INFORMATION: synthetic primer

<400> SEQUENCE: 146
atgggatggg cctgtattc                                                  19

<210> SEQ ID NO 147
<211> LENGTH: 20
<212> TYPE: DNA
<213> ORGANISM: Artificial Sequence
<220> FEATURE:
<223> OTHER INFORMATION: synthetic primer

<400> SEQUENCE: 147
gtagaatcca cagtgcccag                                                 20

<210> SEQ ID NO 148
<211> LENGTH: 24
<212> TYPE: DNA
<213> ORGANISM: Artificial Sequence
<220> FEATURE:
<223> OTHER INFORMATION: synthetic primer

<400> SEQUENCE: 148
gctttatagg acctttgact gttg                                            24

<210> SEQ ID NO 149
<211> LENGTH: 20
<212> TYPE: DNA
<213> ORGANISM: Artificial Sequence
<220> FEATURE:
<223> OTHER INFORMATION: synthetic primer

<400> SEQUENCE: 149
caaggtgatt ttgaggtggg                                                 20

<210> SEQ ID NO 150
<211> LENGTH: 22
<212> TYPE: DNA
<213> ORGANISM: Artificial Sequence
<220> FEATURE:
<223> OTHER INFORMATION: synthetic primer

<400> SEQUENCE: 150
gagaaagctg tttcttccca ag                                              22

<210> SEQ ID NO 151
<211> LENGTH: 21
<212> TYPE: DNA
<213> ORGANISM: Artificial Sequence
<220> FEATURE:
<223> OTHER INFORMATION: synthetic primer

<400> SEQUENCE: 151
caagctgcag acctacctgt c                                               21
```

```
<210> SEQ ID NO 152
<211> LENGTH: 20
<212> TYPE: DNA
<213> ORGANISM: Artificial Sequence
<220> FEATURE:
<223> OTHER INFORMATION: synthetic primer

<400> SEQUENCE: 152
tggaggtaga agctgggaag                                              20

<210> SEQ ID NO 153
<211> LENGTH: 23
<212> TYPE: DNA
<213> ORGANISM: Artificial Sequence
<220> FEATURE:
<223> OTHER INFORMATION: synthetic primer

<400> SEQUENCE: 153
ttttctgttg gacacagtct ctc                                          23

<210> SEQ ID NO 154
<211> LENGTH: 23
<212> TYPE: DNA
<213> ORGANISM: Artificial Sequence
<220> FEATURE:
<223> OTHER INFORMATION: synthetic primer

<400> SEQUENCE: 154
ttatgactga gatggtctct tgg                                          23

<210> SEQ ID NO 155
<211> LENGTH: 17
<212> TYPE: DNA
<213> ORGANISM: Artificial Sequence
<220> FEATURE:
<223> OTHER INFORMATION: synthetic primer

<400> SEQUENCE: 155
cccggcctcc aaaatac                                                 17

<210> SEQ ID NO 156
<211> LENGTH: 24
<212> TYPE: DNA
<213> ORGANISM: Artificial Sequence
<220> FEATURE:
<223> OTHER INFORMATION: synthetic primer

<400> SEQUENCE: 156
gaaacctctt ttcttcttac agcc                                         24

<210> SEQ ID NO 157
<211> LENGTH: 20
<212> TYPE: DNA
<213> ORGANISM: Artificial Sequence
<220> FEATURE:
<223> OTHER INFORMATION: synthetic primer

<400> SEQUENCE: 157
gcaagggctc tgtgagtgag                                              20

<210> SEQ ID NO 158
<211> LENGTH: 20
<212> TYPE: DNA
<213> ORGANISM: Artificial Sequence
<220> FEATURE:
<223> OTHER INFORMATION: synthetic primer
```

```
<400> SEQUENCE: 158
taaccatgct ctgcctgaag                                                   20

<210> SEQ ID NO 159
<211> LENGTH: 20
<212> TYPE: DNA
<213> ORGANISM: Artificial Sequence
<220> FEATURE:
<223> OTHER INFORMATION: synthetic primer

<400> SEQUENCE: 159
agcttaaggt aagcctgggg                                                   20

<210> SEQ ID NO 160
<211> LENGTH: 21
<212> TYPE: DNA
<213> ORGANISM: Artificial Sequence
<220> FEATURE:
<223> OTHER INFORMATION: synthetic primer

<400> SEQUENCE: 160
cttttctggc catcttgatt c                                                 21

<210> SEQ ID NO 161
<211> LENGTH: 23
<212> TYPE: DNA
<213> ORGANISM: Artificial Sequence
<220> FEATURE:
<223> OTHER INFORMATION: synthetic primer

<400> SEQUENCE: 161
tgtccttaga tacttgggac ctg                                               23

<210> SEQ ID NO 162
<211> LENGTH: 20
<212> TYPE: DNA
<213> ORGANISM: Artificial Sequence
<220> FEATURE:
<223> OTHER INFORMATION: synthetic primer

<400> SEQUENCE: 162
ccctcagtca cgtctcttcc                                                   20

<210> SEQ ID NO 163
<211> LENGTH: 25
<212> TYPE: DNA
<213> ORGANISM: Artificial Sequence
<220> FEATURE:
<223> OTHER INFORMATION: synthetic primer

<400> SEQUENCE: 163
cccagaagaa atggtcataa tgtag                                             25

<210> SEQ ID NO 164
<211> LENGTH: 20
<212> TYPE: DNA
<213> ORGANISM: Artificial Sequence
<220> FEATURE:
<223> OTHER INFORMATION: synthetic primer

<400> SEQUENCE: 164
tctaccaggt ctgcacctcc                                                   20

<210> SEQ ID NO 165
<211> LENGTH: 21
<212> TYPE: DNA
```

```
<213> ORGANISM: Artificial Sequence
<220> FEATURE:
<223> OTHER INFORMATION: synthetic primer

<400> SEQUENCE: 165
aggggaattt tatcgtgaaa g                                              21

<210> SEQ ID NO 166
<211> LENGTH: 20
<212> TYPE: DNA
<213> ORGANISM: Artificial Sequence
<220> FEATURE:
<223> OTHER INFORMATION: synthetic primer

<400> SEQUENCE: 166
aggtgtgact ttgaggcagc                                                20

<210> SEQ ID NO 167
<211> LENGTH: 20
<212> TYPE: DNA
<213> ORGANISM: Artificial Sequence
<220> FEATURE:
<223> OTHER INFORMATION: synthetic primer

<400> SEQUENCE: 167
cccacatctc ctaccctcag                                                20

<210> SEQ ID NO 168
<211> LENGTH: 20
<212> TYPE: DNA
<213> ORGANISM: Artificial Sequence
<220> FEATURE:
<223> OTHER INFORMATION: synthetic primer

<400> SEQUENCE: 168
gcgtacagca gcacattagg                                                20

<210> SEQ ID NO 169
<211> LENGTH: 19
<212> TYPE: DNA
<213> ORGANISM: Artificial Sequence
<220> FEATURE:
<223> OTHER INFORMATION: synthetic primer

<400> SEQUENCE: 169
gggcaggaga ggaagattg                                                 19

<210> SEQ ID NO 170
<211> LENGTH: 19
<212> TYPE: DNA
<213> ORGANISM: Artificial Sequence
<220> FEATURE:
<223> OTHER INFORMATION: synthetic primer

<400> SEQUENCE: 170
ctgcctttag cccaaccag                                                 19

<210> SEQ ID NO 171
<211> LENGTH: 20
<212> TYPE: DNA
<213> ORGANISM: Artificial Sequence
<220> FEATURE:
<223> OTHER INFORMATION: synthetic primer

<400> SEQUENCE: 171
ctgtagctag ttggggtgcc                                                20
```

<210> SEQ ID NO 172
<211> LENGTH: 20
<212> TYPE: DNA
<213> ORGANISM: Artificial Sequence
<220> FEATURE:
<223> OTHER INFORMATION: synthetic primer

<400> SEQUENCE: 172
acagagcaag actctgccac                                              20

<210> SEQ ID NO 173
<211> LENGTH: 20
<212> TYPE: DNA
<213> ORGANISM: Artificial Sequence
<220> FEATURE:
<223> OTHER INFORMATION: synthetic primer

<400> SEQUENCE: 173
gaacggtagc tcccttcctc                                              20

<210> SEQ ID NO 174
<211> LENGTH: 20
<212> TYPE: DNA
<213> ORGANISM: Artificial Sequence
<220> FEATURE:
<223> OTHER INFORMATION: synthetic primer

<400> SEQUENCE: 174
ttaggagggc tgttttgagg                                              20

<210> SEQ ID NO 175
<211> LENGTH: 20
<212> TYPE: DNA
<213> ORGANISM: Artificial Sequence
<220> FEATURE:
<223> OTHER INFORMATION: synthetic primer

<400> SEQUENCE: 175
gttcctcagc atcgaccttg                                              20

<210> SEQ ID NO 176
<211> LENGTH: 22
<212> TYPE: DNA
<213> ORGANISM: Artificial Sequence
<220> FEATURE:
<223> OTHER INFORMATION: synthetic primer

<400> SEQUENCE: 176 ccacccttttg aagtaggtac ag                                          22

<210> SEQ ID NO 177
<211> LENGTH: 20
<212> TYPE: DNA
<213> ORGANISM: Artificial Sequence
<220> FEATURE:
<223> OTHER INFORMATION: synthetic primer

<400> SEQUENCE: 177
ctgccagctc tcttctcagg                                              20

<210> SEQ ID NO 178
<211> LENGTH: 20
<212> TYPE: DNA
<213> ORGANISM: Artificial Sequence
<220> FEATURE:
<223> OTHER INFORMATION: synthetic primer

<400> SEQUENCE: 178
ataccagctc ttccccaacc					20

<210> SEQ ID NO 179
<211> LENGTH: 22
<212> TYPE: DNA
<213> ORGANISM: Artificial Sequence
<220> FEATURE:
<223> OTHER INFORMATION: synthetic primer

<400> SEQUENCE: 179
ttcctctgac tgctggaaat ag				22

<210> SEQ ID NO 180
<211> LENGTH: 20
<212> TYPE: DNA
<213> ORGANISM: Artificial Sequence
<220> FEATURE:
<223> OTHER INFORMATION: synthetic primer

<400> SEQUENCE: 180
atatctgcag tcagcctggg					20

<210> SEQ ID NO 181
<211> LENGTH: 20
<212> TYPE: DNA
<213> ORGANISM: Artificial Sequence
<220> FEATURE:
<223> OTHER INFORMATION: synthetic primer

<400> SEQUENCE: 181
gcgtttaaat tcttccctgg					20

<210> SEQ ID NO 182
<211> LENGTH: 20
<212> TYPE: DNA
<213> ORGANISM: Artificial Sequence
<220> FEATURE:
<223> OTHER INFORMATION: synthetic primer

<400> SEQUENCE: 182
cagctgaaga gctgaggacc					20

<210> SEQ ID NO 183
<211> LENGTH: 20
<212> TYPE: DNA
<213> ORGANISM: Artificial Sequence
<220> FEATURE:
<223> OTHER INFORMATION: synthetic primer

<400> SEQUENCE: 183
tctgcctgtg ttctgagctg					20

<210> SEQ ID NO 184
<211> LENGTH: 20
<212> TYPE: DNA
<213> ORGANISM: Artificial Sequence
<220> FEATURE:
<223> OTHER INFORMATION: synthetic primer

<400> SEQUENCE: 184
accccaagcc ttgtttcttc					20

<210> SEQ ID NO 185
<211> LENGTH: 22
<212> TYPE: DNA

```
<213> ORGANISM: Artificial Sequence
<220> FEATURE:
<223> OTHER INFORMATION: synthetic primer

<400> SEQUENCE: 185
ctcggtctca aaagtacaaa cc                                              22

<210> SEQ ID NO 186
<211> LENGTH: 22
<212> TYPE: DNA
<213> ORGANISM: Artificial Sequence
<220> FEATURE:
<223> OTHER INFORMATION: synthetic primer

<400> SEQUENCE: 186
cgtttgccaa ctcctagctt ac                                              22

<210> SEQ ID NO 187
<211> LENGTH: 19
<212> TYPE: DNA
<213> ORGANISM: Artificial Sequence
<220> FEATURE:
<223> OTHER INFORMATION: synthetic primer

<400> SEQUENCE: 187
agaggaaagc cacctgctc                                                  19

<210> SEQ ID NO 188
<211> LENGTH: 20
<212> TYPE: DNA
<213> ORGANISM: Artificial Sequence
<220> FEATURE:
<223> OTHER INFORMATION: synthetic primer

<400> SEQUENCE: 188
acatggcctg tgtctgcttc                                                 20

<210> SEQ ID NO 189
<211> LENGTH: 25
<212> TYPE: DNA
<213> ORGANISM: Artificial Sequence
<220> FEATURE:
<223> OTHER INFORMATION: synthetic primer

<400> SEQUENCE: 189
gactggaaga aaataaccaa gtttc                                           25

<210> SEQ ID NO 190
<211> LENGTH: 20
<212> TYPE: DNA
<213> ORGANISM: Artificial Sequence
<220> FEATURE:
<223> OTHER INFORMATION: synthetic primer

<400> SEQUENCE: 190
atgctaacac caacagtggc                                                 20

<210> SEQ ID NO 191
<211> LENGTH: 20
<212> TYPE: DNA
<213> ORGANISM: Artificial Sequence
<220> FEATURE:
<223> OTHER INFORMATION: synthetic primer

<400> SEQUENCE: 191
agggaacaag aagtgcatcg                                                 20
```

```
<210> SEQ ID NO 192
<211> LENGTH: 25
<212> TYPE: DNA
<213> ORGANISM: Artificial Sequence
<220> FEATURE:
<223> OTHER INFORMATION: synthetic primer

<400> SEQUENCE: 192
ttaaaaggta ctggtggagt atttg                                         25

<210> SEQ ID NO 193
<211> LENGTH: 20
<212> TYPE: DNA
<213> ORGANISM: Artificial Sequence
<220> FEATURE:
<223> OTHER INFORMATION: synthetic primer

<400> SEQUENCE: 193
tctttggagc aggaacaatg                                               20

<210> SEQ ID NO 194
<211> LENGTH: 21
<212> TYPE: DNA
<213> ORGANISM: Artificial Sequence
<220> FEATURE:
<223> OTHER INFORMATION: synthetic primer

<400> SEQUENCE: 194
agaaggaagg aaaatttggt g                                             21

<210> SEQ ID NO 195
<211> LENGTH: 21
<212> TYPE: DNA
<213> ORGANISM: Artificial Sequence
<220> FEATURE:
<223> OTHER INFORMATION: synthetic primer

<400> SEQUENCE: 195
aacttcttgc acatggcttt c                                             21

<210> SEQ ID NO 196
<211> LENGTH: 20
<212> TYPE: DNA
<213> ORGANISM: Artificial Sequence
<220> FEATURE:
<223> OTHER INFORMATION: synthetic primer

<400> SEQUENCE: 196
cctagggctg tgctgttttg                                               20

<210> SEQ ID NO 197
<211> LENGTH: 22
<212> TYPE: DNA
<213> ORGANISM: Artificial Sequence
<220> FEATURE:
<223> OTHER INFORMATION: synthetic primer

<400> SEQUENCE: 197
tggttaaatt cctttgaagt gc                                            22

<210> SEQ ID NO 198
<211> LENGTH: 23
<212> TYPE: DNA
<213> ORGANISM: Artificial Sequence
<220> FEATURE:
<223> OTHER INFORMATION: synthetic primer
```

```
<400> SEQUENCE: 198
tgccatatat cttggcattt atc                                          23

<210> SEQ ID NO 199
<211> LENGTH: 22
<212> TYPE: DNA
<213> ORGANISM: Artificial Sequence
<220> FEATURE:
<223> OTHER INFORMATION: synthetic primer

<400> SEQUENCE: 199
aaatggaagc atttgggaat ac                                           22

<210> SEQ ID NO 200
<211> LENGTH: 20
<212> TYPE: DNA
<213> ORGANISM: Artificial Sequence
<220> FEATURE:
<223> OTHER INFORMATION: synthetic primer

<400> SEQUENCE: 200
tgcatggttt gtgcatacag                                              20

<210> SEQ ID NO 201
<211> LENGTH: 25
<212> TYPE: DNA
<213> ORGANISM: Artificial Sequence
<220> FEATURE:
<223> OTHER INFORMATION: synthetic primer

<400> SEQUENCE: 201
caaattccac atatttctgg ctaac                                        25

<210> SEQ ID NO 202
<211> LENGTH: 25
<212> TYPE: DNA
<213> ORGANISM: Artificial Sequence
<220> FEATURE:
<223> OTHER INFORMATION: synthetic primer

<400> SEQUENCE: 202
attttcatct taattacgaa tctgc                                        25

<210> SEQ ID NO 203
<211> LENGTH: 25
<212> TYPE: DNA
<213> ORGANISM: Artificial Sequence
<220> FEATURE:
<223> OTHER INFORMATION: synthetic primer

<400> SEQUENCE: 203
aaagcttttc taaaatgcct aatcc                                        25

<210> SEQ ID NO 204
<211> LENGTH: 20
<212> TYPE: DNA
<213> ORGANISM: Artificial Sequence
<220> FEATURE:
<223> OTHER INFORMATION: synthetic primer

<400> SEQUENCE: 204
aacattatat cagtgcgggg                                              20

<210> SEQ ID NO 205
<211> LENGTH: 20
<212> TYPE: DNA
```

```
<213> ORGANISM: Artificial Sequence
<220> FEATURE:
<223> OTHER INFORMATION: synthetic primer

<400> SEQUENCE: 205
ttgcttgaat ctgggaggtg                                          20

<210> SEQ ID NO 206
<211> LENGTH: 20
<212> TYPE: DNA
<213> ORGANISM: Artificial Sequence
<220> FEATURE:
<223> OTHER INFORMATION: synthetic primer

<400> SEQUENCE: 206
ataagccatt tgggttcgtg                                          20

<210> SEQ ID NO 207
<211> LENGTH: 26
<212> TYPE: DNA
<213> ORGANISM: Artificial Sequence
<220> FEATURE:
<223> OTHER INFORMATION: synthetic primer

<400> SEQUENCE: 207
tggttactgt cacaaaataa aacttg                                   26

<210> SEQ ID NO 208
<211> LENGTH: 22
<212> TYPE: DNA
<213> ORGANISM: Artificial Sequence
<220> FEATURE:
<223> OTHER INFORMATION: synthetic primer

<400> SEQUENCE: 208
ggtgacagag taagaccttg cc                                       22

<210> SEQ ID NO 209
<211> LENGTH: 23
<212> TYPE: DNA
<213> ORGANISM: Artificial Sequence
<220> FEATURE:
<223> OTHER INFORMATION: synthetic primer

<400> SEQUENCE: 209
tttatacccg attttctcca ctg                                      23

<210> SEQ ID NO 210
<211> LENGTH: 22
<212> TYPE: DNA
<213> ORGANISM: Artificial Sequence
<220> FEATURE:
<223> OTHER INFORMATION: synthetic primer

<400> SEQUENCE: 210
cattttatgg tgttggtgtt gg                                       22

<210> SEQ ID NO 211
<211> LENGTH: 24
<212> TYPE: DNA
<213> ORGANISM: Artificial Sequence
<220> FEATURE:
<223> OTHER INFORMATION: synthetic primer

<400> SEQUENCE: 211
tgaagtgtaa gaggttgatt ttcc                                     24
```

<210> SEQ ID NO 212
<211> LENGTH: 22
<212> TYPE: DNA
<213> ORGANISM: Artificial Sequence
<220> FEATURE:
<223> OTHER INFORMATION: synthetic primer

<400> SEQUENCE: 212
caaaggatca aaattgcttc ag                                          22

<210> SEQ ID NO 213
<211> LENGTH: 22
<212> TYPE: DNA
<213> ORGANISM: Artificial Sequence
<220> FEATURE:
<223> OTHER INFORMATION: synthetic primer

<400> SEQUENCE: 213
ctgagttggt aggattgtga gg                                          22

<210> SEQ ID NO 214
<211> LENGTH: 23
<212> TYPE: DNA
<213> ORGANISM: Artificial Sequence
<220> FEATURE:
<223> OTHER INFORMATION: synthetic primer

<400> SEQUENCE: 214
gcgtttatgc tacttctgaa ttg                                         23

<210> SEQ ID NO 215
<211> LENGTH: 22
<212> TYPE: DNA
<213> ORGANISM: Artificial Sequence
<220> FEATURE:
<223> OTHER INFORMATION: synthetic primer

<400> SEQUENCE: 215
ccgctgaata aatgactttt gc                                          22

<210> SEQ ID NO 216
<211> LENGTH: 25
<212> TYPE: DNA
<213> ORGANISM: Artificial Sequence
<220> FEATURE:
<223> OTHER INFORMATION: synthetic primer

<400> SEQUENCE: 216
cccatcttta tagttgtgca ttatc                                       25

<210> SEQ ID NO 217
<211> LENGTH: 21
<212> TYPE: DNA
<213> ORGANISM: Artificial Sequence
<220> FEATURE:
<223> OTHER INFORMATION: synthetic primer

<400> SEQUENCE: 217
ttggcagata gcactgaaat g                                           21

<210> SEQ ID NO 218
<211> LENGTH: 20
<212> TYPE: DNA
<213> ORGANISM: Artificial Sequence
<220> FEATURE:
<223> OTHER INFORMATION: synthetic primer

```
<400> SEQUENCE: 218
tgtggagtgc aagtgaaagc                                               20

<210> SEQ ID NO 219
<211> LENGTH: 26
<212> TYPE: DNA
<213> ORGANISM: Artificial Sequence
<220> FEATURE:
<223> OTHER INFORMATION: synthetic primer

<400> SEQUENCE: 219
gaattcatac tacatgctcc tgacac                                        26

<210> SEQ ID NO 220
<211> LENGTH: 20
<212> TYPE: DNA
<213> ORGANISM: Artificial Sequence
<220> FEATURE:
<223> OTHER INFORMATION: synthetic primer

<400> SEQUENCE: 220
tccaagccac ctttcctaac                                               20

<210> SEQ ID NO 221
<211> LENGTH: 20
<212> TYPE: DNA
<213> ORGANISM: Artificial Sequence
<220> FEATURE:
<223> OTHER INFORMATION: synthetic primer

<400> SEQUENCE: 221
aggatgggaa gagatcaccc                                               20

<210> SEQ ID NO 222
<211> LENGTH: 17
<212> TYPE: DNA
<213> ORGANISM: Artificial Sequence
<220> FEATURE:
<223> OTHER INFORMATION: synthetic primer

<400> SEQUENCE: 222
catctggccc gcacatc                                                  17

<210> SEQ ID NO 223
<211> LENGTH: 20
<212> TYPE: DNA
<213> ORGANISM: Artificial Sequence
<220> FEATURE:
<223> OTHER INFORMATION: synthetic primer

<400> SEQUENCE: 223
ttcaggaatt cattggcagg                                               20

<210> SEQ ID NO 224
<211> LENGTH: 20
<212> TYPE: DNA
<213> ORGANISM: Artificial Sequence
<220> FEATURE:
<223> OTHER INFORMATION: synthetic primer

<400> SEQUENCE: 224
ttccagattg cctttctgtc                                               20

<210> SEQ ID NO 225
<211> LENGTH: 20
<212> TYPE: DNA
```

```
<213> ORGANISM: Artificial Sequence
<220> FEATURE:
<223> OTHER INFORMATION: synthetic primer

<400> SEQUENCE: 225
gcatgaaccc acttcctgac                                          20

<210> SEQ ID NO 226
<211> LENGTH: 21
<212> TYPE: DNA
<213> ORGANISM: Artificial Sequence
<220> FEATURE:
<223> OTHER INFORMATION: synthetic primer

<400> SEQUENCE: 226
agagcagttt gagacagtgg c                                        21

<210> SEQ ID NO 227
<211> LENGTH: 17
<212> TYPE: DNA
<213> ORGANISM: Artificial Sequence
<220> FEATURE:
<223> OTHER INFORMATION: synthetic primer

<400> SEQUENCE: 227
tctgcacgtg tcagggg                                             17

<210> SEQ ID NO 228
<211> LENGTH: 19
<212> TYPE: DNA
<213> ORGANISM: Artificial Sequence
<220> FEATURE:
<223> OTHER INFORMATION: synthetic primer

<400> SEQUENCE: 228
catgctcatt tcctttggc                                           19

<210> SEQ ID NO 229
<211> LENGTH: 20
<212> TYPE: DNA
<213> ORGANISM: Artificial Sequence
<220> FEATURE:
<223> OTHER INFORMATION: synthetic primer

<400> SEQUENCE: 229
tagcaacaag gtcagcaggc                                          20

<210> SEQ ID NO 230
<211> LENGTH: 20
<212> TYPE: DNA
<213> ORGANISM: Artificial Sequence
<220> FEATURE:
<223> OTHER INFORMATION: synthetic primer

<400> SEQUENCE: 230
atgctggatc cccactttc                                           20

<210> SEQ ID NO 231
<211> LENGTH: 17
<212> TYPE: DNA
<213> ORGANISM: Artificial Sequence
<220> FEATURE:
<223> OTHER INFORMATION: synthetic primer

<400> SEQUENCE: 231
gacaagggtt gggctgg                                             17
```

```
<210> SEQ ID NO 232
<211> LENGTH: 18
<212> TYPE: DNA
<213> ORGANISM: Artificial Sequence
<220> FEATURE:
<223> OTHER INFORMATION: synthetic primer

<400> SEQUENCE: 232
tctttgctgc cgtcttcc                                                     18

<210> SEQ ID NO 233
<211> LENGTH: 18
<212> TYPE: DNA
<213> ORGANISM: Artificial Sequence
<220> FEATURE:
<223> OTHER INFORMATION: synthetic primer

<400> SEQUENCE: 233
tgcttgccac aggtctcc                                                     18

<210> SEQ ID NO 234
<211> LENGTH: 22
<212> TYPE: DNA
<213> ORGANISM: Artificial Sequence
<220> FEATURE:
<223> OTHER INFORMATION: synthetic primer

<400> SEQUENCE: 234
ggacaggtag gacctgattt cc                                                22

<210> SEQ ID NO 235
<211> LENGTH: 25
<212> TYPE: DNA
<213> ORGANISM: Artificial Sequence
<220> FEATURE:
<223> OTHER INFORMATION: synthetic primer

<400> SEQUENCE: 235
aacttgaacc atcttttaac tcagg                                             25

<210> SEQ ID NO 236
<211> LENGTH: 18
<212> TYPE: DNA
<213> ORGANISM: Artificial Sequence
<220> FEATURE:
<223> OTHER INFORMATION: synthetic primer

<400> SEQUENCE: 236
aggggcacag accctctc                                                     18

<210> SEQ ID NO 237
<211> LENGTH: 20
<212> TYPE: DNA
<213> ORGANISM: Artificial Sequence
<220> FEATURE:
<223> OTHER INFORMATION: synthetic primer

<400> SEQUENCE: 237
cagaccctgg ggctactacc                                                   20

<210> SEQ ID NO 238
<211> LENGTH: 17
<212> TYPE: DNA
<213> ORGANISM: Artificial Sequence
<220> FEATURE:
<223> OTHER INFORMATION: synthetic primer
```

```
<400> SEQUENCE: 238
cctggtgggc aaagagg                                                        17

<210> SEQ ID NO 239
<211> LENGTH: 20
<212> TYPE: DNA
<213> ORGANISM: Artificial Sequence
<220> FEATURE:
<223> OTHER INFORMATION: synthetic primer

<400> SEQUENCE: 239
gaggatggct acaggcagag                                                     20

<210> SEQ ID NO 240
<211> LENGTH: 19
<212> TYPE: DNA
<213> ORGANISM: Artificial Sequence
<220> FEATURE:
<223> OTHER INFORMATION: synthetic primer

<400> SEQUENCE: 240
cagccctcca cagtccaag                                                      19

<210> SEQ ID NO 241
<211> LENGTH: 20
<212> TYPE: DNA
<213> ORGANISM: Artificial Sequence
<220> FEATURE:
<223> OTHER INFORMATION: synthetic primer

<400> SEQUENCE: 241
catcgtcccc tagagacagc                                                     20

<210> SEQ ID NO 242
<211> LENGTH: 20
<212> TYPE: DNA
<213> ORGANISM: Artificial Sequence
<220> FEATURE:
<223> OTHER INFORMATION: synthetic primer

<400> SEQUENCE: 242
tctggtgcca tggagagtag                                                     20

<210> SEQ ID NO 243
<211> LENGTH: 17
<212> TYPE: DNA
<213> ORGANISM: Artificial Sequence
<220> FEATURE:
<223> OTHER INFORMATION: synthetic primer

<400> SEQUENCE: 243
gctcaggacg tggggac                                                        17

<210> SEQ ID NO 244
<211> LENGTH: 17
<212> TYPE: DNA
<213> ORGANISM: Artificial Sequence
<220> FEATURE:
<223> OTHER INFORMATION: synthetic primer

<400> SEQUENCE: 244
ctggggatga ggggatg                                                        17

<210> SEQ ID NO 245
<211> LENGTH: 20
<212> TYPE: DNA
```

```
<213> ORGANISM: Artificial Sequence
<220> FEATURE:
<223> OTHER INFORMATION: synthetic primer

<400> SEQUENCE: 245
agtgtggata tgtggggagc                                                    20

<210> SEQ ID NO 246
<211> LENGTH: 19
<212> TYPE: DNA
<213> ORGANISM: Artificial Sequence
<220> FEATURE:
<223> OTHER INFORMATION: synthetic primer

<400> SEQUENCE: 246
tgaacactgc aggcctctc                                                     19

<210> SEQ ID NO 247
<211> LENGTH: 21
<212> TYPE: DNA
<213> ORGANISM: Artificial Sequence
<220> FEATURE:
<223> OTHER INFORMATION: synthetic primer

<400> SEQUENCE: 247
aatacagatc atggcacgag g                                                  21

<210> SEQ ID NO 248
<211> LENGTH: 20
<212> TYPE: DNA
<213> ORGANISM: Artificial Sequence
<220> FEATURE:
<223> OTHER INFORMATION: synthetic primer

<400> SEQUENCE: 248
gcacagcttt ccaggaggag                                                    20

<210> SEQ ID NO 249
<211> LENGTH: 20
<212> TYPE: DNA
<213> ORGANISM: Artificial Sequence
<220> FEATURE:
<223> OTHER INFORMATION: synthetic primer

<400> SEQUENCE: 249
aagtcccaca agcccctaag                                                    20

<210> SEQ ID NO 250
<211> LENGTH: 20
<212> TYPE: DNA
<213> ORGANISM: Artificial Sequence
<220> FEATURE:
<223> OTHER INFORMATION: synthetic primer

<400> SEQUENCE: 250 cctttctctcc tcacaccagg                                                   20

<210> SEQ ID NO 251
<211> LENGTH: 20
<212> TYPE: DNA
<213> ORGANISM: Artificial Sequence
<220> FEATURE:
<223> OTHER INFORMATION: synthetic primer

<400> SEQUENCE: 251
agggcagcct tgtctctcag                                                    20
```

```
<210> SEQ ID NO 252
<211> LENGTH: 18
<212> TYPE: DNA
<213> ORGANISM: Artificial Sequence
<220> FEATURE:
<223> OTHER INFORMATION: synthetic primer

<400> SEQUENCE: 252
ctcagggtca ggctccag                                                 18

<210> SEQ ID NO 253
<211> LENGTH: 20
<212> TYPE: DNA
<213> ORGANISM: Artificial Sequence
<220> FEATURE:
<223> OTHER INFORMATION: synthetic primer

<400> SEQUENCE: 253
tctgagctct gtccaaaggc                                               20

<210> SEQ ID NO 254
<211> LENGTH: 20
<212> TYPE: DNA
<213> ORGANISM: Artificial Sequence
<220> FEATURE:
<223> OTHER INFORMATION: synthetic primer

<400> SEQUENCE: 254
catctcaccc acagctcctc                                               20

<210> SEQ ID NO 255
<211> LENGTH: 20
<212> TYPE: DNA
<213> ORGANISM: Artificial Sequence
<220> FEATURE:
<223> OTHER INFORMATION: synthetic primer

<400> SEQUENCE: 255
aacttcccca gtgtgagtcc                                               20

<210> SEQ ID NO 256
<211> LENGTH: 18
<212> TYPE: DNA
<213> ORGANISM: Artificial Sequence
<220> FEATURE:
<223> OTHER INFORMATION: synthetic primer

<400> SEQUENCE: 256
cagggacagt ggcagcag                                                 18

<210> SEQ ID NO 257
<211> LENGTH: 20
<212> TYPE: DNA
<213> ORGANISM: Artificial Sequence
<220> FEATURE:
<223> OTHER INFORMATION: synthetic primer

<400> SEQUENCE: 257
aagagcagat cccatccctc                                               20

<210> SEQ ID NO 258
<211> LENGTH: 17
<212> TYPE: DNA
<213> ORGANISM: Artificial Sequence
<220> FEATURE:
<223> OTHER INFORMATION: synthetic primer
```

-continued

```
<400> SEQUENCE: 258
accacccagc ggtgatg                                                  17

<210> SEQ ID NO 259
<211> LENGTH: 26
<212> TYPE: DNA
<213> ORGANISM: Artificial Sequence
<220> FEATURE:
<223> OTHER INFORMATION: synthetic primer

<400> SEQUENCE: 259
gccattggag ttttacactt attttc                                        26

<210> SEQ ID NO 260
<211> LENGTH: 20
<212> TYPE: DNA
<213> ORGANISM: Artificial Sequence
<220> FEATURE:
<223> OTHER INFORMATION: synthetic primer

<400> SEQUENCE: 260
accaacaccc aaatcgagag                                               20

<210> SEQ ID NO 261
<211> LENGTH: 26
<212> TYPE: DNA
<213> ORGANISM: Artificial Sequence
<220> FEATURE:
<223> OTHER INFORMATION: synthetic primer

<400> SEQUENCE: 261
gcaatcaata acatgctatc tttgag                                        26

<210> SEQ ID NO 262
<211> LENGTH: 22
<212> TYPE: DNA
<213> ORGANISM: Artificial Sequence
<220> FEATURE:
<223> OTHER INFORMATION: synthetic primer

<400> SEQUENCE: 262
caggcctaaa gttgggtaaa ac                                            22

<210> SEQ ID NO 263
<211> LENGTH: 21
<212> TYPE: DNA
<213> ORGANISM: Artificial Sequence
<220> FEATURE:
<223> OTHER INFORMATION: synthetic primer

<400> SEQUENCE: 263
agagccaaaa taaacacagc c                                             21

<210> SEQ ID NO 264
<211> LENGTH: 22
<212> TYPE: DNA
<213> ORGANISM: Artificial Sequence
<220> FEATURE:
<223> OTHER INFORMATION: synthetic primer

<400> SEQUENCE: 264
ggggtttctg gagtaaacac ag                                            22

<210> SEQ ID NO 265
<211> LENGTH: 25
<212> TYPE: DNA
```

```
<213> ORGANISM: Artificial Sequence
<220> FEATURE:
<223> OTHER INFORMATION: synthetic primer

<400> SEQUENCE: 265
ttcttagaac catcttgctt catac                                          25

<210> SEQ ID NO 266
<211> LENGTH: 19
<212> TYPE: DNA
<213> ORGANISM: Artificial Sequence
<220> FEATURE:
<223> OTHER INFORMATION: synthetic primer

<400> SEQUENCE: 266
agagatgggg ttttgccac                                                 19

<210> SEQ ID NO 267
<211> LENGTH: 23
<212> TYPE: DNA
<213> ORGANISM: Artificial Sequence
<220> FEATURE:
<223> OTHER INFORMATION: synthetic primer

<400> SEQUENCE: 267
tggctgatat gaattttctc ctc                                            23

<210> SEQ ID NO 268
<211> LENGTH: 23
<212> TYPE: DNA
<213> ORGANISM: Artificial Sequence
<220> FEATURE:
<223> OTHER INFORMATION: synthetic primer

<400> SEQUENCE: 268
ttggtggcct tatatcctaa ttc                                            23

<210> SEQ ID NO 269
<211> LENGTH: 19
<212> TYPE: DNA
<213> ORGANISM: Artificial Sequence
<220> FEATURE:
<223> OTHER INFORMATION: synthetic primer

<400> SEQUENCE: 269
agcgaatgtg aagcacagg                                                 19

<210> SEQ ID NO 270
<211> LENGTH: 20
<212> TYPE: DNA
<213> ORGANISM: Artificial Sequence
<220> FEATURE:
<223> OTHER INFORMATION: synthetic primer

<400> SEQUENCE: 270
agtgagaccc tgcctcaaag                                                20

<210> SEQ ID NO 271
<211> LENGTH: 23
<212> TYPE: DNA
<213> ORGANISM: Artificial Sequence
<220> FEATURE:
<223> OTHER INFORMATION: synthetic primer

<400> SEQUENCE: 271
gaaatctcat ggctaaaaga agg                                            23
```

```
<210> SEQ ID NO 272
<211> LENGTH: 20
<212> TYPE: DNA
<213> ORGANISM: Artificial Sequence
<220> FEATURE:
<223> OTHER INFORMATION: synthetic primer

<400> SEQUENCE: 272
cctccaccta tgggctacac                                                   20

<210> SEQ ID NO 273
<211> LENGTH: 27
<212> TYPE: DNA
<213> ORGANISM: Artificial Sequence
<220> FEATURE:
<223> OTHER INFORMATION: synthetic primer

<400> SEQUENCE: 273
gggtaacact gtagtattca aatatgg                                           27

<210> SEQ ID NO 274
<211> LENGTH: 21
<212> TYPE: DNA
<213> ORGANISM: Artificial Sequence
<220> FEATURE:
<223> OTHER INFORMATION: synthetic primer

<400> SEQUENCE: 274
caatcgaggg tttcatttga c                                                 21

<210> SEQ ID NO 275
<211> LENGTH: 26
<212> TYPE: DNA
<213> ORGANISM: Artificial Sequence
<220> FEATURE:
<223> OTHER INFORMATION: synthetic primer

<400> SEQUENCE: 275
ttcagagtaa cgttcactat aattgg                                            26

<210> SEQ ID NO 276
<211> LENGTH: 22
<212> TYPE: DNA
<213> ORGANISM: Artificial Sequence
<220> FEATURE:
<223> OTHER INFORMATION: synthetic primer

<400> SEQUENCE: 276
cctgtgtcgt ctgattacat cc                                                22

<210> SEQ ID NO 277
<211> LENGTH: 20
<212> TYPE: DNA
<213> ORGANISM: Artificial Sequence
<220> FEATURE:
<223> OTHER INFORMATION: synthetic primer

<400> SEQUENCE: 277
cgcttggttt gagctgtttg                                                   20

<210> SEQ ID NO 278
<211> LENGTH: 20
<212> TYPE: DNA
<213> ORGANISM: Artificial Sequence
<220> FEATURE:
<223> OTHER INFORMATION: synthetic primer
```

```
<400> SEQUENCE: 278
agctgacttg gtttccttgc                                              20

<210> SEQ ID NO 279
<211> LENGTH: 20
<212> TYPE: DNA
<213> ORGANISM: Artificial Sequence
<220> FEATURE:
<223> OTHER INFORMATION: synthetic primer

<400> SEQUENCE: 279
tttgttgggt gcagaagaag                                              20

<210> SEQ ID NO 280
<211> LENGTH: 20
<212> TYPE: DNA
<213> ORGANISM: Artificial Sequence
<220> FEATURE:
<223> OTHER INFORMATION: synthetic primer

<400> SEQUENCE: 280
gctgacctcg atttattggc                                              20

<210> SEQ ID NO 281
<211> LENGTH: 26
<212> TYPE: DNA
<213> ORGANISM: Artificial Sequence
<220> FEATURE:
<223> OTHER INFORMATION: synthetic primer

<400> SEQUENCE: 281
aagtgtcaga tcttcaccta atatgc                                       26

<210> SEQ ID NO 282
<211> LENGTH: 19
<212> TYPE: DNA
<213> ORGANISM: Artificial Sequence
<220> FEATURE:
<223> OTHER INFORMATION: synthetic primer

<400> SEQUENCE: 282
gaatcattgt cctgcctcg                                               19

<210> SEQ ID NO 283
<211> LENGTH: 20
<212> TYPE: DNA
<213> ORGANISM: Artificial Sequence
<220> FEATURE:
<223> OTHER INFORMATION: synthetic primer

<400> SEQUENCE: 283
tcctttggag gcagactcac                                              20

<210> SEQ ID NO 284
<211> LENGTH: 20
<212> TYPE: DNA
<213> ORGANISM: Artificial Sequence
<220> FEATURE:
<223> OTHER INFORMATION: synthetic primer

<400> SEQUENCE: 284
acgtttccag gttcctgacc                                              20

<210> SEQ ID NO 285
<211> LENGTH: 20
<212> TYPE: DNA
```

<213> ORGANISM: Artificial Sequence
<220> FEATURE:
<223> OTHER INFORMATION: synthetic primer

<400> SEQUENCE: 285
atgggaacac tgccattacc                                              20

<210> SEQ ID NO 286
<211> LENGTH: 24
<212> TYPE: DNA
<213> ORGANISM: Artificial Sequence
<220> FEATURE:
<223> OTHER INFORMATION: synthetic primer

<400> SEQUENCE: 286
aaaccctcta acaagaatca aacc                                         24

<210> SEQ ID NO 287
<211> LENGTH: 43
<212> TYPE: DNA
<213> ORGANISM: Artificial Sequence
<220> FEATURE:
<223> OTHER INFORMATION: synthetic primer

<400> SEQUENCE: 287
cucagacauc aaucugaagc auggcaugaa cccacuuccu gac                    43

<210> SEQ ID NO 288
<211> LENGTH: 41
<212> TYPE: DNA
<213> ORGANISM: Artificial Sequence
<220> FEATURE:
<223> OTHER INFORMATION: synthetic primer

<400> SEQUENCE: 288
cuggccucac ccuaccucuu agagcaguuu gagacagugg c                      41

<210> SEQ ID NO 289
<211> LENGTH: 37
<212> TYPE: DNA
<213> ORGANISM: Artificial Sequence
<220> FEATURE:
<223> OTHER INFORMATION: synthetic primer

<400> SEQUENCE: 289
cuucgagcau uauuccaggg ucugcacgug ucagggg                           37

<210> SEQ ID NO 290
<211> LENGTH: 39
<212> TYPE: DNA
<213> ORGANISM: Artificial Sequence
<220> FEATURE:
<223> OTHER INFORMATION: synthetic primer

<400> SEQUENCE: 290
gguggcagag aauucuggaa caugcucauu uccuuuggc                         39

<210> SEQ ID NO 291
<211> LENGTH: 40
<212> TYPE: DNA
<213> ORGANISM: Artificial Sequence
<220> FEATURE:
<223> OTHER INFORMATION: synthetic primer

<400> SEQUENCE: 291
ccccucucac caaagaacag uagcaacaag gucagcaggc                        40

<210> SEQ ID NO 292
<211> LENGTH: 37
<212> TYPE: DNA
<213> ORGANISM: Artificial Sequence
<220> FEATURE:
<223> OTHER INFORMATION: synthetic primer

<400> SEQUENCE: 292
gggcugagga ccggucaug cuggaucccc acuuuuc                          37

<210> SEQ ID NO 293
<211> LENGTH: 37
<212> TYPE: DNA
<213> ORGANISM: Artificial Sequence
<220> FEATURE:
<223> OTHER INFORMATION: synthetic primer

<400> SEQUENCE: 293
gauuccucuu cacccuuugg gacaagggu gggcugg                          37

<210> SEQ ID NO 294
<211> LENGTH: 36
<212> TYPE: DNA
<213> ORGANISM: Artificial Sequence
<220> FEATURE:
<223> OTHER INFORMATION: synthetic primer

<400> SEQUENCE: 294
gugguuguca guggcccuuc uuugcugccg ucuucc                          36

<210> SEQ ID NO 295
<211> LENGTH: 37
<212> TYPE: DNA
<213> ORGANISM: Artificial Sequence
<220> FEATURE:
<223> OTHER INFORMATION: synthetic primer

<400> SEQUENCE: 295
gccucugcuu gccucugacu gcuugccaca ggucucc                         37

<210> SEQ ID NO 296
<211> LENGTH: 44
<212> TYPE: DNA
<213> ORGANISM: Artificial Sequence
<220> FEATURE:
<223> OTHER INFORMATION: synthetic primer

<400> SEQUENCE: 296
gccguuuucu ucuugacugu uuggacaggu aggaccugau uucc                 44

<210> SEQ ID NO 297
<211> LENGTH: 46
<212> TYPE: DNA
<213> ORGANISM: Artificial Sequence
<220> FEATURE:
<223> OTHER INFORMATION: synthetic primer

<400> SEQUENCE: 297
guuggaaagc cauaggauuc caacuugaac caucuuuuaa cucagg               46

<210> SEQ ID NO 298
<211> LENGTH: 38
<212> TYPE: DNA
<213> ORGANISM: Artificial Sequence
<220> FEATURE:
<223> OTHER INFORMATION: synthetic primer -continued

```
<400> SEQUENCE: 298
ccauuuuggg uuuugggucu aggggcacag acccucuc                                38

<210> SEQ ID NO 299
<211> LENGTH: 20
<212> TYPE: DNA
<213> ORGANISM: Artificial Sequence
<220> FEATURE:
<223> OTHER INFORMATION: synthetic primer

<400> SEQUENCE: 299
tcatcactgt tcggcttctg                                                    20

<210> SEQ ID NO 300
<211> LENGTH: 20
<212> TYPE: DNA
<213> ORGANISM: Artificial Sequence
<220> FEATURE:
<223> OTHER INFORMATION: synthetic primer

<400> SEQUENCE: 300
atttgttgcc ggaaaacttg                                                    20

<210> SEQ ID NO 301
<211> LENGTH: 20
<212> TYPE: DNA
<213> ORGANISM: Artificial Sequence
<220> FEATURE:
<223> OTHER INFORMATION: synthetic primer

<400> SEQUENCE: 301
ccacagcagt gtggtcattc                                                    20

<210> SEQ ID NO 302
<211> LENGTH: 19
<212> TYPE: DNA
<213> ORGANISM: Artificial Sequence
<220> FEATURE:
<223> OTHER INFORMATION: synthetic primer

<400> SEQUENCE: 302
aactgctaat ggcccgttc                                                     19

<210> SEQ ID NO 303
<211> LENGTH: 20
<212> TYPE: DNA
<213> ORGANISM: Artificial Sequence
<220> FEATURE:
<223> OTHER INFORMATION: synthetic primer

<400> SEQUENCE: 303
acagcttgca aggactctgg                                                    20

<210> SEQ ID NO 304
<211> LENGTH: 20
<212> TYPE: DNA
<213> ORGANISM: Artificial Sequence
<220> FEATURE:
<223> OTHER INFORMATION: synthetic primer

<400> SEQUENCE: 304
agacatgaga aaggtgggc                                                     20

<210> SEQ ID NO 305
<211> LENGTH: 19
<212> TYPE: DNA
```

<213> ORGANISM: Artificial Sequence
<220> FEATURE:
<223> OTHER INFORMATION: synthetic primer

<400> SEQUENCE: 305
ctatcccagg agcgcagac                                                   19

<210> SEQ ID NO 306
<211> LENGTH: 20
<212> TYPE: DNA
<213> ORGANISM: Artificial Sequence
<220> FEATURE:
<223> OTHER INFORMATION: synthetic primer

<400> SEQUENCE: 306
tacagctagt gggaaggcag                                                  20

<210> SEQ ID NO 307
<211> LENGTH: 25
<212> TYPE: DNA
<213> ORGANISM: Artificial Sequence
<220> FEATURE:
<223> OTHER INFORMATION: synthetic primer

<400> SEQUENCE: 307
aaagaaaata cttgcatgtc agagg                                            25

<210> SEQ ID NO 308
<211> LENGTH: 20
<212> TYPE: DNA
<213> ORGANISM: Artificial Sequence
<220> FEATURE:
<223> OTHER INFORMATION: synthetic primer

<400> SEQUENCE: 308
ctgtttggct aagagcagcc                                                  20

<210> SEQ ID NO 309
<211> LENGTH: 23
<212> TYPE: DNA
<213> ORGANISM: Artificial Sequence
<220> FEATURE:
<223> OTHER INFORMATION: synthetic primer

<400> SEQUENCE: 309
cagaacacag tgacatgaga tgc                                              23

<210> SEQ ID NO 310
<211> LENGTH: 26
<212> TYPE: DNA
<213> ORGANISM: Artificial Sequence
<220> FEATURE:
<223> OTHER INFORMATION: synthetic primer

<400> SEQUENCE: 310
gagtttcact agatggttat tttccc                                           26

<210> SEQ ID NO 311
<211> LENGTH: 24
<212> TYPE: DNA
<213> ORGANISM: Artificial Sequence
<220> FEATURE:
<223> OTHER INFORMATION: synthetic primer

<400> SEQUENCE: 311
tccatgtaaa atagagccat agtg                                             24

```
<210> SEQ ID NO 312
<211> LENGTH: 19
<212> TYPE: DNA
<213> ORGANISM: Artificial Sequence
<220> FEATURE:
<223> OTHER INFORMATION: synthetic primer

<400> SEQUENCE: 312
ttggacactg gagactggc                                                  19

<210> SEQ ID NO 313
<211> LENGTH: 20
<212> TYPE: DNA
<213> ORGANISM: Artificial Sequence
<220> FEATURE:
<223> OTHER INFORMATION: synthetic primer

<400> SEQUENCE: 313
gtggcttggt cctgggtatc                                                 20

<210> SEQ ID NO 314
<211> LENGTH: 22
<212> TYPE: DNA
<213> ORGANISM: Artificial Sequence
<220> FEATURE:
<223> OTHER INFORMATION: synthetic primer

<400> SEQUENCE: 314
tgatggtaca tttagcccac ac                                              22

<210> SEQ ID NO 315
<211> LENGTH: 20
<212> TYPE: DNA
<213> ORGANISM: Artificial Sequence
<220> FEATURE:
<223> OTHER INFORMATION: synthetic primer

<400> SEQUENCE: 315
taagtggcag acacagggtg                                                 20

<210> SEQ ID NO 316
<211> LENGTH: 20
<212> TYPE: DNA
<213> ORGANISM: Artificial Sequence
<220> FEATURE:
<223> OTHER INFORMATION: synthetic primer

<400> SEQUENCE: 316
agaaggaagc aaaagacccc                                                 20

<210> SEQ ID NO 317
<211> LENGTH: 20
<212> TYPE: DNA
<213> ORGANISM: Artificial Sequence
<220> FEATURE:
<223> OTHER INFORMATION: synthetic primer

<400> SEQUENCE: 317
aggccaggtg attctctacg                                                 20

<210> SEQ ID NO 318
<211> LENGTH: 20
<212> TYPE: DNA
<213> ORGANISM: Artificial Sequence
<220> FEATURE:
<223> OTHER INFORMATION: synthetic primer
```

```
<400> SEQUENCE: 318
cgctcacaga atggtacacg                                          20

<210> SEQ ID NO 319
<211> LENGTH: 20
<212> TYPE: DNA
<213> ORGANISM: Artificial Sequence
<220> FEATURE:
<223> OTHER INFORMATION: synthetic primer

<400> SEQUENCE: 319
cctgttccct gtttaccctg                                          20

<210> SEQ ID NO 320
<211> LENGTH: 20
<212> TYPE: DNA
<213> ORGANISM: Artificial Sequence
<220> FEATURE:
<223> OTHER INFORMATION: synthetic primer

<400> SEQUENCE: 320
agcgtccttc ctctccaacc                                          20

<210> SEQ ID NO 321
<211> LENGTH: 20
<212> TYPE: DNA
<213> ORGANISM: Artificial Sequence
<220> FEATURE:
<223> OTHER INFORMATION: synthetic primer

<400> SEQUENCE: 321
taacagtccc aacactgggg                                          20

<210> SEQ ID NO 322
<211> LENGTH: 20
<212> TYPE: DNA
<213> ORGANISM: Artificial Sequence
<220> FEATURE:
<223> OTHER INFORMATION: synthetic primer

<400> SEQUENCE: 322
ttcccaaagt ttccagcatc                                          20

<210> SEQ ID NO 323
<211> LENGTH: 20
<212> TYPE: DNA
<213> ORGANISM: Artificial Sequence
<220> FEATURE:
<223> OTHER INFORMATION: synthetic primer

<400> SEQUENCE: 323
ctggctactc ccaattgtcc                                          20

<210> SEQ ID NO 324
<211> LENGTH: 19
<212> TYPE: DNA
<213> ORGANISM: Artificial Sequence
<220> FEATURE:
<223> OTHER INFORMATION: synthetic primer

<400> SEQUENCE: 324
tcaagcagtt ctcacagcg                                           19

<210> SEQ ID NO 325
<211> LENGTH: 20
<212> TYPE: DNA
```

-continued

```
<213> ORGANISM: Artificial Sequence
<220> FEATURE:
<223> OTHER INFORMATION: synthetic primer

<400> SEQUENCE: 325
tccccatatg agctgatgac                                               20

<210> SEQ ID NO 326
<211> LENGTH: 22
<212> TYPE: DNA
<213> ORGANISM: Artificial Sequence
<220> FEATURE:
<223> OTHER INFORMATION: synthetic primer

<400> SEQUENCE: 326
gaggttagtt tcttttccac cc                                            22

<210> SEQ ID NO 327
<211> LENGTH: 21
<212> TYPE: DNA
<213> ORGANISM: Artificial Sequence
<220> FEATURE:
<223> OTHER INFORMATION: synthetic primer

<400> SEQUENCE: 327
aaagagaagc aaagtccctg g                                             21

<210> SEQ ID NO 328
<211> LENGTH: 20
<212> TYPE: DNA
<213> ORGANISM: Artificial Sequence
<220> FEATURE:
<223> OTHER INFORMATION: synthetic primer

<400> SEQUENCE: 328
gcaaccatct ctctcttgcc                                               20

<210> SEQ ID NO 329
<211> LENGTH: 20
<212> TYPE: DNA
<213> ORGANISM: Artificial Sequence
<220> FEATURE:
<223> OTHER INFORMATION: synthetic primer

<400> SEQUENCE: 329
gcaagggctc tgtgagtgag                                               20

<210> SEQ ID NO 330
<211> LENGTH: 20
<212> TYPE: DNA
<213> ORGANISM: Artificial Sequence
<220> FEATURE:
<223> OTHER INFORMATION: synthetic primer

<400> SEQUENCE: 330
gatctgtgca tgtgtggtgc                                               20

<210> SEQ ID NO 331
<211> LENGTH: 20
<212> TYPE: DNA
<213> ORGANISM: Artificial Sequence
<220> FEATURE:
<223> OTHER INFORMATION: synthetic primer

<400> SEQUENCE: 331
ttcaaacttg cttctgagcc                                               20
```

```
<210> SEQ ID NO 332
<211> LENGTH: 20
<212> TYPE: DNA
<213> ORGANISM: Artificial Sequence
<220> FEATURE:
<223> OTHER INFORMATION: synthetic primer

<400> SEQUENCE: 332
ccagggactc agaggaaatc                                           20

<210> SEQ ID NO 333
<211> LENGTH: 23
<212> TYPE: DNA
<213> ORGANISM: Artificial Sequence
<220> FEATURE:
<223> OTHER INFORMATION: synthetic primer

<400> SEQUENCE: 333
gcctgggaac ttaagaaatg aac                                       23

<210> SEQ ID NO 334
<211> LENGTH: 21
<212> TYPE: DNA
<213> ORGANISM: Artificial Sequence
<220> FEATURE:
<223> OTHER INFORMATION: synthetic primer

<400> SEQUENCE: 334
tggctcacag acaaagtctt c                                         21

<210> SEQ ID NO 335
<211> LENGTH: 20
<212> TYPE: DNA
<213> ORGANISM: Artificial Sequence
<220> FEATURE:
<223> OTHER INFORMATION: synthetic primer

<400> SEQUENCE: 335
cacaaactcc catagccaag                                           20

<210> SEQ ID NO 336
<211> LENGTH: 17
<212> TYPE: DNA
<213> ORGANISM: Artificial Sequence
<220> FEATURE:
<223> OTHER INFORMATION: synthetic primer

<400> SEQUENCE: 336
ctggttttcg gttgccc                                              17

<210> SEQ ID NO 337
<211> LENGTH: 22
<212> TYPE: DNA
<213> ORGANISM: Artificial Sequence
<220> FEATURE:
<223> OTHER INFORMATION: synthetic primer

<400> SEQUENCE: 337
ccagcccctt gattattact tc                                        22

<210> SEQ ID NO 338
<211> LENGTH: 20
<212> TYPE: DNA
<213> ORGANISM: Artificial Sequence
<220> FEATURE:
<223> OTHER INFORMATION: synthetic primer
```

```
<400> SEQUENCE: 338
gcagtgggag aagagaggtc                                              20

<210> SEQ ID NO 339
<211> LENGTH: 20
<212> TYPE: DNA
<213> ORGANISM: Artificial Sequence
<220> FEATURE:
<223> OTHER INFORMATION: synthetic primer

<400> SEQUENCE: 339
tgaaggtcag ggccaataac                                              20

<210> SEQ ID NO 340
<211> LENGTH: 20
<212> TYPE: DNA
<213> ORGANISM: Artificial Sequence
<220> FEATURE:
<223> OTHER INFORMATION: synthetic primer

<400> SEQUENCE: 340
aagtgagaac tccgtgtggg                                              20

<210> SEQ ID NO 341
<211> LENGTH: 20
<212> TYPE: DNA
<213> ORGANISM: Artificial Sequence
<220> FEATURE:
<223> OTHER INFORMATION: synthetic primer

<400> SEQUENCE: 341 gagccccctag cctcactcac                                             20

<210> SEQ ID NO 342
<211> LENGTH: 20
<212> TYPE: DNA
<213> ORGANISM: Artificial Sequence
<220> FEATURE:
<223> OTHER INFORMATION: synthetic primer

<400> SEQUENCE: 342
tctttaccaa agcaccgtgg                                              20

<210> SEQ ID NO 343
<211> LENGTH: 18
<212> TYPE: DNA
<213> ORGANISM: Artificial Sequence
<220> FEATURE:
<223> OTHER INFORMATION: synthetic primer

<400> SEQUENCE: 343
gtcctggaag gggtaggg                                                18

<210> SEQ ID NO 344
<211> LENGTH: 20
<212> TYPE: DNA
<213> ORGANISM: Artificial Sequence
<220> FEATURE:
<223> OTHER INFORMATION: synthetic primer

<400> SEQUENCE: 344
gcagagcgaa gcagattagg                                              20

<210> SEQ ID NO 345
<211> LENGTH: 18
<212> TYPE: DNA
```

```
<213> ORGANISM: Artificial Sequence
<220> FEATURE:
<223> OTHER INFORMATION: synthetic primer

<400> SEQUENCE: 345
gcagaagctg ctgggatg                                                 18

<210> SEQ ID NO 346
<211> LENGTH: 20
<212> TYPE: DNA
<213> ORGANISM: Artificial Sequence
<220> FEATURE:
<223> OTHER INFORMATION: synthetic primer

<400> SEQUENCE: 346
tcagctgtaa ccacgagcac                                               20

<210> SEQ ID NO 347
<211> LENGTH: 18
<212> TYPE: DNA
<213> ORGANISM: Artificial Sequence
<220> FEATURE:
<223> OTHER INFORMATION: synthetic primer

<400> SEQUENCE: 347
ctcagagagc ctggcacc                                                 18

<210> SEQ ID NO 348
<211> LENGTH: 20
<212> TYPE: DNA
<213> ORGANISM: Artificial Sequence
<220> FEATURE:
<223> OTHER INFORMATION: synthetic primer

<400> SEQUENCE: 348
agggtcagga agggaaagag                                               20

<210> SEQ ID NO 349
<211> LENGTH: 20
<212> TYPE: DNA
<213> ORGANISM: Artificial Sequence
<220> FEATURE:
<223> OTHER INFORMATION: synthetic primer

<400> SEQUENCE: 349
agcttttgga aaggctgacc                                               20

<210> SEQ ID NO 350
<211> LENGTH: 18
<212> TYPE: DNA
<213> ORGANISM: Artificial Sequence
<220> FEATURE:
<223> OTHER INFORMATION: synthetic primer

<400> SEQUENCE: 350
cccaccagct aagggacc                                                 18

<210> SEQ ID NO 351
<211> LENGTH: 20
<212> TYPE: DNA
<213> ORGANISM: Artificial Sequence
<220> FEATURE:
<223> OTHER INFORMATION: synthetic primer

<400> SEQUENCE: 351
tgggtcacgt cctttcattc                                               20
```

```
<210> SEQ ID NO 352
<211> LENGTH: 21
<212> TYPE: DNA
<213> ORGANISM: Artificial Sequence
<220> FEATURE:
<223> OTHER INFORMATION: synthetic primer

<400> SEQUENCE: 352
ccagatgctt tggaatgagt g                                              21

<210> SEQ ID NO 353
<211> LENGTH: 20
<212> TYPE: DNA
<213> ORGANISM: Artificial Sequence
<220> FEATURE:
<223> OTHER INFORMATION: synthetic primer

<400> SEQUENCE: 353
gaagagggaa ggggtctcag                                                20

<210> SEQ ID NO 354
<211> LENGTH: 24
<212> TYPE: DNA
<213> ORGANISM: Artificial Sequence
<220> FEATURE:
<223> OTHER INFORMATION: synthetic primer

<400> SEQUENCE: 354
atgactacac gagacaaatg tagg                                           24

<210> SEQ ID NO 355
<211> LENGTH: 19
<212> TYPE: DNA
<213> ORGANISM: Artificial Sequence
<220> FEATURE:
<223> OTHER INFORMATION: synthetic primer

<400> SEQUENCE: 355
agcagcgcta cggagattc                                                 19

<210> SEQ ID NO 356
<211> LENGTH: 19
<212> TYPE: DNA
<213> ORGANISM: Artificial Sequence
<220> FEATURE:
<223> OTHER INFORMATION: synthetic primer

<400> SEQUENCE: 356
catcctattg cgagtgggg                                                 19

<210> SEQ ID NO 357
<211> LENGTH: 22
<212> TYPE: DNA
<213> ORGANISM: Artificial Sequence
<220> FEATURE:
<223> OTHER INFORMATION: synthetic primer

<400> SEQUENCE: 357
aaaccaaatg aaaccattca gg                                             22

<210> SEQ ID NO 358
<211> LENGTH: 21
<212> TYPE: DNA
<213> ORGANISM: Artificial Sequence
<220> FEATURE:
<223> OTHER INFORMATION: synthetic primer
```

```
<400> SEQUENCE: 358
tgggcttaag tctgcctaca g                                           21

<210> SEQ ID NO 359
<211> LENGTH: 22
<212> TYPE: DNA
<213> ORGANISM: Artificial Sequence
<220> FEATURE:
<223> OTHER INFORMATION: synthetic primer

<400> SEQUENCE: 359
aaggctgtaa ctgtcctgat cc                                          22

<210> SEQ ID NO 360
<211> LENGTH: 20
<212> TYPE: DNA
<213> ORGANISM: Artificial Sequence
<220> FEATURE:
<223> OTHER INFORMATION: synthetic primer

<400> SEQUENCE: 360
caagcaactc ctctgccttg                                             20

<210> SEQ ID NO 361
<211> LENGTH: 20
<212> TYPE: DNA
<213> ORGANISM: Artificial Sequence
<220> FEATURE:
<223> OTHER INFORMATION: synthetic primer

<400> SEQUENCE: 361
acaaacactc tgcacaaggg                                             20

<210> SEQ ID NO 362
<211> LENGTH: 22
<212> TYPE: DNA
<213> ORGANISM: Artificial Sequence
<220> FEATURE:
<223> OTHER INFORMATION: synthetic primer

<400> SEQUENCE: 362
tcagagagga aagtgtgctc ag                                          22

<210> SEQ ID NO 363
<211> LENGTH: 20
<212> TYPE: DNA
<213> ORGANISM: Artificial Sequence
<220> FEATURE:
<223> OTHER INFORMATION: synthetic primer

<400> SEQUENCE: 363
tttgctactc tggctttggg                                             20

<210> SEQ ID NO 364
<211> LENGTH: 25
<212> TYPE: DNA
<213> ORGANISM: Artificial Sequence
<220> FEATURE:
<223> OTHER INFORMATION: synthetic primer

<400> SEQUENCE: 364
cctttatctg tatcaaagaa tggtc                                       25

<210> SEQ ID NO 365
<211> LENGTH: 20
<212> TYPE: DNA
```

```
<213> ORGANISM: Artificial Sequence
<220> FEATURE:
<223> OTHER INFORMATION: synthetic primer

<400> SEQUENCE: 365
tgcatggcat tagcaaagac                                               20

<210> SEQ ID NO 366
<211> LENGTH: 20
<212> TYPE: DNA
<213> ORGANISM: Artificial Sequence
<220> FEATURE:
<223> OTHER INFORMATION: synthetic primer

<400> SEQUENCE: 366
agaagcaatg ccctctcaag                                               20

<210> SEQ ID NO 367
<211> LENGTH: 20
<212> TYPE: DNA
<213> ORGANISM: Artificial Sequence
<220> FEATURE:
<223> OTHER INFORMATION: synthetic primer

<400> SEQUENCE: 367
gtggttgcca ccttgttacc                                               20

<210> SEQ ID NO 368
<211> LENGTH: 18
<212> TYPE: DNA
<213> ORGANISM: Artificial Sequence
<220> FEATURE:
<223> OTHER INFORMATION: synthetic primer

<400> SEQUENCE: 368
gaggagcacg aatgccac                                                 18

<210> SEQ ID NO 369
<211> LENGTH: 18
<212> TYPE: DNA
<213> ORGANISM: Artificial Sequence
<220> FEATURE:
<223> OTHER INFORMATION: synthetic primer

<400> SEQUENCE: 369
atggtgtgaa cccgggag                                                 18

<210> SEQ ID NO 370
<211> LENGTH: 20
<212> TYPE: DNA
<213> ORGANISM: Artificial Sequence
<220> FEATURE:
<223> OTHER INFORMATION: synthetic primer

<400> SEQUENCE: 370
ttagatggca attagcaccg                                               20

<210> SEQ ID NO 371
<211> LENGTH: 22
<212> TYPE: DNA
<213> ORGANISM: Artificial Sequence
<220> FEATURE:
<223> OTHER INFORMATION: synthetic primer

<400> SEQUENCE: 371
aagcttttaa cctgtcttca gc                                            22
```

-continued

<210> SEQ ID NO 372
<211> LENGTH: 20
<212> TYPE: DNA
<213> ORGANISM: Artificial Sequence
<220> FEATURE:
<223> OTHER INFORMATION: synthetic primer

<400> SEQUENCE: 372
ccatatgggc agtatggttg                                                    20

<210> SEQ ID NO 373
<211> LENGTH: 21
<212> TYPE: DNA
<213> ORGANISM: Artificial Sequence
<220> FEATURE:
<223> OTHER INFORMATION: synthetic primer

<400> SEQUENCE: 373
aaacacttgt ttgcttcagg g                                                  21

<210> SEQ ID NO 374
<211> LENGTH: 21
<212> TYPE: DNA
<213> ORGANISM: Artificial Sequence
<220> FEATURE:
<223> OTHER INFORMATION: synthetic primer

<400> SEQUENCE: 374
tgaccactga gagaactgca c                                                  21

<210> SEQ ID NO 375
<211> LENGTH: 24
<212> TYPE: DNA
<213> ORGANISM: Artificial Sequence
<220> FEATURE:
<223> OTHER INFORMATION: synthetic primer

<400> SEQUENCE: 375
cagaggaaag aaaacgagta agtc                                               24

<210> SEQ ID NO 376
<211> LENGTH: 24
<212> TYPE: DNA
<213> ORGANISM: Artificial Sequence
<220> FEATURE:
<223> OTHER INFORMATION: synthetic primer

<400> SEQUENCE: 376
ccattattca cattttaggc acag                                               24

<210> SEQ ID NO 377
<211> LENGTH: 21
<212> TYPE: DNA
<213> ORGANISM: Artificial Sequence
<220> FEATURE:
<223> OTHER INFORMATION: synthetic primer

<400> SEQUENCE: 377
gccaatatcc atcattaagg g                                                  21

<210> SEQ ID NO 378
<211> LENGTH: 20
<212> TYPE: DNA
<213> ORGANISM: Artificial Sequence
<220> FEATURE:
<223> OTHER INFORMATION: synthetic primer

```
<400> SEQUENCE: 378
aggagacctc ttgcctggac                                              20

<210> SEQ ID NO 379
<211> LENGTH: 20
<212> TYPE: DNA
<213> ORGANISM: Artificial Sequence
<220> FEATURE:
<223> OTHER INFORMATION: synthetic primer

<400> SEQUENCE: 379
cctggtgtct agctggttcc                                              20

<210> SEQ ID NO 380
<211> LENGTH: 25
<212> TYPE: DNA
<213> ORGANISM: Artificial Sequence
<220> FEATURE:
<223> OTHER INFORMATION: synthetic primer

<400> SEQUENCE: 380
gcagtaaata acatgcttcc atttc                                        25

<210> SEQ ID NO 381
<211> LENGTH: 20
<212> TYPE: DNA
<213> ORGANISM: Artificial Sequence
<220> FEATURE:
<223> OTHER INFORMATION: synthetic primer

<400> SEQUENCE: 381
ccaggtagca gtggcttcac                                              20

<210> SEQ ID NO 382
<211> LENGTH: 20
<212> TYPE: DNA
<213> ORGANISM: Artificial Sequence
<220> FEATURE:
<223> OTHER INFORMATION: synthetic primer

<400> SEQUENCE: 382
aaaatagtcg cctctgccac                                              20

<210> SEQ ID NO 383
<211> LENGTH: 21
<212> TYPE: DNA
<213> ORGANISM: Artificial Sequence
<220> FEATURE:
<223> OTHER INFORMATION: synthetic primer

<400> SEQUENCE: 383
acatttccat cagtgttcag g                                            21

<210> SEQ ID NO 384
<211> LENGTH: 22
<212> TYPE: DNA
<213> ORGANISM: Artificial Sequence
<220> FEATURE:
<223> OTHER INFORMATION: synthetic primer

<400> SEQUENCE: 384
gtagcttgaa aggaaacgta gc                                           22

<210> SEQ ID NO 385
<211> LENGTH: 17
<212> TYPE: DNA
```

```
<213> ORGANISM: Artificial Sequence
<220> FEATURE:
<223> OTHER INFORMATION: synthetic primer

<400> SEQUENCE: 385
gtcgcgggct atcttcc                                                    17

<210> SEQ ID NO 386
<211> LENGTH: 20
<212> TYPE: DNA
<213> ORGANISM: Artificial Sequence
<220> FEATURE:
<223> OTHER INFORMATION: synthetic primer

<400> SEQUENCE: 386
ttaatgttac tgcctgccgc                                                 20

<210> SEQ ID NO 387
<211> LENGTH: 21
<212> TYPE: DNA
<213> ORGANISM: Artificial Sequence
<220> FEATURE:
<223> OTHER INFORMATION: synthetic primer

<400> SEQUENCE: 387
ttccaagtga ttgtgcatac c                                               21

<210> SEQ ID NO 388
<211> LENGTH: 23
<212> TYPE: DNA
<213> ORGANISM: Artificial Sequence
<220> FEATURE:
<223> OTHER INFORMATION: synthetic primer

<400> SEQUENCE: 388
aaaacagaaa acaaagccct acc                                             23

<210> SEQ ID NO 389
<211> LENGTH: 20
<212> TYPE: DNA
<213> ORGANISM: Artificial Sequence
<220> FEATURE:
<223> OTHER INFORMATION: synthetic primer

<400> SEQUENCE: 389
ttaaagcctg tgtttgtgcg                                                 20

<210> SEQ ID NO 390
<211> LENGTH: 24
<212> TYPE: DNA
<213> ORGANISM: Artificial Sequence
<220> FEATURE:
<223> OTHER INFORMATION: synthetic primer

<400> SEQUENCE: 390
tgtacatggg aaaacataac cttg                                            24

<210> SEQ ID NO 391
<211> LENGTH: 19
<212> TYPE: DNA
<213> ORGANISM: Artificial Sequence
<220> FEATURE:
<223> OTHER INFORMATION: synthetic primer

<400> SEQUENCE: 391
ttttccattc cttccaccc                                                  19
```

```
<210> SEQ ID NO 392
<211> LENGTH: 25
<212> TYPE: DNA
<213> ORGANISM: Artificial Sequence
<220> FEATURE:
<223> OTHER INFORMATION: synthetic primer

<400> SEQUENCE: 392
acagaagaac agattttacc aattc                                          25

<210> SEQ ID NO 393
<211> LENGTH: 24
<212> TYPE: DNA
<213> ORGANISM: Artificial Sequence
<220> FEATURE:
<223> OTHER INFORMATION: synthetic primer

<400> SEQUENCE: 393
caggattgta ttttgtagtc cacc                                           24

<210> SEQ ID NO 394
<211> LENGTH: 20
<212> TYPE: DNA
<213> ORGANISM: Artificial Sequence
<220> FEATURE:
<223> OTHER INFORMATION: synthetic primer

<400> SEQUENCE: 394
gaaactttcc tcgtttccgc                                                20

<210> SEQ ID NO 395
<211> LENGTH: 20
<212> TYPE: DNA
<213> ORGANISM: Artificial Sequence
<220> FEATURE:
<223> OTHER INFORMATION: synthetic primer

<400> SEQUENCE: 395
ggaaagggaa atggaacagg                                                20

<210> SEQ ID NO 396
<211> LENGTH: 19
<212> TYPE: DNA
<213> ORGANISM: Artificial Sequence
<220> FEATURE:
<223> OTHER INFORMATION: synthetic primer

<400> SEQUENCE: 396
atgcaatcca ccacaggag                                                 19

<210> SEQ ID NO 397
<211> LENGTH: 23
<212> TYPE: DNA
<213> ORGANISM: Artificial Sequence
<220> FEATURE:
<223> OTHER INFORMATION: synthetic primer

<400> SEQUENCE: 397
catgcttcag attgatgtct gag                                            23

<210> SEQ ID NO 398
<211> LENGTH: 20
<212> TYPE: DNA
<213> ORGANISM: Artificial Sequence
<220> FEATURE:
<223> OTHER INFORMATION: synthetic primer
```

-continued

```
<400> SEQUENCE: 398
aagaggtagg gtgaggccag                                              20

<210> SEQ ID NO 399
<211> LENGTH: 20
<212> TYPE: DNA
<213> ORGANISM: Artificial Sequence
<220> FEATURE:
<223> OTHER INFORMATION: synthetic primer

<400> SEQUENCE: 399
ccctggaata atgctcgaag                                              20

<210> SEQ ID NO 400
<211> LENGTH: 20
<212> TYPE: DNA
<213> ORGANISM: Artificial Sequence
<220> FEATURE:
<223> OTHER INFORMATION: synthetic primer

<400> SEQUENCE: 400
ttccagaatt ctctgccacc                                              20

<210> SEQ ID NO 401
<211> LENGTH: 20
<212> TYPE: DNA
<213> ORGANISM: Artificial Sequence
<220> FEATURE:
<223> OTHER INFORMATION: synthetic primer

<400> SEQUENCE: 401
ctgttctttg gtgagagggg                                              20

<210> SEQ ID NO 402
<211> LENGTH: 17
<212> TYPE: DNA
<213> ORGANISM: Artificial Sequence
<220> FEATURE:
<223> OTHER INFORMATION: synthetic primer

<400> SEQUENCE: 402
gaccaggtcc tcagccc                                                 17

<210> SEQ ID NO 403
<211> LENGTH: 20
<212> TYPE: DNA
<213> ORGANISM: Artificial Sequence
<220> FEATURE:
<223> OTHER INFORMATION: synthetic primer

<400> SEQUENCE: 403
ccaaagggtg aagaggaatc                                              20

<210> SEQ ID NO 404
<211> LENGTH: 18
<212> TYPE: DNA
<213> ORGANISM: Artificial Sequence
<220> FEATURE:
<223> OTHER INFORMATION: synthetic primer

<400> SEQUENCE: 404
agggccactg acaaccac                                                18

<210> SEQ ID NO 405
<211> LENGTH: 19
<212> TYPE: DNA
```

```
<213> ORGANISM: Artificial Sequence
<220> FEATURE:
<223> OTHER INFORMATION: synthetic primer

<400> SEQUENCE: 405
gtcagaggca agcagaggc                                                  19

<210> SEQ ID NO 406
<211> LENGTH: 22
<212> TYPE: DNA
<213> ORGANISM: Artificial Sequence
<220> FEATURE:
<223> OTHER INFORMATION: synthetic primer

<400> SEQUENCE: 406
aaacagtcaa gaagaaaacg gc                                              22

<210> SEQ ID NO 407
<211> LENGTH: 21
<212> TYPE: DNA
<213> ORGANISM: Artificial Sequence
<220> FEATURE:
<223> OTHER INFORMATION: synthetic primer

<400> SEQUENCE: 407
ggaatcctat ggctttccaa c                                               21

<210> SEQ ID NO 408
<211> LENGTH: 20
<212> TYPE: DNA
<213> ORGANISM: Artificial Sequence
<220> FEATURE:
<223> OTHER INFORMATION: synthetic primer

<400> SEQUENCE: 408
agacccaaaa cccaaaatgg                                                 20

<210> SEQ ID NO 409
<211> LENGTH: 38
<212> TYPE: DNA
<213> ORGANISM: Artificial Sequence
<220> FEATURE:
<223> OTHER INFORMATION: synthetic primer

<400> SEQUENCE: 409
cucugccugu agccauccuc gugggugguA ugcaaggg                             38

<210> SEQ ID NO 410
<211> LENGTH: 37
<212> TYPE: DNA
<213> ORGANISM: Artificial Sequence
<220> FEATURE:
<223> OTHER INFORMATION: synthetic primer

<400> SEQUENCE: 410
gucgggaggu gucagguucg ugaaagacgu ggggugg                              37

<210> SEQ ID NO 411
<211> LENGTH: 37
<212> TYPE: DNA
<213> ORGANISM: Artificial Sequence
<220> FEATURE:
<223> OTHER INFORMATION: synthetic primer

<400> SEQUENCE: 411
guagcagggg aucucugucg cagcugggca cuguugg                              37
```

<210> SEQ ID NO 412
<211> LENGTH: 40
<212> TYPE: DNA
<213> ORGANISM: Artificial Sequence
<220> FEATURE:
<223> OTHER INFORMATION: synthetic primer

<400> SEQUENCE: 412
agaccacggu accucucauc guaucaagca gcguggguguc                                40

<210> SEQ ID NO 413
<211> LENGTH: 35
<212> TYPE: DNA
<213> ORGANISM: Artificial Sequence
<220> FEATURE:
<223> OTHER INFORMATION: synthetic primer

<400> SEQUENCE: 413
cgaguccugc accccugacc cggucugaga aaccc                                     35

<210> SEQ ID NO 414
<211> LENGTH: 35
<212> TYPE: DNA
<213> ORGANISM: Artificial Sequence
<220> FEATURE:
<223> OTHER INFORMATION: synthetic primer

<400> SEQUENCE: 414
gaccccuacu ccccuaccaa gcacgucaca ccucc                                     35

<210> SEQ ID NO 415
<211> LENGTH: 40
<212> TYPE: DNA
<213> ORGANISM: Artificial Sequence
<220> FEATURE:
<223> OTHER INFORMATION: synthetic primer

<400> SEQUENCE: 415
ucacaccuau acaccccucg uacaucacag gaggaagggg                                40

<210> SEQ ID NO 416
<211> LENGTH: 38
<212> TYPE: DNA
<213> ORGANISM: Artificial Sequence
<220> FEATURE:
<223> OTHER INFORMATION: synthetic primer

<400> SEQUENCE: 416
acuugugacg uccggagaga cacuugaggg ugugcugg                                  38

<210> SEQ ID NO 417
<211> LENGTH: 38
<212> TYPE: DNA
<213> ORGANISM: Artificial Sequence
<220> FEATURE:
<223> OTHER INFORMATION: synthetic primer

<400> SEQUENCE: 417
uuaugucuag uaccgugcuc cguggguggg uggaggug                                  38

<210> SEQ ID NO 418
<211> LENGTH: 38
<212> TYPE: DNA
<213> ORGANISM: Artificial Sequence
<220> FEATURE:
<223> OTHER INFORMATION: synthetic primer

```
<400> SEQUENCE: 418
cuccuccugg aaagcugugc auguccugcu gcccugag                              38

<210> SEQ ID NO 419
<211> LENGTH: 40
<212> TYPE: DNA
<213> ORGANISM: Artificial Sequence
<220> FEATURE:
<223> OTHER INFORMATION: synthetic primer

<400> SEQUENCE: 419
cuuaggggcu ugugggacuu accugggaca ucacucaacc                            40

<210> SEQ ID NO 420
<211> LENGTH: 37
<212> TYPE: DNA
<213> ORGANISM: Artificial Sequence
<220> FEATURE:
<223> OTHER INFORMATION: synthetic primer

<400> SEQUENCE: 420
ccugguguga ggagaaaagg cugcaggcua gcagggc                               37

<210> SEQ ID NO 421
<211> LENGTH: 39
<212> TYPE: DNA
<213> ORGANISM: Artificial Sequence
<220> FEATURE:
<223> OTHER INFORMATION: synthetic primer

<400> SEQUENCE: 421
cugagagaca aggcugcccu auuugcuugc cuguugcug                             39

<210> SEQ ID NO 422
<211> LENGTH: 38
<212> TYPE: DNA
<213> ORGANISM: Artificial Sequence
<220> FEATURE:
<223> OTHER INFORMATION: synthetic primer

<400> SEQUENCE: 422
cuggagccug acccugaggu uaaaauuucc ucccacgg                              38

<210> SEQ ID NO 423
<211> LENGTH: 38
<212> TYPE: DNA
<213> ORGANISM: Artificial Sequence
<220> FEATURE:
<223> OTHER INFORMATION: synthetic primer

<400> SEQUENCE: 423
gccuuuggac agagcucaga gagugggcag guguggug                              38

<210> SEQ ID NO 424
<211> LENGTH: 37
<212> TYPE: DNA
<213> ORGANISM: Artificial Sequence
<220> FEATURE:
<223> OTHER INFORMATION: synthetic primer

<400> SEQUENCE: 424
gaggagcugu gggugagaug cagcagagcc cuccucc                               37

<210> SEQ ID NO 425
<211> LENGTH: 37
<212> TYPE: DNA
```

```
<213> ORGANISM: Artificial Sequence
<220> FEATURE:
<223> OTHER INFORMATION: synthetic primer

<400> SEQUENCE: 425
ggacucacac ugggggaaguu aaggugaggg caggugg                           37

<210> SEQ ID NO 426
<211> LENGTH: 36
<212> TYPE: DNA
<213> ORGANISM: Artificial Sequence
<220> FEATURE:
<223> OTHER INFORMATION: synthetic primer

<400> SEQUENCE: 426
cugcugccac ugucccuguu cccuggaagg aaaggc                             36

<210> SEQ ID NO 427
<211> LENGTH: 37
<212> TYPE: DNA
<213> ORGANISM: Artificial Sequence
<220> FEATURE:
<223> OTHER INFORMATION: synthetic primer

<400> SEQUENCE: 427 gagggaugggg aucugcucuu cuccgaaagc ccgucug                           37

<210> SEQ ID NO 428
<211> LENGTH: 36
<212> TYPE: DNA
<213> ORGANISM: Artificial Sequence
<220> FEATURE:
<223> OTHER INFORMATION: synthetic primer

<400> SEQUENCE: 428
caucaccgcu gggugguguu uccccaggga gucugg                             36

<210> SEQ ID NO 429
<211> LENGTH: 48
<212> TYPE: DNA
<213> ORGANISM: Artificial Sequence
<220> FEATURE:
<223> OTHER INFORMATION: synthetic primer

<400> SEQUENCE: 429
gaaaauaagu guaaaacucc aauggcuuuu guuccuuua ccccuuuc                 48

<210> SEQ ID NO 430
<211> LENGTH: 40
<212> TYPE: DNA
<213> ORGANISM: Artificial Sequence
<220> FEATURE:
<223> OTHER INFORMATION: synthetic primer

<400> SEQUENCE: 430
cucucgauuu gggguuuggu uaaggugcgu gcuuugagag                         40

<210> SEQ ID NO 431
<211> LENGTH: 51
<212> TYPE: DNA
<213> ORGANISM: Artificial Sequence
<220> FEATURE:
<223> OTHER INFORMATION: synthetic primer

<400> SEQUENCE: 431
cucaaagaua gcauguuauu gauugcuguu uucagucaug uauauuugug g            51
```

<210> SEQ ID NO 432
<211> LENGTH: 46
<212> TYPE: DNA
<213> ORGANISM: Artificial Sequence
<220> FEATURE:
<223> OTHER INFORMATION: synthetic primer

<400> SEQUENCE: 432
guuuuaccca acuuuaggcc ugugcucuuc ugcagucuuu auuagc　　　　　　46

<210> SEQ ID NO 433
<211> LENGTH: 40
<212> TYPE: DNA
<213> ORGANISM: Artificial Sequence
<220> FEATURE:
<223> OTHER INFORMATION: synthetic primer

<400> SEQUENCE: 433
ggcuguguuu auuuggcuc uucaugcacc augacugacg　　　　　　40

<210> SEQ ID NO 434
<211> LENGTH: 42
<212> TYPE: DNA
<213> ORGANISM: Artificial Sequence
<220> FEATURE:
<223> OTHER INFORMATION: synthetic primer

<400> SEQUENCE: 434
cuguguuuac uccagaaacc ccugcgguga gcugagauua ug　　　　　　42

<210> SEQ ID NO 435
<211> LENGTH: 46
<212> TYPE: DNA
<213> ORGANISM: Artificial Sequence
<220> FEATURE:
<223> OTHER INFORMATION: synthetic primer

<400> SEQUENCE: 435
guaugaagca agaugguucu aagaaccuug ggcuaagaaa gccuac　　　　　　46

<210> SEQ ID NO 436
<211> LENGTH: 41
<212> TYPE: DNA
<213> ORGANISM: Artificial Sequence
<220> FEATURE:
<223> OTHER INFORMATION: synthetic primer

<400> SEQUENCE: 436
guggcaaaac cccaucucuu gcucauaugc aagaaacucu c　　　　　　41

<210> SEQ ID NO 437
<211> LENGTH: 47
<212> TYPE: DNA
<213> ORGANISM: Artificial Sequence
<220> FEATURE:
<223> OTHER INFORMATION: synthetic primer

<400> SEQUENCE: 437
gaggagaaaa uucauaucag ccacacugau uacuucaucc uggaaag　　　　　　47

<210> SEQ ID NO 438
<211> LENGTH: 46
<212> TYPE: DNA
<213> ORGANISM: Artificial Sequence
<220> FEATURE:
<223> OTHER INFORMATION: synthetic primer -continued

```
<400> SEQUENCE: 438
gaauuaggau auaaggccac caaagGguua uauuagugau cccugc          46

<210> SEQ ID NO 439
<211> LENGTH: 42
<212> TYPE: DNA
<213> ORGANISM: Artificial Sequence
<220> FEATURE:
<223> OTHER INFORMATION: synthetic primer

<400> SEQUENCE: 439
ccugugcuuc acauucgcuu ggcauaaaau ggaauaauug uc              42

<210> SEQ ID NO 440
<211> LENGTH: 41
<212> TYPE: DNA
<213> ORGANISM: Artificial Sequence
<220> FEATURE:
<223> OTHER INFORMATION: synthetic primer

<400> SEQUENCE: 440
cuuugaggca ggGucucacu aaagcuuggc uucaaguugu c               41

<210> SEQ ID NO 441
<211> LENGTH: 45
<212> TYPE: DNA
<213> ORGANISM: Artificial Sequence
<220> FEATURE:
<223> OTHER INFORMATION: synthetic primer

<400> SEQUENCE: 441
ccuucuuuua gccaugagau uucuguuacc cagaaggucu ugaac           45

<210> SEQ ID NO 442
<211> LENGTH: 39
<212> TYPE: DNA
<213> ORGANISM: Artificial Sequence
<220> FEATURE:
<223> OTHER INFORMATION: synthetic primer

<400> SEQUENCE: 442
guguagccca uagguggagg agugagggac gggcaauag                  39

<210> SEQ ID NO 443
<211> LENGTH: 51
<212> TYPE: DNA
<213> ORGANISM: Artificial Sequence
<220> FEATURE:
<223> OTHER INFORMATION: synthetic primer

<400> SEQUENCE: 443
ccauauuuga auacuacagu guuacccuuu guuguuacug cauacacauu g    51

<210> SEQ ID NO 444
<211> LENGTH: 43
<212> TYPE: DNA
<213> ORGANISM: Artificial Sequence
<220> FEATURE:
<223> OTHER INFORMATION: synthetic primer

<400> SEQUENCE: 444
gucaaaugaa acccucgauu gaagcagaga cacaagcaaa guc             43

<210> SEQ ID NO 445
<211> LENGTH: 49
<212> TYPE: DNA
```

```
<213> ORGANISM: Artificial Sequence
<220> FEATURE:
<223> OTHER INFORMATION: synthetic primer

<400> SEQUENCE: 445
ccaauuauag ugaacguuac ucugaaaagu cggaaaauuc aaauaggac          49

<210> SEQ ID NO 446
<211> LENGTH: 42
<212> TYPE: DNA
<213> ORGANISM: Artificial Sequence
<220> FEATURE:
<223> OTHER INFORMATION: synthetic primer

<400> SEQUENCE: 446
ggauguaauc agacgacaca gguucuccau acaggucacg gg                 42

<210> SEQ ID NO 447
<211> LENGTH: 45
<212> TYPE: DNA
<213> ORGANISM: Artificial Sequence
<220> FEATURE:
<223> OTHER INFORMATION: synthetic primer

<400> SEQUENCE: 447
caaacagcuc aaaccaagcg ugcaaaguuu cuucuauuaa ccaag              45

<210> SEQ ID NO 448
<211> LENGTH: 39
<212> TYPE: DNA
<213> ORGANISM: Artificial Sequence
<220> FEATURE:
<223> OTHER INFORMATION: synthetic primer

<400> SEQUENCE: 448
gcaaggaaac caagucagcu agccccagug aucuuccag                     39

<210> SEQ ID NO 449
<211> LENGTH: 47
<212> TYPE: DNA
<213> ORGANISM: Artificial Sequence
<220> FEATURE:
<223> OTHER INFORMATION: synthetic primer

<400> SEQUENCE: 449
cuucuucugc acccaacaaa aaaaggaccu auuagaugau ucagaug            47

<210> SEQ ID NO 450
<211> LENGTH: 40
<212> TYPE: DNA
<213> ORGANISM: Artificial Sequence
<220> FEATURE:
<223> OTHER INFORMATION: synthetic primer

<400> SEQUENCE: 450
gccaauaaau cgaggucagc auucugcuau gcccaaaggg                    40

<210> SEQ ID NO 451
<211> LENGTH: 52
<212> TYPE: DNA
<213> ORGANISM: Artificial Sequence
<220> FEATURE:
<223> OTHER INFORMATION: synthetic primer

<400> SEQUENCE: 451
gcauauuagg ugaagaucug acacuuaaua aggaaucaga ggcuaaaguu ac      52
```

```
<210> SEQ ID NO 452
<211> LENGTH: 39
<212> TYPE: DNA
<213> ORGANISM: Artificial Sequence
<220> FEATURE:
<223> OTHER INFORMATION: synthetic primer

<400> SEQUENCE: 452
cgaggcagga caaugauucg augaccuguu gcaggaaug                      39

<210> SEQ ID NO 453
<211> LENGTH: 45
<212> TYPE: DNA
<213> ORGANISM: Artificial Sequence
<220> FEATURE:
<223> OTHER INFORMATION: synthetic primer

<400> SEQUENCE: 453
gugagucugc cuccaaagga aaaguuugau uacuggaaaa guucg               45

<210> SEQ ID NO 454
<211> LENGTH: 43
<212> TYPE: DNA
<213> ORGANISM: Artificial Sequence
<220> FEATURE:
<223> OTHER INFORMATION: synthetic primer

<400> SEQUENCE: 454
ggucaggaac cuggaaacgu ucaacuaagu ccucagguuc ugg                 43

<210> SEQ ID NO 455
<211> LENGTH: 41
<212> TYPE: DNA
<213> ORGANISM: Artificial Sequence
<220> FEATURE:
<223> OTHER INFORMATION: synthetic primer

<400> SEQUENCE: 455
gguaauggca guguucccau cucccaccua aucucagucc c                   41

<210> SEQ ID NO 456
<211> LENGTH: 44
<212> TYPE: DNA
<213> ORGANISM: Artificial Sequence
<220> FEATURE:
<223> OTHER INFORMATION: synthetic primer

<400> SEQUENCE: 456
gguuugauuc uuguuagagg guuuuuauca aauggcaccu gcug                44

<210> SEQ ID NO 457
<211> LENGTH: 35
<212> TYPE: DNA
<213> ORGANISM: Artificial Sequence
<220> FEATURE:
<223> OTHER INFORMATION: synthetic primer

<400> SEQUENCE: 457
gcccguccuu uccuguuucc ccugacuccg uccag                          35

<210> SEQ ID NO 458
<211> LENGTH: 40
<212> TYPE: DNA
<213> ORGANISM: Artificial Sequence
<220> FEATURE:
<223> OTHER INFORMATION: synthetic primer
```

-continued

```
<400> SEQUENCE: 458
gggcagaauu ccacuugaag accuggaccu ugagggauug                             40

<210> SEQ ID NO 459
<211> LENGTH: 39
<212> TYPE: DNA
<213> ORGANISM: Artificial Sequence
<220> FEATURE:
<223> OTHER INFORMATION: synthetic primer

<400> SEQUENCE: 459
cagacagcag uuccgauggc ccuggaccca uuuuagacc                              39

<210> SEQ ID NO 460
<211> LENGTH: 40
<212> TYPE: DNA
<213> ORGANISM: Artificial Sequence
<220> FEATURE:
<223> OTHER INFORMATION: synthetic primer

<400> SEQUENCE: 460
ggggacagcu cuacagcacu agcacaugca uccuucaugg                             40

<210> SEQ ID NO 461
<211> LENGTH: 40
<212> TYPE: DNA
<213> ORGANISM: Artificial Sequence
<220> FEATURE:
<223> OTHER INFORMATION: synthetic primer

<400> SEQUENCE: 461 cccccucucuu ccuucacuug gaaagggcgu caucaguuuc                            40

<210> SEQ ID NO 462
<211> LENGTH: 40
<212> TYPE: DNA
<213> ORGANISM: Artificial Sequence
<220> FEATURE:
<223> OTHER INFORMATION: synthetic primer

<400> SEQUENCE: 462
cccacaccag gacagaagac cccugggaaa ugauccuacc                             40

<210> SEQ ID NO 463
<211> LENGTH: 37
<212> TYPE: DNA
<213> ORGANISM: Artificial Sequence
<220> FEATURE:
<223> OTHER INFORMATION: synthetic primer

<400> SEQUENCE: 463 cuugcccgc ucugucuccu cgcuuccucc gugugug                                 37

<210> SEQ ID NO 464
<211> LENGTH: 36
<212> TYPE: DNA
<213> ORGANISM: Artificial Sequence
<220> FEATURE:
<223> OTHER INFORMATION: synthetic primer

<400> SEQUENCE: 464
cugcugaggc ugggcuccuc aagaggaccu ggaccg                                 36

<210> SEQ ID NO 465
<211> LENGTH: 52
<212> TYPE: DNA
```

```
<213> ORGANISM: Artificial Sequence
<220> FEATURE:
<223> OTHER INFORMATION: synthetic primer

<400> SEQUENCE: 465
gagagagaac uuuucgacau auuuccggau cccuagcuau ucuuaaucca ac      52

<210> SEQ ID NO 466
<211> LENGTH: 49
<212> TYPE: DNA
<213> ORGANISM: Artificial Sequence
<220> FEATURE:
<223> OTHER INFORMATION: synthetic primer

<400> SEQUENCE: 466
gcuaagauag ggcacagagc uccagagucc cugagagucu agaguaaug           49

<210> SEQ ID NO 467
<211> LENGTH: 44
<212> TYPE: DNA
<213> ORGANISM: Artificial Sequence
<220> FEATURE:
<223> OTHER INFORMATION: synthetic primer

<400> SEQUENCE: 467
cugugaaauu accaugugaa uucccuccca cagcaugacc uacc                44

<210> SEQ ID NO 468
<211> LENGTH: 39
<212> TYPE: DNA
<213> ORGANISM: Artificial Sequence
<220> FEATURE:
<223> OTHER INFORMATION: synthetic primer

<400> SEQUENCE: 468
ggcuccaggu uguuguuaua gcaaggugcc gucuccucc                      39

<210> SEQ ID NO 469
<211> LENGTH: 41
<212> TYPE: DNA
<213> ORGANISM: Artificial Sequence
<220> FEATURE:
<223> OTHER INFORMATION: synthetic primer

<400> SEQUENCE: 469
cagaagccga acagugauga agaggugauu uguguuccug c                   41

<210> SEQ ID NO 470
<211> LENGTH: 40
<212> TYPE: DNA
<213> ORGANISM: Artificial Sequence
<220> FEATURE:
<223> OTHER INFORMATION: synthetic primer

<400> SEQUENCE: 470
caaguuuucc ggcaacaaau uaucauuugg cuuuccccac                     40

<210> SEQ ID NO 471
<211> LENGTH: 44
<212> TYPE: DNA
<213> ORGANISM: Artificial Sequence
<220> FEATURE:
<223> OTHER INFORMATION: synthetic primer

<400> SEQUENCE: 471
gaaugaccac acugcugugg ucuccaaaau auaugccaaa gaag                44
```

<210> SEQ ID NO 472
<211> LENGTH: 38
<212> TYPE: DNA
<213> ORGANISM: Artificial Sequence
<220> FEATURE:
<223> OTHER INFORMATION: synthetic primer

<400> SEQUENCE: 472
gaacgggcca uuagcaguug gccauggaau cugucagc                    38

<210> SEQ ID NO 473
<211> LENGTH: 38
<212> TYPE: DNA
<213> ORGANISM: Artificial Sequence
<220> FEATURE:
<223> OTHER INFORMATION: synthetic primer

<400> SEQUENCE: 473
ccagaguccu ugcaagcugu uuccagcau ggugaggg                     38

<210> SEQ ID NO 474
<211> LENGTH: 40
<212> TYPE: DNA
<213> ORGANISM: Artificial Sequence
<220> FEATURE:
<223> OTHER INFORMATION: synthetic primer

<400> SEQUENCE: 474
gcccaccuuu ucucaugucu agcauguggc accaucucac                  40

<210> SEQ ID NO 475
<211> LENGTH: 37
<212> TYPE: DNA
<213> ORGANISM: Artificial Sequence
<220> FEATURE:
<223> OTHER INFORMATION: synthetic primer

<400> SEQUENCE: 475
gucugcgcuc cugggauagc augugcccu ccuucug                      37

<210> SEQ ID NO 476
<211> LENGTH: 39
<212> TYPE: DNA
<213> ORGANISM: Artificial Sequence
<220> FEATURE:
<223> OTHER INFORMATION: synthetic primer

<400> SEQUENCE: 476
cugccuuccc acuagcugua aauucggaug cagagcuuc                   39

<210> SEQ ID NO 477
<211> LENGTH: 45
<212> TYPE: DNA
<213> ORGANISM: Artificial Sequence
<220> FEATURE:
<223> OTHER INFORMATION: synthetic primer

<400> SEQUENCE: 477
ccucugacau gcaaguauuu ucuuuucguc uguguguguc acucg             45

<210> SEQ ID NO 478
<211> LENGTH: 40
<212> TYPE: DNA
<213> ORGANISM: Artificial Sequence
<220> FEATURE:
<223> OTHER INFORMATION: synthetic primer -continued

```
<400> SEQUENCE: 478
ggcugcucuu agccaaacag gcaagggauu gugauuguuc                    40

<210> SEQ ID NO 479
<211> LENGTH: 45
<212> TYPE: DNA
<213> ORGANISM: Artificial Sequence
<220> FEATURE:
<223> OTHER INFORMATION: synthetic primer

<400> SEQUENCE: 479
gcaucucaug ucacuguguu cuggcaaugc caucuuuauc auuuc              45

<210> SEQ ID NO 480
<211> LENGTH: 46
<212> TYPE: DNA
<213> ORGANISM: Artificial Sequence
<220> FEATURE:
<223> OTHER INFORMATION: synthetic primer

<400> SEQUENCE: 480
gggaaaauaa ccaucuagug aaacucagac cccugcuccu auagcc             46

<210> SEQ ID NO 481
<211> LENGTH: 44
<212> TYPE: DNA
<213> ORGANISM: Artificial Sequence
<220> FEATURE:
<223> OTHER INFORMATION: synthetic primer

<400> SEQUENCE: 481
cacuauggcu cuauuuuaca uggaccugca uucaggaaaa gugg               44

<210> SEQ ID NO 482
<211> LENGTH: 39
<212> TYPE: DNA
<213> ORGANISM: Artificial Sequence
<220> FEATURE:
<223> OTHER INFORMATION: synthetic primer

<400> SEQUENCE: 482
gccagucucc aguguccaau ugcaaacacu gaaguuggg                     39

<210> SEQ ID NO 483
<211> LENGTH: 38
<212> TYPE: DNA
<213> ORGANISM: Artificial Sequence
<220> FEATURE:
<223> OTHER INFORMATION: synthetic primer

<400> SEQUENCE: 483
gauacccagg accaagccac auccugcaug ggauggug                      38

<210> SEQ ID NO 484
<211> LENGTH: 43
<212> TYPE: DNA
<213> ORGANISM: Artificial Sequence
<220> FEATURE:
<223> OTHER INFORMATION: synthetic primer

<400> SEQUENCE: 484
gugugggcua aauguaccau caagaucugu guugggugac cag                43

<210> SEQ ID NO 485
<211> LENGTH: 41
<212> TYPE: DNA
```

```
<213> ORGANISM: Artificial Sequence
<220> FEATURE:
<223> OTHER INFORMATION: synthetic primer

<400> SEQUENCE: 485
cacccugugu cugccacuua cacucccacc accacaguua g                   41

<210> SEQ ID NO 486
<211> LENGTH: 40
<212> TYPE: DNA
<213> ORGANISM: Artificial Sequence
<220> FEATURE:
<223> OTHER INFORMATION: synthetic primer

<400> SEQUENCE: 486
ggggucuuuu gcuuccuucu agucugcgua cuuuccuggc                     40

<210> SEQ ID NO 487
<211> LENGTH: 42
<212> TYPE: DNA
<213> ORGANISM: Artificial Sequence
<220> FEATURE:
<223> OTHER INFORMATION: synthetic primer

<400> SEQUENCE: 487
cguagagaau caccuggccu uccugagaga acaaaacucu gg                  42

<210> SEQ ID NO 488
<211> LENGTH: 39
<212> TYPE: DNA
<213> ORGANISM: Artificial Sequence
<220> FEATURE:
<223> OTHER INFORMATION: synthetic primer

<400> SEQUENCE: 488
cguguaccau ucugugagcg augggauggg ccuguauuc                      39

<210> SEQ ID NO 489
<211> LENGTH: 40
<212> TYPE: DNA
<213> ORGANISM: Artificial Sequence
<220> FEATURE:
<223> OTHER INFORMATION: synthetic primer

<400> SEQUENCE: 489
caggguaaac agggaacagg guagaaucca cagugcccag                     40

<210> SEQ ID NO 490
<211> LENGTH: 44
<212> TYPE: DNA
<213> ORGANISM: Artificial Sequence
<220> FEATURE:
<223> OTHER INFORMATION: synthetic primer

<400> SEQUENCE: 490
gguuggagag gaaggacgcu gcuuuauagg accuuugacu guug                44

<210> SEQ ID NO 491
<211> LENGTH: 40
<212> TYPE: DNA
<213> ORGANISM: Artificial Sequence
<220> FEATURE:
<223> OTHER INFORMATION: synthetic primer

<400> SEQUENCE: 491
ccccaguguu gggacuguua caaggugauu uugaggugggg                    40
```

```
<210> SEQ ID NO 492
<211> LENGTH: 42
<212> TYPE: DNA
<213> ORGANISM: Artificial Sequence
<220> FEATURE:
<223> OTHER INFORMATION: synthetic primer

<400> SEQUENCE: 492
gaugcuggaa acuuugggaa gagaaagcug uuucuuccca ag                    42

<210> SEQ ID NO 493
<211> LENGTH: 41
<212> TYPE: DNA
<213> ORGANISM: Artificial Sequence
<220> FEATURE:
<223> OTHER INFORMATION: synthetic primer

<400> SEQUENCE: 493
ggacaauugg gaguagccag caagcugcag accuaccugu c                     41

<210> SEQ ID NO 494
<211> LENGTH: 39
<212> TYPE: DNA
<213> ORGANISM: Artificial Sequence
<220> FEATURE:
<223> OTHER INFORMATION: synthetic primer

<400> SEQUENCE: 494
cgcugugaga acugcuugau ggagguagaa gcugggaag                        39

<210> SEQ ID NO 495
<211> LENGTH: 43
<212> TYPE: DNA
<213> ORGANISM: Artificial Sequence
<220> FEATURE:
<223> OTHER INFORMATION: synthetic primer

<400> SEQUENCE: 495
gucaucagcu cauauggga uuuucuguug gacacagucu cuc                    43

<210> SEQ ID NO 496
<211> LENGTH: 45
<212> TYPE: DNA
<213> ORGANISM: Artificial Sequence
<220> FEATURE:
<223> OTHER INFORMATION: synthetic primer

<400> SEQUENCE: 496
ggguggaaaa gaaacuaacc ucuuaugacu gagauggucu cuugg                 45

<210> SEQ ID NO 497
<211> LENGTH: 38
<212> TYPE: DNA
<213> ORGANISM: Artificial Sequence
<220> FEATURE:
<223> OTHER INFORMATION: synthetic primer

<400> SEQUENCE: 497
ccagggacuu ugcuucucuu ucccggccuc caaaauac                         38

<210> SEQ ID NO 498
<211> LENGTH: 44
<212> TYPE: DNA
<213> ORGANISM: Artificial Sequence
<220> FEATURE:
<223> OTHER INFORMATION: synthetic primer
```

-continued

<400> SEQUENCE: 498
ggcaagagag agaugguugc gaaaccucuu uucuucuuac agcc         44

<210> SEQ ID NO 499
<211> LENGTH: 40
<212> TYPE: DNA
<213> ORGANISM: Artificial Sequence
<220> FEATURE:
<223> OTHER INFORMATION: synthetic primer

<400> SEQUENCE: 499
cucacucaca gagcccuugc gcaagggcuc ugugagugag              40

<210> SEQ ID NO 500
<211> LENGTH: 40
<212> TYPE: DNA
<213> ORGANISM: Artificial Sequence
<220> FEATURE:
<223> OTHER INFORMATION: synthetic primer

<400> SEQUENCE: 500
gcaccacaca ugcacagauc uaaccaugcu cugccugaag              40

<210> SEQ ID NO 501
<211> LENGTH: 40
<212> TYPE: DNA
<213> ORGANISM: Artificial Sequence
<220> FEATURE:
<223> OTHER INFORMATION: synthetic primer

<400> SEQUENCE: 501
ggcucagaag caaguuugaa agcuuaaggu aagccugggg              40

<210> SEQ ID NO 502
<211> LENGTH: 41
<212> TYPE: DNA
<213> ORGANISM: Artificial Sequence
<220> FEATURE:
<223> OTHER INFORMATION: synthetic primer

<400> SEQUENCE: 502 gauuccucu gagucccugg cuuuucggc caucuugauu c              41

<210> SEQ ID NO 503
<211> LENGTH: 46
<212> TYPE: DNA
<213> ORGANISM: Artificial Sequence
<220> FEATURE:
<223> OTHER INFORMATION: synthetic primer

<400> SEQUENCE: 503
guucauuucu uaaguuccca ggcuguccuu agauacuugg gaccug       46

<210> SEQ ID NO 504
<211> LENGTH: 41
<212> TYPE: DNA
<213> ORGANISM: Artificial Sequence
<220> FEATURE:
<223> OTHER INFORMATION: synthetic primer

<400> SEQUENCE: 504
gaagacuuug ucugugagcc acccucaguc acgucucuuc c            41

<210> SEQ ID NO 505
<211> LENGTH: 45
<212> TYPE: DNA

<213> ORGANISM: Artificial Sequence
<220> FEATURE:
<223> OTHER INFORMATION: synthetic primer

<400> SEQUENCE: 505
cuuggcuaug ggaguuugug cccagaagaa auggcauaa uguag         45

<210> SEQ ID NO 506
<211> LENGTH: 37
<212> TYPE: DNA
<213> ORGANISM: Artificial Sequence
<220> FEATURE:
<223> OTHER INFORMATION: synthetic primer

<400> SEQUENCE: 506
gggcaaccga aaccagucu accaggucug caccucc         37

<210> SEQ ID NO 507
<211> LENGTH: 43
<212> TYPE: DNA
<213> ORGANISM: Artificial Sequence
<220> FEATURE:
<223> OTHER INFORMATION: synthetic primer

<400> SEQUENCE: 507
gaaguaauaa ucaaggggcu ggaggggaau uuuaucguga aag         43

<210> SEQ ID NO 508
<211> LENGTH: 40
<212> TYPE: DNA
<213> ORGANISM: Artificial Sequence
<220> FEATURE:
<223> OTHER INFORMATION: synthetic primer

<400> SEQUENCE: 508
gaccucucuu cucccacugc aggugugacu uugaggcagc         40

<210> SEQ ID NO 509
<211> LENGTH: 40
<212> TYPE: DNA
<213> ORGANISM: Artificial Sequence
<220> FEATURE:
<223> OTHER INFORMATION: synthetic primer

<400> SEQUENCE: 509
guuauuggcc cugaccuuca cccacaucuc cuacccucag         40

<210> SEQ ID NO 510
<211> LENGTH: 40
<212> TYPE: DNA
<213> ORGANISM: Artificial Sequence
<220> FEATURE:
<223> OTHER INFORMATION: synthetic primer

<400> SEQUENCE: 510
cccacacgga guucucacuu gcguacagca gcacauuagg         40

<210> SEQ ID NO 511
<211> LENGTH: 39
<212> TYPE: DNA
<213> ORGANISM: Artificial Sequence
<220> FEATURE:
<223> OTHER INFORMATION: synthetic primer

<400> SEQUENCE: 511
gugagugagg cuaggggcuc gggcaggaga ggaagauug         39

<210> SEQ ID NO 512
<211> LENGTH: 39
<212> TYPE: DNA
<213> ORGANISM: Artificial Sequence
<220> FEATURE:
<223> OTHER INFORMATION: synthetic primer

<400> SEQUENCE: 512
ccacggugcu uugguaaaga cugccuuuag cccaaccag                39

<210> SEQ ID NO 513
<211> LENGTH: 38
<212> TYPE: DNA
<213> ORGANISM: Artificial Sequence
<220> FEATURE:
<223> OTHER INFORMATION: synthetic primer

<400> SEQUENCE: 513
cccuaccccu uccaggaccu guagcuaguu ggggugcc                 38

<210> SEQ ID NO 514
<211> LENGTH: 40
<212> TYPE: DNA
<213> ORGANISM: Artificial Sequence
<220> FEATURE:
<223> OTHER INFORMATION: synthetic primer

<400> SEQUENCE: 514
ccuaaucugc uucgcucugc acagagcaag acucugccac              40

<210> SEQ ID NO 515
<211> LENGTH: 38
<212> TYPE: DNA
<213> ORGANISM: Artificial Sequence
<220> FEATURE:
<223> OTHER INFORMATION: synthetic primer

<400> SEQUENCE: 515
caucccagca gcuucugcga acgguagcuc ccuuccuc                38

<210> SEQ ID NO 516
<211> LENGTH: 40
<212> TYPE: DNA
<213> ORGANISM: Artificial Sequence
<220> FEATURE:
<223> OTHER INFORMATION: synthetic primer

<400> SEQUENCE: 516
gugcucgugg uuacagcuga uuaggagggc uguuuugagg              40

<210> SEQ ID NO 517
<211> LENGTH: 38
<212> TYPE: DNA
<213> ORGANISM: Artificial Sequence
<220> FEATURE:
<223> OTHER INFORMATION: synthetic primer

<400> SEQUENCE: 517
ggugccaggc ucucugaggu uccucagcau cgaccuug                38

<210> SEQ ID NO 518
<211> LENGTH: 42
<212> TYPE: DNA
<213> ORGANISM: Artificial Sequence
<220> FEATURE:
<223> OTHER INFORMATION: synthetic primer

```
<400> SEQUENCE: 518
cucuuccccu uccugacccu ccacccuuug aaguagguac ag                          42

<210> SEQ ID NO 519
<211> LENGTH: 40
<212> TYPE: DNA
<213> ORGANISM: Artificial Sequence
<220> FEATURE:
<223> OTHER INFORMATION: synthetic primer

<400> SEQUENCE: 519
ggucagccuu uccaaaagcu cugccagcuc ucuucucagg                             40

<210> SEQ ID NO 520
<211> LENGTH: 38
<212> TYPE: DNA
<213> ORGANISM: Artificial Sequence
<220> FEATURE:
<223> OTHER INFORMATION: synthetic primer

<400> SEQUENCE: 520
ggucccuuag cugguggggau accagcucuu ccccaacc                              38

<210> SEQ ID NO 521
<211> LENGTH: 42
<212> TYPE: DNA
<213> ORGANISM: Artificial Sequence
<220> FEATURE:
<223> OTHER INFORMATION: synthetic primer

<400> SEQUENCE: 521
gaaugaaagg acgugaccca uuccucugac ugcuggaaau ag                          42

<210> SEQ ID NO 522
<211> LENGTH: 41
<212> TYPE: DNA
<213> ORGANISM: Artificial Sequence
<220> FEATURE:
<223> OTHER INFORMATION: synthetic primer

<400> SEQUENCE: 522
cacucauucc aaagcaucug gauaucugca gucagccugg g                           41

<210> SEQ ID NO 523
<211> LENGTH: 40
<212> TYPE: DNA
<213> ORGANISM: Artificial Sequence
<220> FEATURE:
<223> OTHER INFORMATION: synthetic primer

<400> SEQUENCE: 523
cugagacccc uucccucuuc gcguuuaaau ucuucccugg                             40

<210> SEQ ID NO 524
<211> LENGTH: 44
<212> TYPE: DNA
<213> ORGANISM: Artificial Sequence
<220> FEATURE:
<223> OTHER INFORMATION: synthetic primer

<400> SEQUENCE: 524
ccuacauuug ucucguguag ucaucagcug aagagcugag gacc                        44

<210> SEQ ID NO 525
<211> LENGTH: 39
<212> TYPE: DNA
```

<213> ORGANISM: Artificial Sequence
<220> FEATURE:
<223> OTHER INFORMATION: synthetic primer

<400> SEQUENCE: 525
gaaucuccgu agcgcugcuu cugccugugu ucugagcug                   39

<210> SEQ ID NO 526
<211> LENGTH: 39
<212> TYPE: DNA
<213> ORGANISM: Artificial Sequence
<220> FEATURE:
<223> OTHER INFORMATION: synthetic primer

<400> SEQUENCE: 526
ccccacucgc aauaggauga ccccaagccu uguuucuuc                   39

<210> SEQ ID NO 527
<211> LENGTH: 44
<212> TYPE: DNA
<213> ORGANISM: Artificial Sequence
<220> FEATURE:
<223> OTHER INFORMATION: synthetic primer

<400> SEQUENCE: 527
ccugaauggu uucauuuggu uucucggucu caaaaguaca aacc             44

<210> SEQ ID NO 528
<211> LENGTH: 43
<212> TYPE: DNA
<213> ORGANISM: Artificial Sequence
<220> FEATURE:
<223> OTHER INFORMATION: synthetic primer

<400> SEQUENCE: 528
cuguaggcag acuuaagccc acguuugcca acuccuagcu uac              43

<210> SEQ ID NO 529
<211> LENGTH: 41
<212> TYPE: DNA
<213> ORGANISM: Artificial Sequence
<220> FEATURE:
<223> OTHER INFORMATION: synthetic primer

<400> SEQUENCE: 529
ggaucaggac aguuacagcc uuagaggaaa gccaccugcu c                41

<210> SEQ ID NO 530
<211> LENGTH: 40
<212> TYPE: DNA
<213> ORGANISM: Artificial Sequence
<220> FEATURE:
<223> OTHER INFORMATION: synthetic primer

<400> SEQUENCE: 530
caaggcagag gaguugcuug acauggccug ugucugcuuc                  40

<210> SEQ ID NO 531
<211> LENGTH: 45
<212> TYPE: DNA
<213> ORGANISM: Artificial Sequence
<220> FEATURE:
<223> OTHER INFORMATION: synthetic primer

<400> SEQUENCE: 531
cccuugugca gaguguuugu gacuggaaga aaauaaccaa guuuc            45

```
<210> SEQ ID NO 532
<211> LENGTH: 42
<212> TYPE: DNA
<213> ORGANISM: Artificial Sequence
<220> FEATURE:
<223> OTHER INFORMATION: synthetic primer

<400> SEQUENCE: 532
cugagcacac uuccucucu gaaugcuaac accaacagug gc                            42

<210> SEQ ID NO 533
<211> LENGTH: 40
<212> TYPE: DNA
<213> ORGANISM: Artificial Sequence
<220> FEATURE:
<223> OTHER INFORMATION: synthetic primer

<400> SEQUENCE: 533
cccaaagcca gaguagcaaa agggaacaag aagugcaucg                              40

<210> SEQ ID NO 534
<211> LENGTH: 50
<212> TYPE: DNA
<213> ORGANISM: Artificial Sequence
<220> FEATURE:
<223> OTHER INFORMATION: synthetic primer

<400> SEQUENCE: 534
gaccauucuu ugauacagau aaagguuaaa agguacuggu ggaguauuug                   50

<210> SEQ ID NO 535
<211> LENGTH: 40
<212> TYPE: DNA
<213> ORGANISM: Artificial Sequence
<220> FEATURE:
<223> OTHER INFORMATION: synthetic primer

<400> SEQUENCE: 535
gucuuugcua augccaugca ucuuuggagc aggaacaaug                              40

<210> SEQ ID NO 536
<211> LENGTH: 41
<212> TYPE: DNA
<213> ORGANISM: Artificial Sequence
<220> FEATURE:
<223> OTHER INFORMATION: synthetic primer

<400> SEQUENCE: 536
cuugagaggg cauugcuucu agaaggaagg aaaauuuggu g                            41

<210> SEQ ID NO 537
<211> LENGTH: 41
<212> TYPE: DNA
<213> ORGANISM: Artificial Sequence
<220> FEATURE:
<223> OTHER INFORMATION: synthetic primer

<400> SEQUENCE: 537
gguaacaagg uggcaaccac aacuucuugc acauggcuuu c                            41

<210> SEQ ID NO 538
<211> LENGTH: 38
<212> TYPE: DNA
<213> ORGANISM: Artificial Sequence
<220> FEATURE:
<223> OTHER INFORMATION: synthetic primer
```

-continued

```
<400> SEQUENCE: 538
guggcauucg ugcuccuccc uagggcugug cuguuug                          38

<210> SEQ ID NO 539
<211> LENGTH: 40
<212> TYPE: DNA
<213> ORGANISM: Artificial Sequence
<220> FEATURE:
<223> OTHER INFORMATION: synthetic primer

<400> SEQUENCE: 539
cucccggguu cacaccauug guuaaauucc uuugaagugc                       40

<210> SEQ ID NO 540
<211> LENGTH: 43
<212> TYPE: DNA
<213> ORGANISM: Artificial Sequence
<220> FEATURE:
<223> OTHER INFORMATION: synthetic primer

<400> SEQUENCE: 540
cggugcuaau ugccaucuaa ugccauauau cuuggcauuu auc                   43

<210> SEQ ID NO 541
<211> LENGTH: 44
<212> TYPE: DNA
<213> ORGANISM: Artificial Sequence
<220> FEATURE:
<223> OTHER INFORMATION: synthetic primer

<400> SEQUENCE: 541
gcugaagaca gguuaaaagc uuaaauggaa gcauuuggga auac                  44

<210> SEQ ID NO 542
<211> LENGTH: 40
<212> TYPE: DNA
<213> ORGANISM: Artificial Sequence
<220> FEATURE:
<223> OTHER INFORMATION: synthetic primer

<400> SEQUENCE: 542
caaccauacu gcccauaugg ugcaugguuu gugcauacag                       40

<210> SEQ ID NO 543
<211> LENGTH: 46
<212> TYPE: DNA
<213> ORGANISM: Artificial Sequence
<220> FEATURE:
<223> OTHER INFORMATION: synthetic primer

<400> SEQUENCE: 543
cccugaagca aacaaguguu ucaaauucca cauauuucug gcuaac                46

<210> SEQ ID NO 544
<211> LENGTH: 46
<212> TYPE: DNA
<213> ORGANISM: Artificial Sequence
<220> FEATURE:
<223> OTHER INFORMATION: synthetic primer

<400> SEQUENCE: 544
gugcaguucu cucagguguc aauuuucauc uuaauuacga aucugc                46

<210> SEQ ID NO 545
<211> LENGTH: 49
<212> TYPE: DNA
```

<213> ORGANISM: Artificial Sequence
<220> FEATURE:
<223> OTHER INFORMATION: synthetic primer

<400> SEQUENCE: 545
gacuuacucg uuucuuucc ucugaaagcu uuucuaaaau gccuaaucc         49

<210> SEQ ID NO 546
<211> LENGTH: 44
<212> TYPE: DNA
<213> ORGANISM: Artificial Sequence
<220> FEATURE:
<223> OTHER INFORMATION: synthetic primer

<400> SEQUENCE: 546
cugugccuaa aaugugaaua auggaacauu auaucagugc gggg              44

<210> SEQ ID NO 547
<211> LENGTH: 41
<212> TYPE: DNA
<213> ORGANISM: Artificial Sequence
<220> FEATURE:
<223> OTHER INFORMATION: synthetic primer

<400> SEQUENCE: 547
cccuuaauga uggauauugg cuugcuugaa ucugggaggu g                 41

<210> SEQ ID NO 548
<211> LENGTH: 40
<212> TYPE: DNA
<213> ORGANISM: Artificial Sequence
<220> FEATURE:
<223> OTHER INFORMATION: synthetic primer

<400> SEQUENCE: 548
guccaggcaa gagucuccu auaagccauu uggguucgug                    40

<210> SEQ ID NO 549
<211> LENGTH: 46
<212> TYPE: DNA
<213> ORGANISM: Artificial Sequence
<220> FEATURE:
<223> OTHER INFORMATION: synthetic primer

<400> SEQUENCE: 549
ggaaccagcu agacaccagg ugguuacugu cacaaaauaa aacuug            46

<210> SEQ ID NO 550
<211> LENGTH: 47
<212> TYPE: DNA
<213> ORGANISM: Artificial Sequence
<220> FEATURE:
<223> OTHER INFORMATION: synthetic primer

<400> SEQUENCE: 550
gaaauggaag cauguuauuu acugcgguga cagaguaaga ccuugcc           47

<210> SEQ ID NO 551
<211> LENGTH: 43
<212> TYPE: DNA
<213> ORGANISM: Artificial Sequence
<220> FEATURE:
<223> OTHER INFORMATION: synthetic primer

<400> SEQUENCE: 551
gugaagccac ugcuaccugg uuuauacccg auuuucucca cug               43

```
<210> SEQ ID NO 552
<211> LENGTH: 42
<212> TYPE: DNA
<213> ORGANISM: Artificial Sequence
<220> FEATURE:
<223> OTHER INFORMATION: synthetic primer

<400> SEQUENCE: 552
guggcagagg cgacuauuuu cauuuuaugg uguugguguu gg                              42

<210> SEQ ID NO 553
<211> LENGTH: 45
<212> TYPE: DNA
<213> ORGANISM: Artificial Sequence
<220> FEATURE:
<223> OTHER INFORMATION: synthetic primer

<400> SEQUENCE: 553
ccugaacacu gauggaaaug uugaagugua agagguugau uuucc                          45

<210> SEQ ID NO 554
<211> LENGTH: 44
<212> TYPE: DNA
<213> ORGANISM: Artificial Sequence
<220> FEATURE:
<223> OTHER INFORMATION: synthetic primer

<400> SEQUENCE: 554
gcuacguuuc cuuucaagcu accaaaggau caaaauugcu ucag                           44

<210> SEQ ID NO 555
<211> LENGTH: 39
<212> TYPE: DNA
<213> ORGANISM: Artificial Sequence
<220> FEATURE:
<223> OTHER INFORMATION: synthetic primer

<400> SEQUENCE: 555
ggaagauagc ccgcgaccug aguugguagg auugugagg                                 39
```

METHODS AND COMPOSITIONS FOR PERFORMING LOW BACKGROUND MULTIPLEX NUCLEIC ACID AMPLIFICATION REACTIONS

CROSS-REFERENCE TO RELATED APPLICATIONS

This applications claims benefit of priority to U.S. provisional application 60/844,259, filed Sep. 12, 2006, which is herein incorporated by reference.

GOVERNMENT RIGHTS

This invention was made with Government support under contract 2P01 HG000205 awarded by the National Institutes of Health. The Government has certain rights to this invention.

BACKGROUND

To increase assay throughput and allow more efficient use of DNA samples, simultaneous amplification of many target nucleic acids in a sample of interest can be carried out by combining many specific primer pairs with a sample of interest and then subjecting the sample to polymerase chain reaction (PCR) conditions in a process known in the art as multiplex PCR. However, when multiple specific primer pairs are added to the same PCR reaction, non-target amplification products may be generated, with the risk of generating such products increasing with increasing numbers of specific primer pairs employed. These non-target "amplicons" significantly limit the utility of the amplification product for further analysis and/or assays. Even with careful attention paid to the design of the primers, multiplex PCR is typically limited to 10-20 specific primer pairs in a single multiplex reaction before amplification yield is compromised by the accumulation of non-target amplicons (see, e.g., Syvanen, A C., *Toward genome-wide SNP genotyping*. Nature Genetics (2005) 37 Suppl: p. S5-10; and Broude, N. E., et al., *Multiplex allele-specific target amplification based on PCR suppression*. PNAS (2001) 98(1): p. 206-11). As such, there is a continued need for improved methods to reduce the impact of non-target amplicon generation in multiplex PCR.

SUMMARY

Methods and compositions for performing low background multiplex nucleic acid amplification reactions are provided. Aspects of the invention include contacting a nucleic acid sample with two or more primer pairs for two or more target nucleic acid sequences under template dependent primer extension reaction conditions, e.g., polymerase chain reaction (PCR) conditions. The resultant amplified composition is then contacted with target nucleic acid circularizing reagents, and product circularized target nucleic acids are then selected, e.g., specifically amplified. Also provided are systems and kits that find use in practicing embodiments of the inventions.

BRIEF DESCRIPTION OF THE FIGURES

The accompanying drawings illustrate embodiments of the invention and, together with the description, serve to explain the invention. These drawings are offered by way of illustration and not by way of limitation.

FIG. 12 shows the sequence of the forward and reverse amplification primers specific for exons of the human genes of interest as well as the circularization template oligonucleotides (listed as Gene-Collector Probes). Human genes of interest are as follows: v-akt murine thymoma viral oncogene homolog 1 (AKT-1); v-akt murine thymoma viral oncogene homolog 2 (AKT-2); adenomatosis polyposis coli (APC); epidermal growth factor receptor (EGFR); FK506 binding protein 12-rapamycin associated protein 1 (FRAP); v-Ki-ras2 Kirsten rat sarcoma viral oncogene homolog (KRas); MAP/microtubule affinity-regulating kinase 3 (MARK3); SMAD, mothers against DPP homolog 4 (SMAD4); transforming growth factor, beta receptor II (TGF-beta R2); and tumor protein p53 (TP53).

DEFINITIONS

Figure 1:
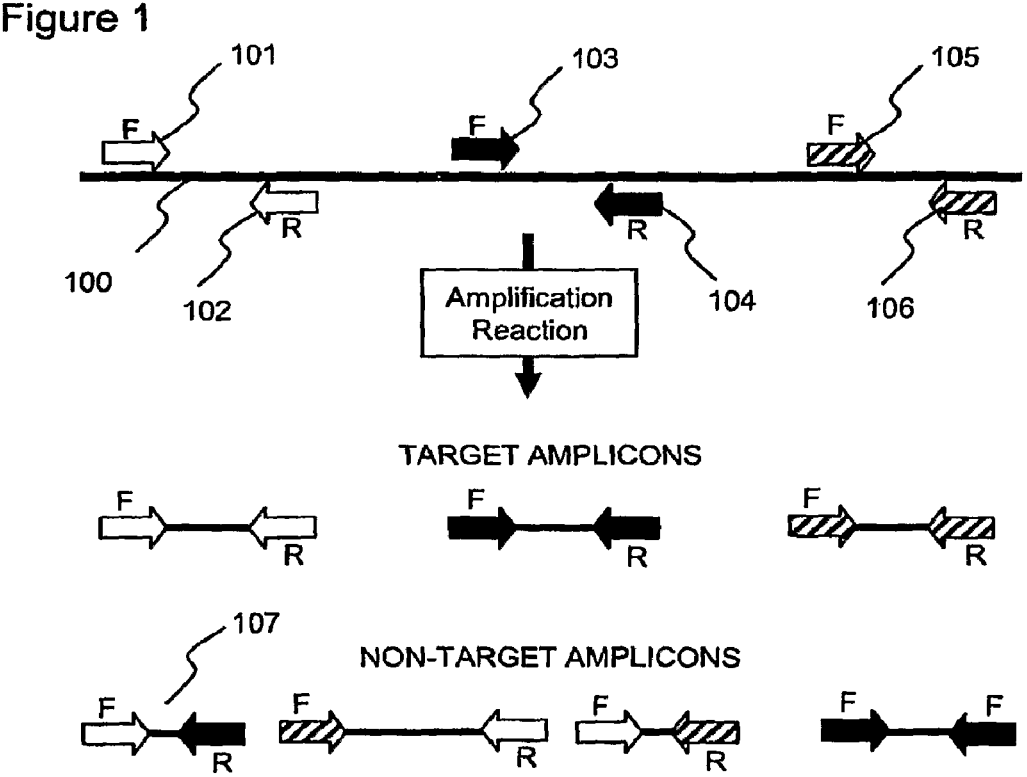
FIG. 1 illustrates target and non-target amplicons that are generated in a multiplex PCR reaction.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" or "oligo" as used herein denotes single-stranded nucleotide multimers of from about 10 up to about 400 nucleotides in length, e.g., from about 25 to about 200 nt, including from about 50 to about 175 nt, e.g. 150 nt in length.

The term "polynucleotide" as used herein refers to single- or double-stranded polymers composed of nucleotide monomers of generally greater than about 100 nucleotides in length.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

"Hybridizing" and "binding", with respect to polynucleotides, are used interchangeably.

The term "stringent assay conditions" as used herein refers to conditions that are compatible to produce binding pairs of nucleic acids of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions (e.g., when hybridization is between solution phase and surface bound nucleic acids).

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

DETAILED DESCRIPTION

Methods and compositions for performing low background multiplex nucleic acid amplification reactions are provided. Aspects of the invention include contacting a nucleic acid sample with two or more primer pairs specific for two or more target nucleic acid sequences under template-dependent primer extension reaction conditions, e.g., polymerase chain reaction (PCR) conditions. The resultant amplified composition is then contacted with target nucleic acid circularizing reagents, and product circularized target nucleic acids are then selected, e.g., specifically amplified or enriched. Also provided are systems and kits that find use in practicing embodiments of the inventions.

As noted in the background section, conventional multiplex PCR reactions often generate significant amounts of non-target amplicons which most often are generated by mis-priming events (i.e., primers hybridizing to non-target nucleic acid sequences in the sample). Non-target amplicons are often referred to in the art as "background" products. The present invention provides methods and compositions for multiplex nucleic acid amplification that produce low to no non-target amplicons, and as such may be referred to as low background multiplex nucleic acid amplification reactions. In certain embodiments, a low background multiplex nucleic acid amplification reaction of the invention produces non-target amplicons in an amount of about 50% or less by weight of the target amplicons produced in the reaction, such as about 25% or less, about 15% or less, about 10% or less, and including about 5% or less by weight of the target amplicons produced in the reaction.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include, plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

Any recited method can be carried out in the order of events recited or in any other order which is logically possible.

In further describing various aspects of the invention, embodiments of methods that may be performed in accordance with the invention are reviewed first in greater detail, followed by a review of various applications in which the methods may find use, as well as a review of systems and kits that may find use in practicing methods of the invention.

Methods

As summarized above, aspects of the invention include methods of performing low background multiplex nucleic acid amplification reactions. By low background is meant a multiplex nucleic acid amplification reaction that produces low to no non-target amplicons. In certain embodiments, a low background multiplex nucleic acid amplification reaction of the invention produces non-target amplicons at about 50% or less by weight of the target amplicons produced in the reaction, such as about 25% or less, about 15% or less, about 10% or less, and including about 5% or less by weight of the target amplicons produced in the reaction, e.g., as determined using gel electrophoresis, such as described in the experimental section below. In certain embodiments, no non-target amplicons are produced in the low background multiplex amplification reactions of the present invention.

By multiplex nucleic acid amplification reaction is meant that more than one primer pair specific for a distinct target nucleic acid sequence is included in the reaction. In certain embodiments, the number of target-specific primer pairs in a multiplex amplification reaction is 2 or more, e.g., about 5 or more, about 10 or more, about 25 or more, about 50 or more, about 100 or more, about 500 or more, about 1000 or more and including up to about 2000 or more target-specific primer pairs. In such multiplex amplification reactions, each target specific primer pair is designed to produce a specific target amplicon that contains its cognate target nucleic acid sequence. As such, a multiplex amplification reaction produces 2 or more species of target amplicon, e.g., about 5 or more, about 10 or more, about 25 or more, about 50 or more, about 100 or more; about 500 or more, about 1000 or more, and up to about 2000 or more species of target amplicon.

In certain embodiments, one or more primer pair in a multiplex amplification reaction is a control primer pair, i.e., a negative or positive control primer pair. By negative control primer pair is meant that the primer pair should not produce a target amplicon in the multiplex amplification reaction (i.e., the nucleic acid sample used in the multiplex amplification reaction does not contain a target nucleic acid sequence for which the negative control primer pair is specific). By positive control primer pair is meant that the primer pair should produce a target amplicon in the multiplex amplification reaction (i.e., the nucleic acid sample used in the multiplex amplification reaction is known to contain a target nucleic acid sequence for which the positive control primer pair is specific).

Embodiments practiced in accordance with the invention may include the following steps:

multiplex amplification of two or more target nucleic acids of a nucleic acid sample;

specific circularization of the target amplicons in the produced amplified nucleic acid sample; and selection of the circularized target nucleic acids.

The resultant selected circularized target nucleic acids can be analyzed directly or further manipulated, e.g., subjected to further amplification, as desired.

Multiplex Amplification

As indicated above, the low background nucleic acid amplification reaction of the present invention includes a multiplex amplification step. Multiplex amplification reactions that find use in this step include, but are not limited to, strand displacement amplification (SDA), nucleic acid sequence based amplification (NASBA), or polymerase chain reaction (PCR; described in more detail below).

In certain embodiments, the multiplex nucleic acid amplification reaction employed is PCR. In standard PCR reactions known in the art, two primers, often referred to as a forward primer and a reverse primer, work in pairs to generate multiple copies of a specific target nucleic acid sequence present in a nucleic acid sample. In such standard PCR assays, the forward and reverse primers are designed to prime nucleic acid synthesis toward each other on opposite strands of the desired target sequence. By performing repeated cycles of melting, priming; and extending (i.e., nucleic acid synthesis), multiple specific target amplicons are formed. In such standard PCR reactions, the target amplicons formed are double stranded target nucleic acids bounded by the forward and reverse primer sequences.

There are a number of distinct types of PCR reactions that find use in the subject invention, and as such, no limitation in this regard is intended. Examples include reverse-transcription PCR (RT-PCR), inverse PCR, asymmetric PCR, etc., each of which are known in the art. Any convenient nucleotide polymerase or combination of polymerases may be used in the methods of the present invention, including but not limited to reverse transcriptases (e.g., Moloney Murine Leukemia Virus RT) and thermostable DNA polymerases (e.g., Taq, Pfu, Vent, etc.).

The nucleic acid sample employed in the nucleic acid amplification reaction of the subject invention contains a nucleic acid having a sequence for which at least one primer pair is specific. As such, the nucleic acid sample can be any of a wide variety types, including, but not limited to, genomic DNA, cDNA, total RNA, mRNA, siRNA, micro-RNA, plasmid DNA, viral DNA, viral RNA, etc. In certain embodiments, the nucleic acid sample is derived from whole organisms or from specific cells from an organism, e.g., cells from a specific tissue or cell line. In certain embodiments, the nucleic acid sample is derived from cells known to or suspected of having a disease condition and/or genetic abnormality. In certain embodiments, the nucleic acid sample is derived from an infectious agent or a tissue or organism known to or suspected of being infected by an infectious agent. In certain embodiments, the nucleic acid sample is enriched for certain nucleic acid species prior to the amplification reaction, e.g., by size fractionation, subtraction methods, ligand binding properties, nucleic acid type (e.g., DNA versus RNA) or any other convenient nucleic acid enrichment method.

While primer pairs for use in nucleic acid amplification reactions are designed to produce only target amplicons, non-target amplicons can also be produced. In general, a non-target amplicon is a population of amplified nucleic acids that vary in any way from the desired target amplicon. Non-target amplicons are generally considered amplified nucleic acid products that are the result of one or more of the primers in a nucleic acid amplification reaction annealing to non-target sites in the nucleic acid in the sample. Examples of non-target amplicons include, but are not limited to, non-target sequences bounded by the same primer (e.g., two forward or two reverse primers) and non-target sequences bounded by the forward and reverse primers. In multiplex amplification embodiments, the potential for non-target amplicons increases dramatically with increasing numbers of primer pairs, as the potential for mis-priming events generating amplifiable non-target amplicons is greatly increased. In these embodiments, non-target amplicons also include those having non-target sequences bound by any combination of primers in the sample.

FIG. 1 provides a schematic of a multiplex amplification reaction employing three primer pairs and potential amplicons, both target and non-target, that can be produced. Nucleic acid 100 contains target sequences for which three distinct primer pairs are specific. The first primer pair contains forward primer 101 and reverse primer 102, the second primer pair contains forward primer 103 and reverse primer 104, and the third primer pair contains forward primer 105 and reverse primer 106. Upon performing the multiplex'amplification reaction, the expected target amplicons are produced as well as a number of non-target amplicons.

Specifically, as shown in FIG. 1, the target amplicons will have the unique characteristic of having the target nucleic acid sequence bounded by the two cognate primers (i.e., forward and reverse primers from a specific pair). In contrast, the non-target amplicons will not have this configuration. For example, non-target amplicon 107 contains a nucleic acid sequence bounded by the forward primer of the first primer pair (101) and the reverse primer of the second primer pair (104). Any configuration that does not conform to the description of the target amplicon is considered a non-target amplicon. Only a few representative non-target amplicons are shown in FIG. 1.

Circularization of Target Amplicons

As noted above, the methods of the subject invention include selective circularization of only target amplicons produced in the multiplex amplification reaction. In certain embodiments, circularization involves 1) hybridizing target amplicons produced in the multiplex amplification reaction to cognate circularization template oligonucleotides (sometimes referred to as Collector probes; e.g., as in Example 4 below) to form circularization complexes; and 2) ligating the ends of the hybridized target amplicons together (i.e., intramolecularly) by contacting the circularization complex to a ligating agent (or agents). In these embodiments, each circularization template oligonucleotide is designed to form circularization complexes with a specific target amplicon generated in the multiplex amplification reaction but not with non-target amplicons (described in detail below). Thus, the circularization template oligonucleotides of the invention facilitate circularization of target amplicons but not non-target amplicons.

In certain embodiments, free primers are removed from the multiplex-amplified nucleic acid sample prior to the hybridization step. By "free primer" is meant any primer that has not served as a primer for a nucleic acid synthesis reaction in the multiplex nucleic acid amplification reaction. Any convenient primer removal method may be employed. For example, the multiplex-amplified nucleic acid sample may be passed over a size selection column that retains short primer oligonucleotides but allows larger nucleic acids (e.g., amplicons) to pass through. Alternatively, the amplified nucleic acid sample can be contacted with an exonuclease that specifically degrades single stranded DNA (e.g., *E. coli* exonuclease I). As another example, the amplified nucleic acid sample may be subjected to a precipitation reaction in which smaller nucleic acids remain in the supernatant whereas the larger nucleic acids are in the pellet.

Any convenient hybridization method can be used in hybridizing the target amplicons to the circularization template oligonucleotide. In certain embodiments, the multiplex-amplified nucleic acid sample and the specific circularization template oligonucleotides are combined and incubated under conditions that promote specific hybridization between target amplicons and their cognate circularization template oligonucleotides, e.g., stringent hybridization conditions. In certain embodiments, the target amplicons are denatured prior to placing the sample under stringent hybridization conditions to promote strand separation of the double stranded amplicons, which allows the circularization template oligonucleotide to anneal to complementary sequences present at the ends of the cognate target amplicons (similar to the annealing in standard PCR reactions). Denaturation (or strand separation) may be carried out by any convenient method.

In certain embodiments, one strand of the double-stranded target amplicons is enriched prior to contact with the cognate circularization template oligonucleotides. In these embodiments, the target amplicon strands enriched are the ones that are predicted to hybridize to their cognate circularization template oligonucleotide to form the circularization complex (described in more detail below). Any convenient method for enriching for single-stranded target amplicons may be employed. For example, single stranded target amplicons may be selected by biotinylating one of the primers of each primer pair used in the multiplex nucleic acid amplification reaction. The resultant double stranded target amplicons will thus have one biotinylated and one non-biotinylated strand. The non-biotinylated strands can then be enriched by denaturing the multiplex-amplified nucleic acid sample, binding the denatured sample to a streptavidin-conjugated solid support, and eluting the unbound fraction (e.g., using sodium hydroxide).

As indicated above, circularization template oligonucleotides of the invention are designed to promote intramolecular ligation of target amplicons that results in circular target amplicon products. The circularization template oligonucleotides accomplish this by serving as a template that brings the distal ends of one strand of a target amplicon into proximity such that a ligating agent (or agents) can act on the target amplicon and form a circular product (i.e, a circularized target amplicon). In certain embodiments, a circularization template oligonucleotide of the invention contains a first domain and a second domain, where the first domain contains a nucleic acid sequence that is complementary to a sequence at or near the first end of one strand of a target amplicon and the second domain contains a nucleic acid sequence that is complementary to a sequence at or near the second end of the same strand of the target amplicon. In certain embodiments, the nucleic acid sequence of the first domain and the second domain contains is about 5 or more nucleotides in length, including about 10 or more nucleotides, about 15 or more nucleotides, about 20 or more nucleotides, about 30 or more nucleotides, about 50 or more nucleotides, and including up to about 100 or more nucleotides. In certain embodiments, the first and second domains of the circularization template oligonucleotide are of similar size, whereas in other embodiments the first and second domains are different sizes. The sequences at or near the end of the target amplicon to which the first and second domain of the circularization template oligonucleotide are designed to hybridize can include primer sequences (e.g., forward primer sequence or its complement and reverse primer sequences or its complement), sequences adjacent to the primer sequences, or combinations thereof. The length of the circularization template oligonucleotide may vary widely and may depend on the specifics of the target amplicon and the desired circularized product thereof. In certain embodiments, circularization template oligonucleotides contain an intervening domain that is between the first and second domains. In certain embodiments, intervening domain contains a nucleic acid sequence that is not designed to hybridize to sequences in the target amplicon (e.g., universal amplification sequences, described below). In certain embodiments, the intervening domain can be a single nucleotide or more in length, including up to about 5 nucleotides or more in length, such as from about 10 nucleotides or more, about 15 nucleotides or more, about 20 nucleotides or more, about 30 nucleotides or more, about 50 nucleotides or more, about 100 nucleotides or more, and including up to about 200 nucleotides or more in length. As such, in certain embodiments, the circularization template oligonucleotide is up to about 10 nucleotides or more in length, such as about 20 nucleotides or more, about 30 nucleotides or more, about 50 nucleotides or more, about 100 nucleotides or more, about 200 nucleotides or more, about 400 nucleotides or more and including up to about 400 nucleotides or more in length.

Figure 2:
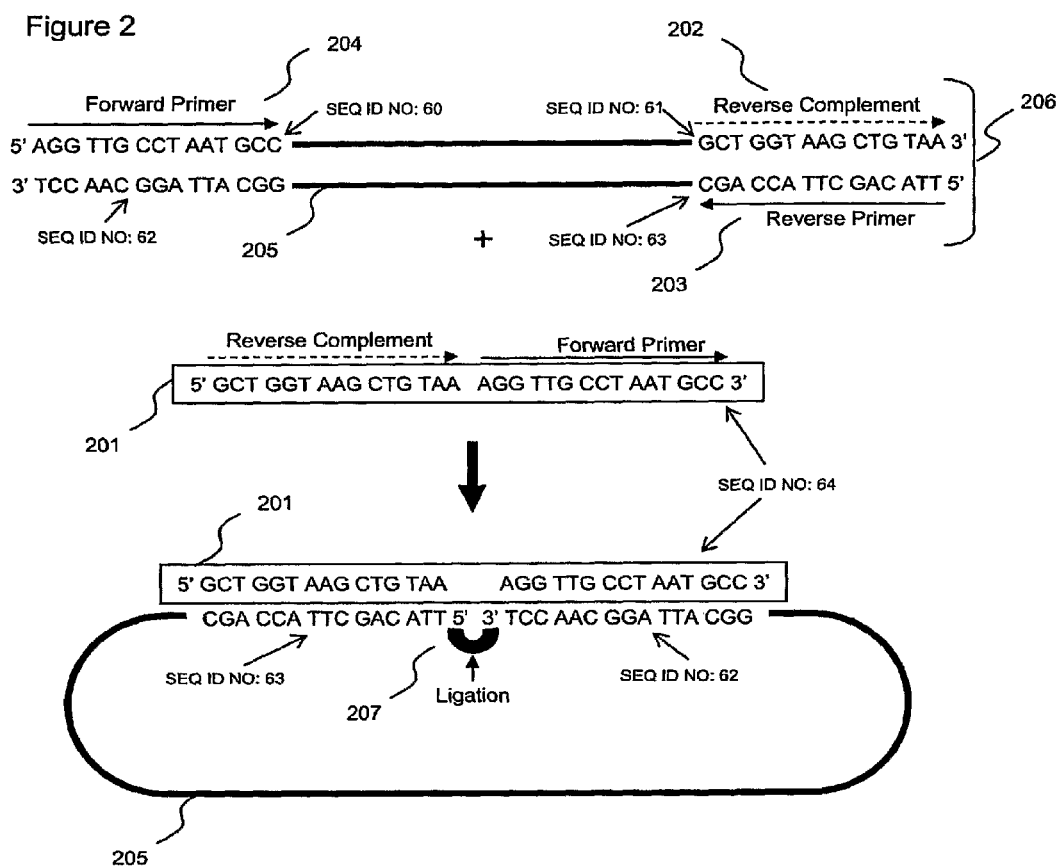
FIG. 2 illustrates an exemplary target amplicon and circularization template oligonucleotide.

FIG. 2 provides one example of sequences for the primer regions of a target amplicon and a circularization template oligonucleotide specific for the target amplicon. In FIG. 2, target amplicon 206 was amplified using forward primer 204 and reverse primer 203. Circularization template oligonucleotide 201 contains, in the 5' to 3' direction, the complementary sequence 202 of reverse primer 203 followed by the sequence of the forward primer 204. In this orientation, the circularization template oligonucleotide 201 will hybridize to the lower strand 205 of target amplicon 206 and brings the ends into close proximity to form a circularization complex, which allows them to be ligated by a ligating agent 207 (described in further detail below).

Figure 3:
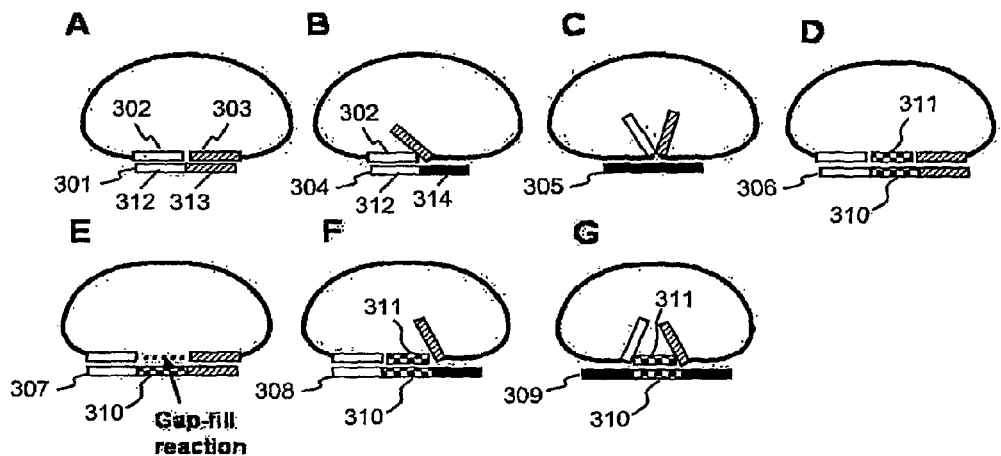
FIG. 3A-3G each illustrate a distinct circularization complex that is formed using a specific circularization template oligonucleotide.

Circularization template oligonucleotides that find use in the present invention can have a wide variety of configurations and as such, can form a variety of distinct types of circularization complexes. Certain embodiments of such circularization template oligonucleotides hybridized to single-stranded target amplicons (i.e., circularization targets) to form circularization complexes are shown in FIG. 3. FIG. 3A illustrates circularization template oligonucleotides similar to that shown in FIG. 2. In these embodiments, the circularization template oligonucleotide 301 contains a first domain 312 and a second domain 313 containing sequences that hybridize to the primer regions 302 and 303, respectively, of a single stranded target amplicon. In FIG. 3B, the circularization template oligonucleotide 304 contains a first domain 312 that is complementary to one of the primer regions 302 in the target amplicon and a second domain 314 that is complementary to an internal sequence of the target amplicon. As can be seen from FIG. 3B, in certain embodiments, hybridization of a target amplicon to a circularization template oligonucleotide results in one matched end and one end having an overhang sequence. Removal of the overhang sequence [e.g., "flap"-based cleavage as described in Dahl et al Nucleic Acids Res. 2005 Apr. 28; 33(8):e71] results in juxtaposed 3' and 5' ends on the target amplicon that are suitable for ligation. As such, an internal site can be used for selective circularization. This internal ligation site can be within the primer binding region of the target amplicon or internal to the primer binding regions (as shown in FIG. 3B). In FIG. 3C, circularization template oligonucleotide 305 contains first and second domains that are complementary to internal sequences of the target amplicon. As with the example in FIG. 3B, removal of the overhang sequences on both ends will result in juxtaposed 5' and 3' ends suitable for ligation.

In each of FIGS. 3D-G, the circularization template oligonucleotide (306, 307, 308 and 309, respectively) contains an intervening domain 310 that is between the regions that hybridize to the target amplicon (described above). The intervening domain of the circularization template oligonucleotide can have virtually any nucleic acid sequence provided that it does not interfere with circularization of the target nucleic acid for which it was designed. In certain embodiments, the intervening domain is included to serve a particular function in either the selection process or in downstream applications. For example, specially designed intervening domains can be used as primer binding sites for subsequent nucleic acid amplification of the target amplicon. In FIG. 3D, the circularization template oligonucleotide includes an intervening domain 310 that has a complementary oligonucleotide 311 hybridized thereto. Hybridization of this circularization template oligonucleotide and hybridized oligonucleotide to its cognate target amplicon forms a circularization complex that produces a circularized target amplicon having additional known sequences (i.e., the complement of the intervening domain). FIGS. 3F and 3G show circularization complexes that are analogous to those shown in FIGS. 3B and 3C, respectively, except that the circularization template oligonucleotides include intervening domain 310 hybridized to a complementary oligonucleotide 311. The circularization complex shown in FIG. 3E is similar to that shown in 3D except that the intervening domain 310 is not hybridized to a complementary oligonucleotide. In this example, formation of the circularized target amplicon is achieved by performing a nucleic acid synthesis reaction (a gap fill reaction) prior to closing the circle by ligation. Any convenient nucleic acid synthesis method for filling in the gap may be employed. In certain embodiments, the nucleic acid polymerases employed in such gap fill reactions lack exonuclease activity (e.g., 5' to 3' exonuclease activity). Non-limiting examples of such polymerases include the Klenow fragment of *E. coli* DNA polymerase and the large fragment of the thermostable *B. stearothermophilus* DNA polymerase.

As noted above, once circularization complexes are formed, the target amplicon is circularized by contacting the circularization complex to a ligating agent(s). Any convenient ligating agent may be used in the methods of the invention, where the choice of ligating agent is guided in part by the type of circularization complex formed. In certain embodiments, the ligating agent is a DNA ligase, e.g., T4 DNA ligase. Certain ligases require the presence of a 5' end phosphate group to achieve DNA ligation. Any convenient method for ensuring that the target amplicon is appropriately 5' phosphorylated may be employed. For example, one or both of the primers of a primer pair can be 5' phosphorylated prior to performing the nucleic acid amplification reaction. As another example, the target amplicon can be 5' phosphorylated by being contacted to a nucleotide kinase (e.g., T4 polynucleotide kinase) at any time in the assay after the amplification step and prior to the ligation step.

There are many possible variations in the target amplicon circularization methods described above. Non-limiting representative variations are described in brief below.

In certain embodiments, each primer of a cognate primer pair contains a compatible restriction enzyme recognition sequences that promote amplified target circularization when cleaved (prior to formation of the circularization complex). By compatible means that the cleaved sites have compatible cohesive ends that facilitate ligation.

In certain embodiments, one or more primers of a primer pair in a nucleic acid amplification reaction include additional non-target binding sequences that serve as all or part of the sequences that are complementary to the circularization template oligonucleotide. In certain of these embodiments, such additional non-target complementary sequences are present at the 5' end of the primer. In general, primers having these additional non-target binding sequences will be longer than primers that do not have these sequences. These non-target sequences in the primers may be so called molecular bar codes, frequently used in multiplex DNA detection on DNA microarrays (see, e.g., Hardenbol et al., Nature Biotechnology 2003, 21(6):673-8).

In certain embodiments, the circularization template oligonucleotide is modified to allow for its targeted degradation after the ligation step. Any convenient modification can be used. For example, the circularization template oligonucleotide can incorporate deoxyuridine residues (instead of deoxythymidine) which serve as targets for Uracil-N-Glycosylase digestion. Upon completion of the target amplicon ligation reaction, the sample can be treated with Uracil-N-Glycosylase which will selectively degrade the circularization template oligonucleotide.

In certain embodiments, one or more steps of the method are carried out on a solid support, e.g., a bead or array surface. In certain of these embodiments, the circularization template oligonucleotide is immobilized on a solid support. In such embodiments, the circularization complex is formed on the solid support (e.g., incubated with a sample having cognate target amplicons under hybridization conditions), contacted to a ligating agent, and then released form the solid support, e.g., under denaturing conditions. In certain embodiments, wash steps are be included. In certain other embodiments, the primers used in the nucleic acid amplification reaction are immobilized on a solid support. In certain embodiments, primer pairs are synthesized in multiplex on a DNA microarray, employed in a solid-support-based amplification reaction, and then the products are cleaved off for further use.

In certain embodiments, more than one circularization target oligonucleotide is provided for target amplicons generated by a primer pair. For example, Taq polymerase is known to sometimes add an additional "A" nucleotide to the 3' end of an amplified product (this is the reason TA cloning of Taq-amplified targets works). As such, two distinct target amplicons are generated when using Taq (i.e., with regard to the strand of interest which will bind to a circularization target): those that have an additional "A" and those that don't (the blunt end amplicon). To circularize both of these target amplicon species, two circularization oligonucleotides can be employed: one that will form a circularization complex with the additional "A" target amplicon and one that will form a circularization complex with the blunt end target amplicon.

When the nucleic acid amplification reaction is a multiplex amplification reaction, the target amplicons generated can be at varying concentrations in the amplified nucleic acid sample. This may be due to many factors, including, but not limited to, varying amounts of the targets in the original nucleic acid sample, differences in the efficiency of target amplification during the multiplex amplification reaction, or both. In certain embodiments, it is desirable to normalize such a pool of target amplicons to contain substantially the same or similar amounts of each before analysis [e.g., high throughput sequencing analysis [Margulies M. et al Nature 2005 Sep. 15; 437(7057):376-80)]. In certain of these embodiments, normalization can be accomplished by providing the same limiting amount of the circularization template oligonucleotides for each target amplicon. By limiting amount is meant that the molar ratio of the lowest frequency target amplicon in the amplified sample to the circularization template oligonucleotide is less than 1. Having a limiting amount of the circularization template oligonucleotides effectively normalizes the target amplicons because the surplus of each target amplicon will not be circularized and thus not selected for (as described below).

Selection of Circularized Target Amplicons

The circularization step described above results in a circularized sample which contains circularized target amplicons and non-circularized (i.e., linear) non-target amplicons. The linear non-target amplicons are generally referred to herein as "background constituents". In addition to the circularized target amplicons and background constituents, the circularization sample may also contain one or more of: non-circularized target amplicons, non-ligated circularization complexes, circularization template oligonucleotides, and oligonucleotides complementary to the intervening domain.

Figure 4:
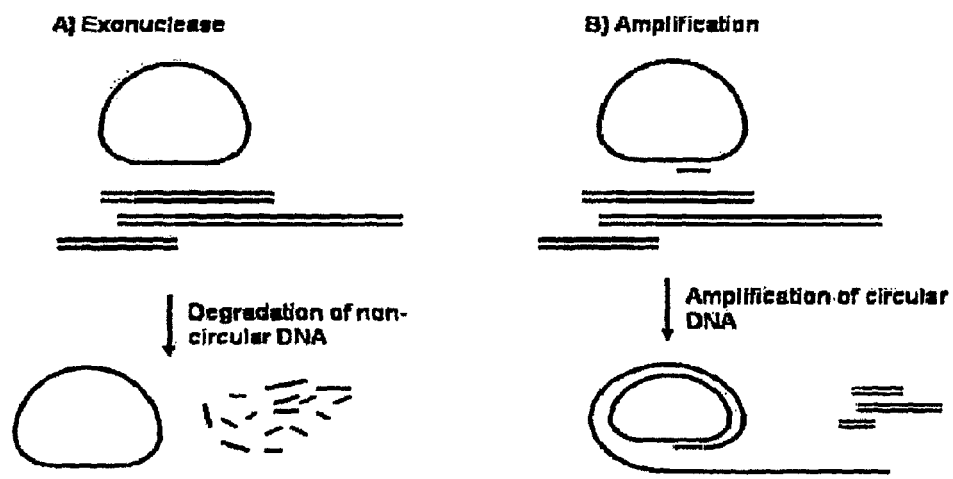
FIGS. 4A and 4B illustrate different DNA circle enrichment strategies.

To reduce the amount of background (and other) constituents in the circularized sample, the methods of the invention may include selection of the circularized target amplicons to produce a low-background amplification sample. Selection of circularized target amplicons can be carried out using any convenient method, and can include positive and/or negative selection methods. In certain embodiments, background constituents in the circularized sample are removed by contacting the circularization sample with an exonuclease that degrades linear, but not circularized, nucleic acids. One non-limiting example of such an exonuclease is E. coli exonuclease I. This embodiment is illustrated in FIG. 4A and is described, for example, in Hardenbol et al. (Nat Biotechnology, 2003, 21(6):673-8). In certain embodiments, after degradation of the linear nucleic acid constituents, the exonuclease is inactivated so that it does not interfere with subsequent analysis or assays performed on the sample (e.g., further amplification reactions).

In certain embodiments, circularization of target amplicon(s) is enhanced by modulating the relative concentration of the circularization template oligonucleotide and the amplicons in the amplified sample. For example, circularization of target amplicons can be enhanced is by using a low relative concentration of the circularization template oligonucleotide. In these embodiments, the intramolecular effects of two matched hybridization events make matched circularization favored over hybridization/ligation to non-target amplicons.

In certain embodiments, the circularized sample is subjected to another round of nucleic acid amplification that selectively amplifies the circularized target amplicons contained therein. For example, circularized target amplicons can be amplified by rolling circle replication as shown in FIG. 4B and described, for example, in Baner J. et al (Nucleic Acid Res. 1998 Nov. 15; 26(22):5073-8). The primer binding site for rolling circle amplification can be virtually anywhere in the circularized target, including in amplification primer regions, intervening domain regions, and target regions between the primer regions. In certain embodiments, hyperbranched rolling-circle replication is employed (e.g., as described in Zhang et al., Mol Diagn. 2001, 6(2):141-50). Commercial kits for performing rolling circle amplification are available (e.g., TempliPhi, GE Healthcare; method described in Dean et al., Genome Res. 2001, 11: 1095-1099). As another example, circularized targets can be amplified by PCR. In embodiments in which an intervening domain is present in the circularization template oligonucleotide, cognate primer pairs that bind in this region can be employed to re-amplify circularized target amplicons (see FIG. 5, described in more detail below). In certain embodiments, each cognate circularization template oligonucleotide used to circularize target amplicons in a multiplex amplification reaction contains an intervening domain containing an identical nucleic acid region such that a single primer pair can be employed to amplify all circularized target amplicons. In certain embodiments, the nucleic acid amplification reaction is performed after exonuclease digestion of the linear nucleic acids in the circularized sample (as described above). One non-limiting example is described in Dahl et al (Nucleic Acids Res. 2005 Apr. 28; 33(8):e71).

In certain embodiments, the circularized target amplicons are linearized prior to amplification. Linearization can be achieved using any convenient method. In certain embodiments, the circularized target amplicon is contacted to a restriction endonuclease that cleaves the amplicon at a unique site that was engineered into one of the primers or into the intervening domain of the circularization template oligonucleotide. In other embodiments, a deoxy-Uridine residue included in one of the primers or the circularization template oligonucleotide can be used for linearizing the circularized target amplicon with Uracil-N-Glycosylase. In embodiments in which the sample is contacted to exonuclease prior to amplification, the exonuclease is removed and/or inactivated prior to any linearization step (e.g., by heat inactivation). The linearized target amplicon may be used for further downstream applications or analyzed as desired. For example, the linearized amplicon can have linkers ligated to the ends for further amplification, sequencing, purification, etc.

Figure 5:
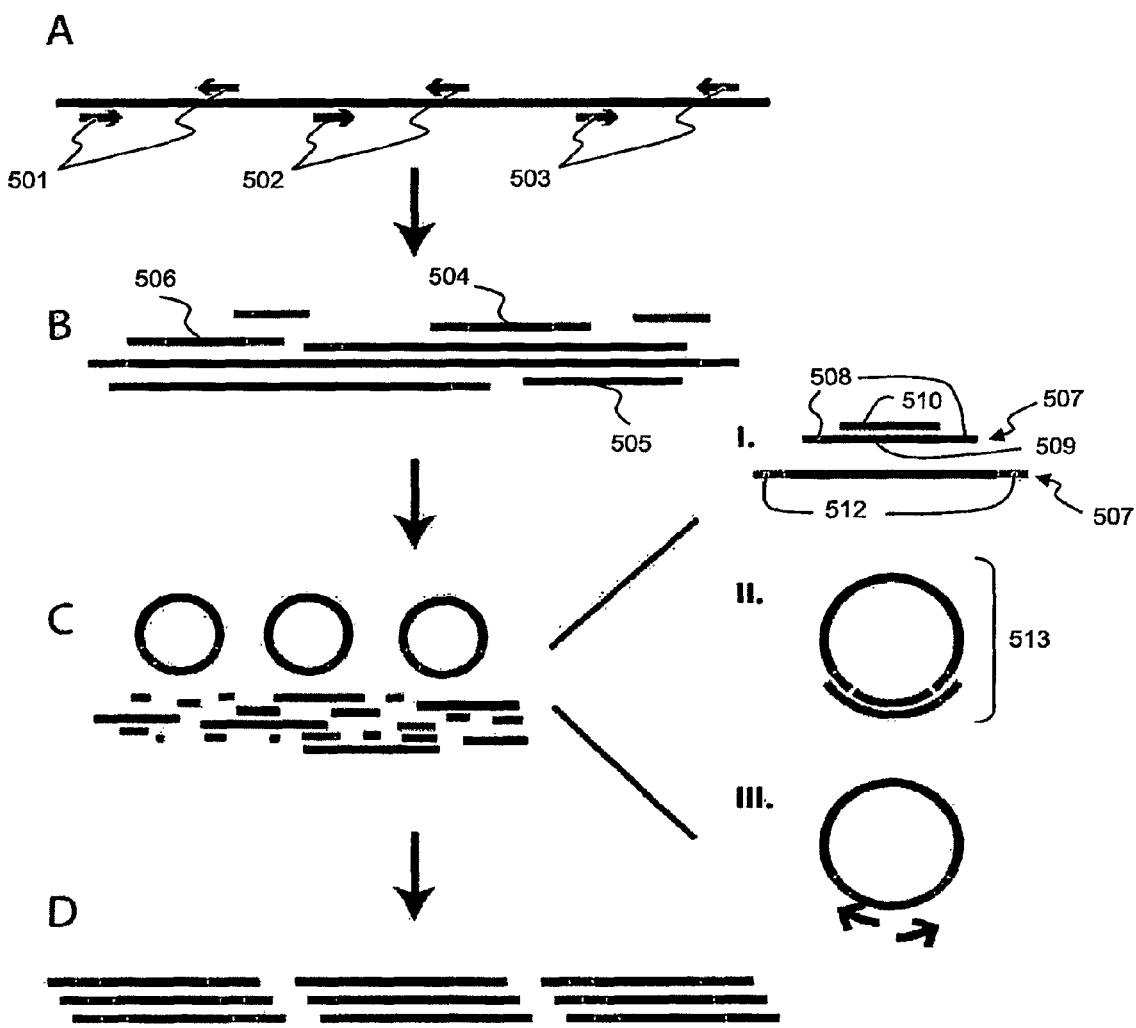
FIG. 5A to 5D together illustrate an exemplary target amplicon circularization and selection method according to one embodiment of the present invention.

FIG. 5 provides an exemplary diagram of one embodiment of the present invention. In this figure, a multiplex amplification reaction is carried out using three target specific primer pairs (panel A; 501, 502, and 503), generating both target amplicons (panel B; 504, 505, and 506) and non-target amplicons (panel B; not numbered). Targets amplicons that contain matched primer pairs are circularized (panel C), leaving non-target amplicons linear and therefore substrates for exonuclease. The circularization template oligonucleotide, circularization complex and resultant circularized target amplicon are shown on the right of panel C. (I) Circularization template oligonucleotide 507 has sequences 508 complementary to the ends 512 of target amplicon 511 as well as intervening domain 509 which is hybridized to its complement 510. In this example, each of the three circularization template oligonucleotides contains the same intervening domain and hybridized complement. (II) When hybridized, the target amplicon and circularization template oligonucleotide form a circularization complex 513. Circularization of the target amplicon results in a circularized target product that includes the complement of the intervening domain; (III) Once ligated, a universal amplification reaction is carried out using a primer pair that primes in the intervening domain region. In certain embodiments, the amplification is performed after removal of non-circularized species (e.g., by exonuclease digestion). This second amplification generates a final amplification sample that has low background (i.e., contains primarily target amplicons as defined above). In this example, all of the resulting target amplicons are flanked by intervening domain sequences (panel D).

Systems

The present invention provides systems for performing low background multiplex nucleic acid amplification reactions as described above. In certain embodiments, a system of the invention includes the following components: two or more target-specific primer pairs; a circularization template oligonucleotide specific for the predicted target amplicon for each primer pair; and ligating reagents. In certain embodiments, the system includes reagents for performing a multiplex amplification reaction including, but not limited to, one or more of: nucleotide triphosphates, reaction buffers, and one or more nucleic acid polymerase (e.g., thermostable DNA polymerase, reverse transcriptase, etc.). In certain embodiments, the system includes reagents for removing free primers form a multiplex amplification reaction (e.g., spin columns, nucleic acid precipitation reagents). In certain embodiments, one or more of the primers of the target-specific primer pairs in the system is modified (e.g., 5' phosphorylated, biotinylated, etc.). Such modifications will depend on the particular method of the invention for which the system is designed.

In certain embodiments, the system includes up to 5 or more target-specific primer pairs, including, e.g., about 10 or more, about 25 or more, about 50 or more, about 100 or more, about 500 or more, about 1000 or more and including up to about 2000 or more target-specific primer pairs. In certain embodiments, ligating reagents of the system include one or more of: DNA ligase, reagents for gap fill reaction (e.g., DNA polymerase, nucleotide triphosphates, etc.), reagents for 5' phosphorylation reaction (e.g., T4 polynucleotide kinase), and reagents, for "flap"-based cleavage reaction. In certain embodiments, the system includes reagents for removing linear nucleic acids from a circularized sample, e.g., E. coli exonuclease I and buffers for use. In certain embodiments, the system includes reagents for performing an amplification reaction on the circularized sample. Such reagents include, but are not limited to, one or more of: universal primer pair, rolling circle primer, nucleotide triphosphates, reaction buffers, and one or more nucleic acid polymerase (e.g., thermostable DNA polymerase, Klenow, etc.).

Kits

The present invention provides kits that find use in performing low background multiplex nucleic acid amplification reactions as described above. In certain embodiments, a kit of the invention contains the following components: two or more primer pairs specific for distinct target nucleic acid sequences; and a circularization template oligonucleotide specific for the predicted target amplicon for each target-specific primer pair. In certain embodiments, the kit contains circularizing agent(s) (e.g., DNA ligase). In certain embodiments, the kit contains reagents for performing a multiplex amplification reaction including, but not limited to, one or more of: nucleotide triphosphates, reaction buffers, and one or more nucleic acid polymerase (e.g., thermostable DNA polymerase, reverse transcriptase, etc.). In certain embodiments, the kit contains positive and negative control nucleic acid samples for use as templates in the multiplex amplification reaction. In certain embodiments, the kit contains control primers (positive and/or negative). In certain embodiments, the kit contains reagents for removing free primers form a multiplex amplification reaction (e.g., spin columns, nucleic acid precipitation reagents, etc.). In certain embodiments, one or more of the primers of the target-specific primer pairs in the kit is modified (e.g., 5' phosphorylated, biotinylated, etc.). Such modifications will depend on the particular method of the invention for which the kit is designed to perform.

In certain embodiments, the kit contains up to 5 or more target-specific primer pairs, including, e.g., about 10 or more, about 25 or more, about 50 or more, about 100 or more, about 500 or more, about 1000 or more and including up to about 2000 or more target-specific primer pairs. In certain embodiments, circularizing agent(s) of the kit contain one or more of: DNA ligase, reagents for gap fill reaction (e.g., DNA polymerase, nucleotide triphosphates, etc.), reagents for 5' phosphorylation reaction (e.g., T4 polynucleotide kinase), and reagents for "flap"-based cleavage reaction. In certain embodiments, the kit contains reagents for removing linear nucleic acids from a circularized sample, e.g., E. coli exonuclease I and buffers for use. In certain embodiments, the kit contains reagents for performing an amplification reaction on the circularized sample. Such reagents include, but are not limited to, one or more of: universal primer pair, rolling circle primer, nucleotide triphosphates, reaction buffers, and one or more nucleic acid polymerase (e.g., thermostable DNA polymerase, Klenow, etc.).

In certain embodiments, the kits contain instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Utility

As is evident form the description of the subject invention above, the low background multiplex amplification compositions and methods described herein find use in a wide range of protocols, e.g., assays that employ amplification of nucleic acids. While certain specific examples are discussed below, no limitation in this regard is intended.

In certain embodiments, target amplicons in a low background amplification reaction as described herein are analyzed directly using any convenient method. Exemplary assays include, but are not limited to, gel electrophoresis, mass spectrometry, nucleic acid hybridization assays (e.g., southern blot analysis, microarray analysis, etc.), restriction enzyme digestion analysis, nucleic acid quantitation assays, single strand nucleic acid polymorphism analysis, etc.

In certain embodiments, target amplicons are employed in assays that include additional manipulation. In certain of these embodiments, one or more of the selected target amplicons is sub-cloned into a vector prior to use in downstream assays (e.g., plasmid vector, viral vector, sequencing vector, expression vector, library vector, combinations thereof, etc.). Sub-cloning can be achieved using any convenient method, and may include contacting the target amplicons to agents that facilitate the sub-cloning reaction (e.g., restriction enzymes, polynucleotide kinases, phosphatases, ligases etc.). In certain embodiments, the target amplicons in a multiplex reaction are fractionated (e.g., separated from each other) prior to use in a downstream assay. Non-limiting fractionation methods include fractionation by size (e.g., gel electrophoresis, size selection column, etc.), by affinity (e.g., to a nucleic acid binding protein, complementary nucleic acid sequence, etc.), by molecular conformation, etc. In certain embodiments, target amplicons generated in the low background amplification reaction of the invention are used in a PCR reaction. In certain of these embodiments, the PCR reaction is a real-time PCR reaction (e.g., as shown in the examples section below). Such PCR reactions may be employed to determine which (if any) of the target primer pairs used in a multiplex amplification reaction produced a product (i.e., the nucleic acid sample contained a target nucleic acid for which the primer pair is specific).

In certain embodiments, one or more of the target amplicons in a low background amplification reaction of the'present invention are subjected to nucleic acid sequence analysis. As indicated above, certain sequencing embodiments include a target amplicon fractionation and/or sub-cloning step prior to performing the sequencing reaction. For example, Sanger type sequencing can be performed using one or both of the initial multiplex amplification primers as a sequencing primer(s). In addition, pyro-sequencing or other sequencing by synthesis is also applicable. Regardless of the sequencing system used, having a low background amplified sample produced according to the present invention as a starting material (as opposed to higher background amplified samples) enhances their efficiency and accuracy. In certain embodiments, the sequencing assay employed is a highly parallel DNA analysis platform. For example, this process can be used in conjunction with large-scale sequencing and re-sequencing platforms [e.g., as reviewed in Shendure, J., et al., Nat Rev Genet, 2004. 5(5): p. 335-44]. Representative examples include sequencing by hybridization [e.g., Chee, M., et al., Science, 1996. 274(5287): p. 610-4; and Patil, N., et al., Science, 2001. 294(5547): p. 1719-23.], sequencing by ligation [Shendure, J., et al., Science, 2005: p. 1117389.], and sequencing by synthesis [e.g., Margulies, M., et al., Nature, 2005; Brenner, S., et al., Nat Biotechnol, 2000. 18(6): p. 630-4; and Mitra, R. D., et al., Anal Biochem, 2003. 320(1): p. 55-65] systems.

The low background amplification compositions and methods of the present invention can also be used in any of a variety of genotyping and diagnostic methods [e.g., see Syvanen, A. C., Nat Genet, 2005. 37 Suppl: p. S5-10; and Syvanen, A. C., Nat Rev Genet, 2001. 2(12): p. 930-42]. The functionality of genotyping and diagnostic methods that analyze amplified target nucleic acids, especially in multiplex format, are significantly hampered by background non-target amplicons present in the sample. As such, employing low-background samples amplified in accordance with the present invention can improve the accuracy and efficiency of these types of assays. In addition, the present invention can reduce the amount of the original nucleic acid sample required for analyzing multiple distinct target nucleic acids by allowing the use of increased numbers of distinct primer pairs in a single multiplex reaction without leading to the generation of significant levels of non-target (background) amplicons. Genotyping and diagnostic assays in which the low background amplification methods and compositions of the invention find use include, but are not limited to, mini-sequencing [e.g., Syvanen, A. C., et al., Genomics, 1990. 8(4): p. 684-92; and Pastinen, T., et al., Genome Res, 2000. 10(7): p. 1031-42], primer extension-based methods in concert with mass spectrometry analysis [e.g., Tost, J. and I. G. Gut, Mass Spectrom Rev, 2002. 21(6): p. 388-418], and pathogen detection, including high throughput pathogen detection (e.g., detection of the presence of multiple pathogen-derived nucleic acids in multiple samples). Furthermore, the multiplex amplification reactions of the present invention can increase throughput of mutation detection techniques that typically use many single amplification reactions by enabling multiplexing of the various primer pairs without leading to the production of interfering levels of background amplicons [see, e.g., the assays described in Faham, M., et al., Hum Mol Genet, 2001. 10(16): p. 1657-64; and Fakhrai-Rad, H., et al., Genome Res, 2004. 14(7): p. 1404-12].

While the methods and compositions of the invention described above are drawn primarily to multiplex amplification, the subject invention also finds use in low background amplification reactions in which a single target nucleic acid sequence of interest is amplified (e.g., a single primer pair is employed in a PCR reaction).

EXPERIMENTAL

Example 1

Non-Target Amplicons Formed with Multiplex PCR

To illustrate the amplification artifacts produced during a traditional multiplex PCR amplification of many selected fragments, 12 PCR primer pairs specific for exons of the EGFR gene were combined in one reaction (see Table 1 for primer pair sequences). PCR was performed in 50 μL, 50 nM of each primer, 5 Units of Pfu polymerase, 1×Pfu buffer (Stratagene), 25 mM dNTP's and 0.5 μg of human genomic DNA. Temperature cycling: 1) 95° C. 5 min; 2) 40 cycles of: 95° C., 30 sec; 55° C., 30 sec; 72° C., 60 sec; 3) 72° C. 10 min.

TABLE 1

EGFR primer pair sequences (5' to 3') for first amplification reaction.

| Primer Pair # | Forward | SEQ ID NO: | Reverse [5' Phosphorylated] | SEQ ID NO: |
|---|---|---|---|---|
| 1 | ATC CTG CAT GGG ATG GTG | 1 | AAA CAG GAA AGG ACG GGC | 2 |
| 2 | ACC TGG ACC TTG AGG GAT TG | 3 | CTT CAA GTG GAA TTC TGC CC | 4 |
| 3 | CCC TGG ACC CAT TTT AGA CC | 5 | CCA TCG GAA CTG CTG TCT G | 6 |
| 4 | AGC ACA TGC ATC CTT CAT GG | 7 | AGT GCT GTA GAG CTG TCC CC | 8 |
| 5 | GAA AGG GCG TCA TCA GTT TC | 9 | CAA GTG AAG GAA GAG AGG GG | 10 |
| 6 | CCC TGG GAA ATG ATC CTA CC | 11 | GTC TTC TGT CCT GGT GTG GG | 12 |
| 7 | CGC TTC CTC CGT GTG TG | 13 | AGG AGA CAG AGC GGG ACA AG | 14 |
| 8 | CTC AAG AGG ACC TGG ACC G | 15 | GAG CCC AGC CTC AGC AG | 16 |
| 9-10 | GGA TCC CTA GCT ATT CTT AAT CCA AC | 17 | GGA AAT ATG TCG AAA AGT TCT CTC TC | 18 |
| 11 | CAG AGT CCC TGA GAG TCT AGA GTA ATG | 19 | GAG CTC TGT GCC CTA TCT TAG C | 20 |

TABLE 1-continued

EGFR primer pair sequences (5' to 3') for first amplification reaction.

| Primer Pair # | Forward | SEQ ID NO: | Reverse [5' Phosphorylated] | SEQ ID NO: |
|---|---|---|---|---|
| 12 | CTC CCA CAG CAT GAC CTA CC | 21 | GGA ATT CAC ATG GTA ATT TCA CAG | 22 |
| 13 | AAG GTG CCG TCT CCT CC | 23 | GCT ATA ACA ACA ACC TGG AGC C | 24 |

Figure 6:
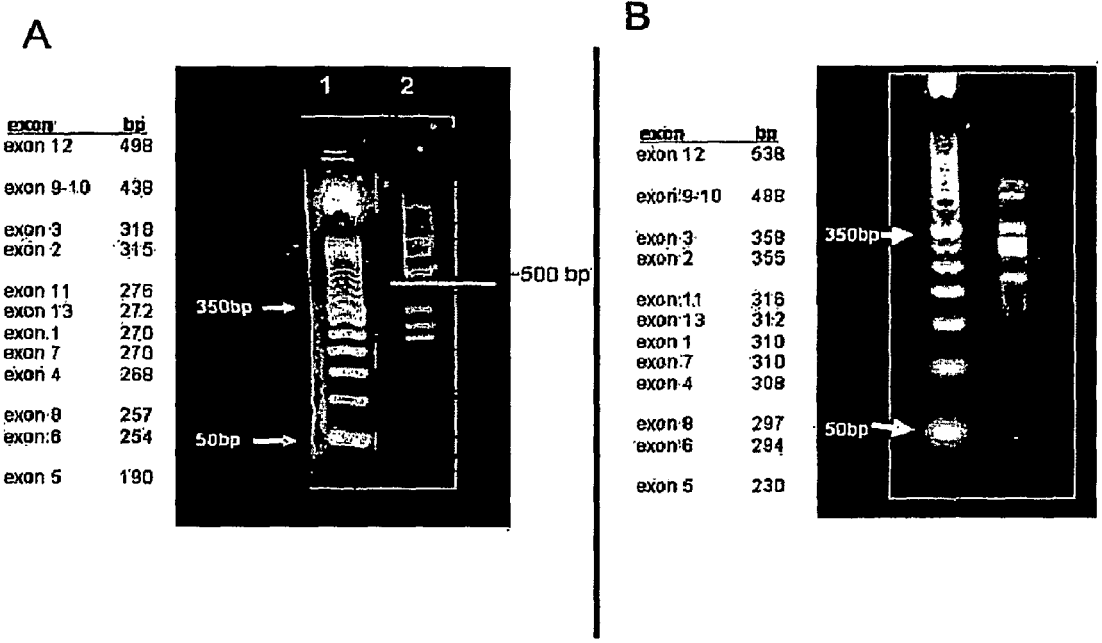
FIG. 6A shows an agarose gel of amplicons generated after 40 cycles of multiplex PCR. Numerous non-target amplicons can be seen (e.g., those greater than 500 bp.
FIG. 6B shows an agarose gel of the amplicons generated in a multiplex PCR reaction using the same primers as in 6A in which a circularization and selection of the present invention is employed. Target amplicons have been selected while non-target amplicons have not.

The products of this multiplex PCR reaction were analyzed by agarose gel electrophoresis (1.5% agarose gel stained with SYBR® green I) and run with a 50 bp latter (FIG. 6A). The expected sizes of the target amplicons are listed on the left. As can be seen from the gel, numerous amplicons were generated that do not correspond to the expected sizes for target amplicons (e.g., no target amplicons should be larger than 500 base pairs, yet a number of amplicons are much larger). Therefore, this multiplex PCR reaction generated many non-target amplicons.

Selection of Target Amplicons by Circularization

Multiplex PCR was performed using the same regents and primers as above except that the reaction was subjected to 8 cycles in step 2 rather than 40. After the reaction, excess primers were removed by three rounds of Centricon YM-100 filtration (500 µL TE buffer was used for each round). Circularization was performed as shown in FIG. 5 employing 12 specific circularization template oligonucleotides. Sequences of the circularization template oligonucleotide, including the intervening domain and the hybridized complement, are shown in Table 2.

TABLE 2

Circularization templates for EGFR primer pairs listed in Table 1 having a intervening domain (in bold and underlined)**.

| Primer Pair # | 5' to 3' Sequence [U = deoxyuridine] | SEQ ID NO: |
|---|---|---|
| 1 | GCC CGU CCU UUC CUG UUU GCA AUG GAA CUA AGG GCA GGU GGG UAC UUG UGU UCA ACG CAU CCU GCA UGG GAU GGU G | 25 |
| 2 | GGG CAG AAU UCC ACU UGA AGG CAA UGG AAC UAA GGG CAG GUG GGU ACU UGU GUU CAA CGC ACC UGG ACC UUG AGG GAU UG | 26 |
| 3 | CAG ACA GCA GUU CCG AUG GGC AAU GGA ACU AAG GGC AGG UGG GUA CUU GUG UUC AAC GCC CCU GGA CCC AUU UUA GAC C | 27 |
| 4 | GGG GAC AGC UCU ACA GCA CUG CAA UGG AAC UAA GGG CAG GUG GGU ACU UGU GUU CAA CGC AGC ACA UGC AUC CUU CAU GG | 28 |
| 5 | CCC CUC UCU UCC UUC ACU UGG CAA UGG AAC UAA GGG CAG GUG GGU ACU UGU GUU CAA CGC GAA AGG GCG UCA UCA GUU UC | 29 |
| 6 | CCC ACA CCA GGA CAG AAG ACG CAA UGG AAC UAA GGG CAG GUG GGU ACU UGU GUU CAA CGC CCC UGG GAA AUG AUC CUA CC | 30 |
| 7 | CUU GUC CCG CUC UGU CUC CUG CAA UGG AAC UAA GGG CAG GUG GGU ACU UGU GUU CAA CGC CGC UUC CUC CGU GUG UG | 31 |
| 8 | CUG CUG AGG CUG GGC UCG CAA UGG AAC UAA GGG CAG GUG GGU ACU UGU GUU CAA CGC CUC AAG AGG ACC UGG ACC G | 32 |
| 9-10 | GAG AGA GAA CUU UUC GAC AUA UUU CCG CAA UGG AAC UAA GGG CAG GUG GGU ACU UGU GUU CAA CGC GGA UCC CUA GCU AUU CUU AAU CCA AC | 33 |
| 11 | GCU AAG AUA GGG CAC AGA GCU CGC AAU GGA ACU AAG GGC AGG UGG GUA CUU GUG UUC AAC GCC AGA GUC CCU GAG AGU CUA GAG UAA UG | 34 |
| 12 | CUG UGA AAU UAC CAU GUG AAU UCC GCA AUG GAA CUA AGG GCA GGU GGG UAC UUG UGU UCA ACG CCU CCC ACA GCA UGA CCU ACC | 35 |
| 13 | GGC UCC AGG UUG UUG UUA UAG CGC AAU GGA ACU AAG GGC AGG UGG GUA CUU GUG UUC AAC GCA AGG UGC CGU CUC CUC C | 36 |

**A 5' phosphorylated oligo complementary to the intervening domain above and having central UU nucleotides was included in circularization reaction. The sequence is as follows: [Phos] GCG TTG AAC ACA AGT ACC CAU UCC TGC CTT AGT TCA T TGC (SEQ ID NO: 37).

Formation of the circularization complex and ligation of the target amplicon were accomplished by combining 10 nM of each of the twelve circularization templates and 400 nM of the oligo complementary to the intervening domain in a sample of 1× ampligase buffer. To this sample, 5 Units ampligase (Epicentre) and 5 µL of the multiplex PCR product were added. This mixture was incubated at 95° C. for 5 min, 75° C. for 10 min, 70° C. for 10 min, 65° C. for 30 min, 60° C. for 10 min, and 55° C. for 10 min. To enrich for the circular DNA, these reactions were then treated with a combination of exonuclease I and III in exo I buffer (New England Biolabs) in a volume of 50 µL (with 15 uL of the ligation reaction) for 1 hour at 37° C. then heat inactivated at 95° C. for 10 min.

In order to enable the selective degradation of circularization template oligonucleotides, each contains deoxyuridine residues instead of the standard deoxythymidine, which makes them sensitive to Uracil-N-glycosylase. Also, the oligo complementary to the intervening domain contains two deoxyuridine residues centrally located, which allows Uracil-N-glycosylase to open the circular structure to ease the following PCR amplification (see Table 2). Two µL of the exonuclease reaction above was treated with 2 µL Uracil-N-glycosylase enzyme mix in 1×USER buffer (10 µL total volume) and incubated 60 min at 37° C.

Amplification of Circularized Pool

After Uracil-N-glycosylase treatment, the entire pool of target amplicons was amplified with a common primer pair which is specific for the universal amplification sequence (see Table 3).

strongest staining band resolves into two bands when the intensity of the UV light source is lower).

Control of Uniformity

For many analytical applications the evenness of concentration of all the included DNA targets after amplification is important. The selected PCR products above were analyzed by quantitative real-time PCR (qPCR) using specific internal primers for each exon (see Table 4).

TABLE 4

Primers for real-time quantitative PCR for EGFR Exons amplified using common primer pairs shown in Table 3 (5' to 3').

| Exon | Forward | SEQ ID NO: | Reverse | SEQ ID NO: |
|---|---|---|---|---|
| 2 | GGA GGC TGA GAA AAT GAT CTT CA | 40 | CCA AGG CAC GAG TAA CAA GCT | 41 |
| 3 | CCC AGC CTC TCA CCC TGT AA | 42 | GAT GCA AAT AAA ACC GGA CTG AA | 43 |
| 4 | TGT AGA GCT GTC CCC CAT AGG A | 44 | CAC CTG GGC AGC TGT AAG TGT | 45 |
| 5 | TTT TAC ATT TCA GGC CAA AAG | 46 | GGC TGT TCA CTG ACT TAC GTT TC | 47 |
| 6 | AGC AGT CAC TGG GGG ACT T | 48 | CTC ACA GGG AAC CTT TGC TC | 49 |
| 7 | AGG TGG CAC CAA AGC TGT ATT T | 50 | GAG ACG AAG CCA CGT GCA A | 51 |
| 8 | GGG CCG ACA GCT ATG AGA TG | 52 | GGC CCT TCG CAC TTC TTA CA | 53 |
| 9-10 | TGT GGA GAT CGC CAC TGA TG | 54 | CTC ACT CTC CAT AAA TGC TAC GAA TAT T | 55 |
| 11 | CCA TGC CTT TGA GAA CCT AGA AA | 56 | GCT GTG GTC AAC TTA CTG TTG CTT | 57 |
| 12 | CCA AAA TTA TAA GCA ACA GAG GTG AA | 58 | GAC CCA TTA GAA CCA ACT CCA TAA A | 59 |

Figure 7:
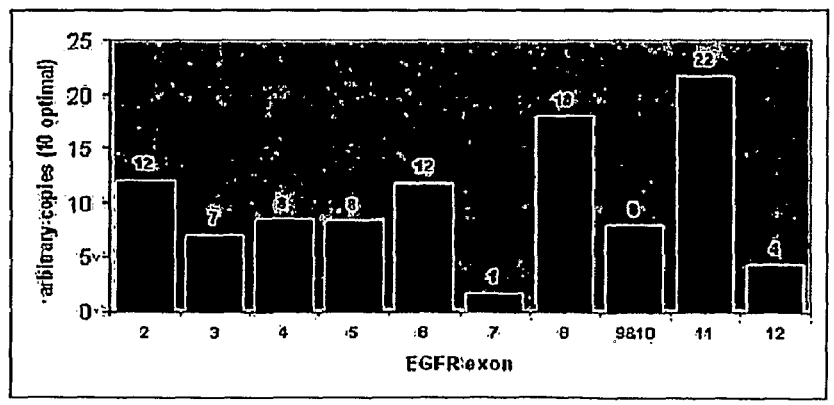
FIG. 7 shows the result of quantitative PCR assay for the EGFR exons that were amplified and selected as in FIG. 6B. Numbers indicate copy number in the sample (estimated from an average abundance of 10 amplicons).

Each qPCR was performed with a 2×SYBR® green master mix from Bio-Rad, 200 nM of each primer, and run on an ABI 7900. FIG. 7 displays normalized data where the optimal value for each exon is 10 copies.

Example 2

Oligonucleotides

All probes and primers synthesized at the Stanford Genome Technology Center. PCR primers were pooled and phosphorylated by optikinase (USB) according to manufacturer's protocol.

Target Amplicon Selection

First multiplex PCR was run in 50 µL with all primers at 100 nM concentration using 10 units Pfu polymerase in 1×Pfu buffer (Stratagene), 200 µM each dNTP and human genomic DNA. Temperature cycling program was: 1) 95° C., 5 min; 2) 8 cycles of 95° C., 30 sec; 55° C. 60 sec; 72° C. 8 min; and 3) 72° C. 10 min. Excess primers after PCR were removed by filtration on centricon YM-100 with three washes of 500 µL TE buffer prior to ligation. Amplicon circularization by ligation on 100 pM of each circularization template oligonucleotide and 52 nM of the complementary universal amplification sequence oligo was performed in 1× ampligase buffer (Epicentre), 5 Units ampligase, at 95° C. for 5 minutes, then 75° C. 10 min, 70° C. 10 min, 65° C. 30 min, 60° C. 10 min, 55° C. 10 min. To enrich for the circular DNA and

TABLE 3

Common primer pairs for amplifying EGFR templates circularized using the circularization templates in Table 2 (5' to 3').

Forward CCT GCC CTT AGT TCC ATT GC (SEQ ID NO: 38)
Reverse TGG GTA CTT GTG TTC AAC GC (SEQ ID NO: 39)

The protocol was the same as the PCR reaction above except that 200 nM of each primer was used. The products of the reaction were run on a 2% agarose gel stained with SYBR®green I (FIG. 6B). As can be seen on the gel, all the expected amplification product sizes have appeared with minimal or no non-target amplicon contamination. (The remove excess circularization template oligos (which contained deoxyuridine residues), 15 µL of the ligation was treated in exonuclease buffer (Epicenter) with 24 units exonuclease 1 and 2 µL uracil DNA excision mix (Epicenter) in 50 µL for 1 hour at 37° C. then heated to 95° C. for 10 minutes. Finally all amplicons were amplified by PCR in a 25 µL reaction using a universal primer pair at 200 nM concentration with 5 Units platinum Taq DNA polymerase (Invitrogen), 3 mM MgCl, and 200 µM of each dNTP.

Quantitative PCR of Amplicons

PCR primers were designed for individual exons of the EGFR gene and used to quantitative the relative abundance of each exon in 10 µL reactions with BioRad SYBR®Green master mix on an ABI 7900 instrument.

Results

Coding sequence specific PCR primer pairs were designed using the ExonPrimer online software for 10 cancer genes. The resulting 170 primer pairs were synthesized, pooled into one tube, and enzymatically phosphorylated. A multiplexed PCR was then run for 8 cycles using Pfu polymerase which generates blunt end PCR products suitable for ligation. Excess primers were then removed using filtration. A pool of circularization template oligos, each specific for one target amplicon, along with an oligo complementary to the universal amplification sequence then guided a circularization reaction of DNA targets with matched primer pair ends. By adding DNA ligase to the circularization reaction, closed circular molecules were formed that all contained the universal amplification sequence complement. The circularization reaction was then followed by an exonuclease treatment to degrade the remaining linear amplicons. Simultaneously, the uracil containing circularization template oligos were degraded by a combination of uracil-N-glycosylase and an apurinic endonuclease. The circularized sequences were finally PCR amplified using a universal primer pair specific for the universal amplification sequence.

Figure 8:
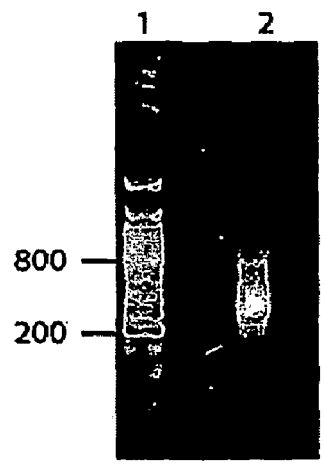
FIG. 8 shows an agarose gel of amplicons resulting from a multiplex PCR employing 170 primer pairs after circularization and selection using a method of the present invention. The resultant amplicons fall within the size range expected (between 200 and 800 bp).

The specificity of this target amplicon enrichment process was assessed using a 1.5% agarose gel stained with SYBR®green (FIG. 8). The gel analysis shows a smear of product with the expected size range for the 170 amplicons (i.e., 200-800 bp), indicating high specificity of the corrector-PCR method.

Figure 9:
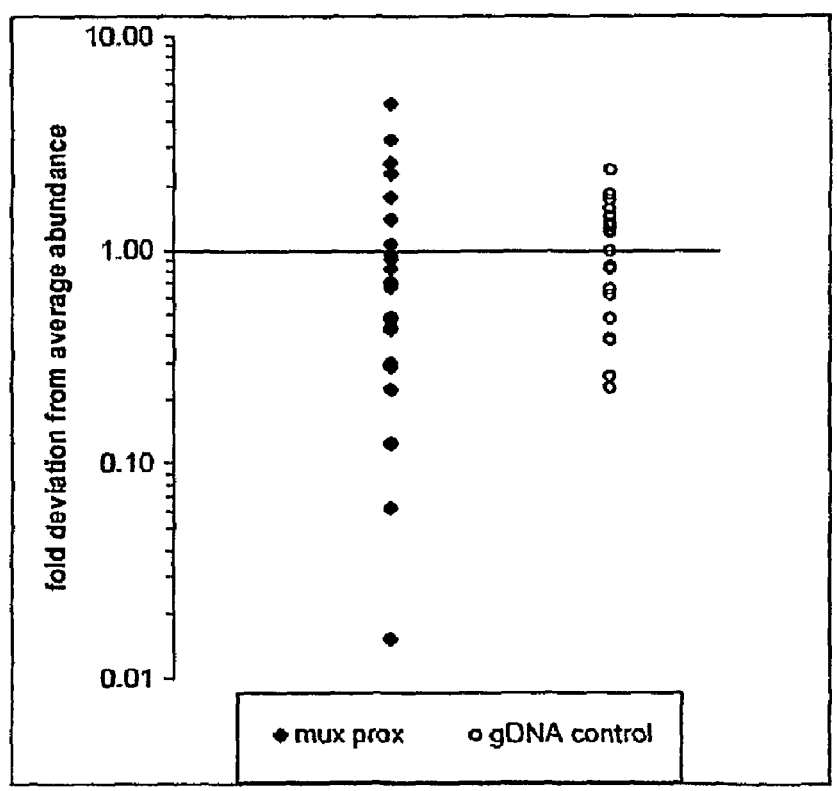
FIG. 9 shows the result of quantitative PCR reaction for 25 of the 170 target amplicons amplified in FIG. 8. Each of the 25 targets from the whole pool of 170 Was individually analyzed in a real-time PCR. As a control of the quantitative PCR variation, the same set of primer-pairs was used for amplifying and analyzing unprocessed genomic DNA. Relative fold deviation of amplified DNA (left) and non-amplified DNA (right) are shown.

To determine whether the target sequences of interest are efficiently amplified, we analyzed 25 specific target amplicons using quantitative PCR. As shown in FIG. 9, all of the 25 amplicons were present in the selected sample (shown on the left side, black diamonds) and are present within a 30-fold concentration range around the overall average abundance. Moreover, 76% of the targets are within 4-fold of the average. Quantitative PCR results using non-amplified genomic DNA and the same 25 primer pairs are shown on the right (open circles).

The target amplicon selection process described above could be simplified or modified in many ways. For example, removal of the excess multiplex PCR primers could be done by using a single stranded exonuclease or vacuum manifold as apposed to the centrifugation method used above. Further, the final universal primer pair could be made exonuclease resistant to enable a simultaneous removal of non-target amplicons (with exonuclease) and second PCR reaction, eliminating one step and reducing hands on time.

Example 3

Single Reaction Tube

This example provides a method for performing the entire reaction in one tube with sequential additions of reagents.

A multiplex PCR is performed as described in Example 2 except that it is performed in a 10 µL volume. After completion, the primers are degraded by adding exonuclease I and the dNTPs are inactivated by adding apyrase (a phosphatase may be used instead). After incubation, the exonuclease and apyrase are inactivated by heating (85° C. for 15-30 minutes).

Circularization template oligonucleotide(s) are added and the volume is adjusted to approximately 15 µL. Hybridization and ligation is performed as described in Example 2 (using ampligase and specific incubation conditions). Removal of the linear nucleic acids by exonuclease I digestion is performed as described above. A final PCR reaction is then performed as described above in a final volume of 50 µl using universal primer pairs.

This one-tube example enables automated high throughput analyses by removing the need for sample manipulation between steps of the low background amplification reaction of the invention.

Example 4

This Example provides a method for single tube multiplex amplification sequences from multiple genes. In this example, the genes of interest are the following human cancer-related genes: v-akt murine thymoma viral oncogene homolog 1 (AKT-1); v-akt murine thymoma viral oncogene homolog 2 (AKT-2); adenomatosis polyposis coli (AFC); epidermal growth factor receptor (EGFR); FK506 binding protein 12-rapamycin associated protein 1 (FRAP); v-Ki-ras2 Kirsten rat sarcoma viral oncogene homolog (KRas); MAP/microtubule affinity-regulating kinase 3 (MARK3); SMAD, mothers against DPP homolog 4 (SMAD4); transforming growth factor, beta receptor II (TGF-beta R2); and tumor protein p53 (TP53).

Materials and Methods

Oligonucleotide Probes and Target Amplicons

All oligonucleotides were synthesized at the Stanford Genome Technology Center (see FIG. 12 for primer sequences and circularization template oligos used). The thymidines were substituted with uracil bases in the circularization template oligonucleotides (also called Collector probes) for degradation purposes by uracil-DNA glycosylase. However, this enzymatic procedure was later found not to be necessary and removed from the protocol

TABLE 5

Analysis of failed amplifications.

|  | Failures | Total | % Success | Fraction |
|---|---|---|---|---|
| Targeted amplicons |  | 170 |  |  |
| Human design error | 1 | 169 |  |  |
| No collector probe negative control | 2 | 167 |  |  |
| Failed at Mux-PCR | 5 | 162 | 97% | 162/167 |
| Failed at ligation | 3 | 159 | 95% | 159/167 |
| Failed at final amplification | 5 | 154 | 92% | 154/167 |
| Unknown failures (no qPCR) 2 with 75% GC | 4 | 150 | 90% | 150/167 |

One primer pair was incorrectly designed through human error and two target sequences lacked Collector probes as a negative control leaving a total of 167 amplicons with a chance of successful amplification. Quantitative PCR revealed at what stage the Gene-Collector protocol failed. The failure reason for the final four amplicons still remains unknown as no successful quantitative PCR primers could be designed.

Multiplex Amplification Protocol (Gene-Collector Protocol)

First, multiplex PCR was run in 50 µl with all 340 primers (170 pairs) at 100 nM concentration each using 10 units pfu polymerase in 1×pfu buffer (Stratagene), 200 µM each dNTP and 200 ng human genomic DNA, at 95° C. for 5 min–[(95°

C. for 30 s; 55° C. for 2 min; 72° C. for 8 min)×8] followed by 72° C. for 10 min. Excess primers were removed by the addition of exonuclease I and incubated for 30 min at 30° C., followed by removal of enzymes by a Qiagen PCR purification column. Amplicon circularization by ligation was performed on 20 nM of each circularization template oligonucleotide (or collector probe) in 1×Ampligase buffer (Epicentre), 5 units Ampligase, 5 units OptiKinase (USB), 1 mM ATP, 1 mM DTT at 37° C. for 30 min–[(95° C. for 30 s; 65° C. for 2 min; 55° C. for 1 min, 60° C. for 5 min)×10] in 50 µl. A combination of exonuclease I, exonuclease T7 gene 6 and λ exonuclease reduced the amount of linear DNA during 45 min at 37° C. and then stopped when heated for 20 min at 80° C. The circular DNA was concentrated by a second Qiagen PCR purification column eluted in the supplied elution buffer and set to evaporate for 45 min at 65° C. One microliter of the 10-fold concentrated circles were added to a 10 µl TempliPhi reaction (GE) supplemented with 10% DMSO and run at 30° C. for 16 h, then inactivated at 65° C. for 10 min.

Resequencing by Hybridization

A 50-kb high-density DNA array was designed by Affymetrix to match the 10-gene reference sequences. The collector amplified product was purified in a PCR purification column (Qiagen). One hundred and fifty nanograms of purified product was fragmented, labeled and finally hybridized according to the protocol provided by Affymetrix (GeneChip Custom-Seq Resequencing Array Protocol). The array was washed and stained using the Affymetrix GeneChip Fluidics Station 450 and scanned using GeneChip Scanner 3000 according to the protocol. The scanned probe array image was analyzed using Affymetrix GeneChip Sequence Analysis Software.

Quantitative PCR of Amplicons

Ten microliter reactions containing 400 nM of qPCR primers specific for the individual amplicons with 2 µl of the TempliPhi reaction diluted 1000-fold in TE buffer were performed to assay their relative abundance. Bio-Rad Sybr Green master mix (1×) was used on an ABI 7900 instrument (see Table 7 for primers).

Results

Figure 10:
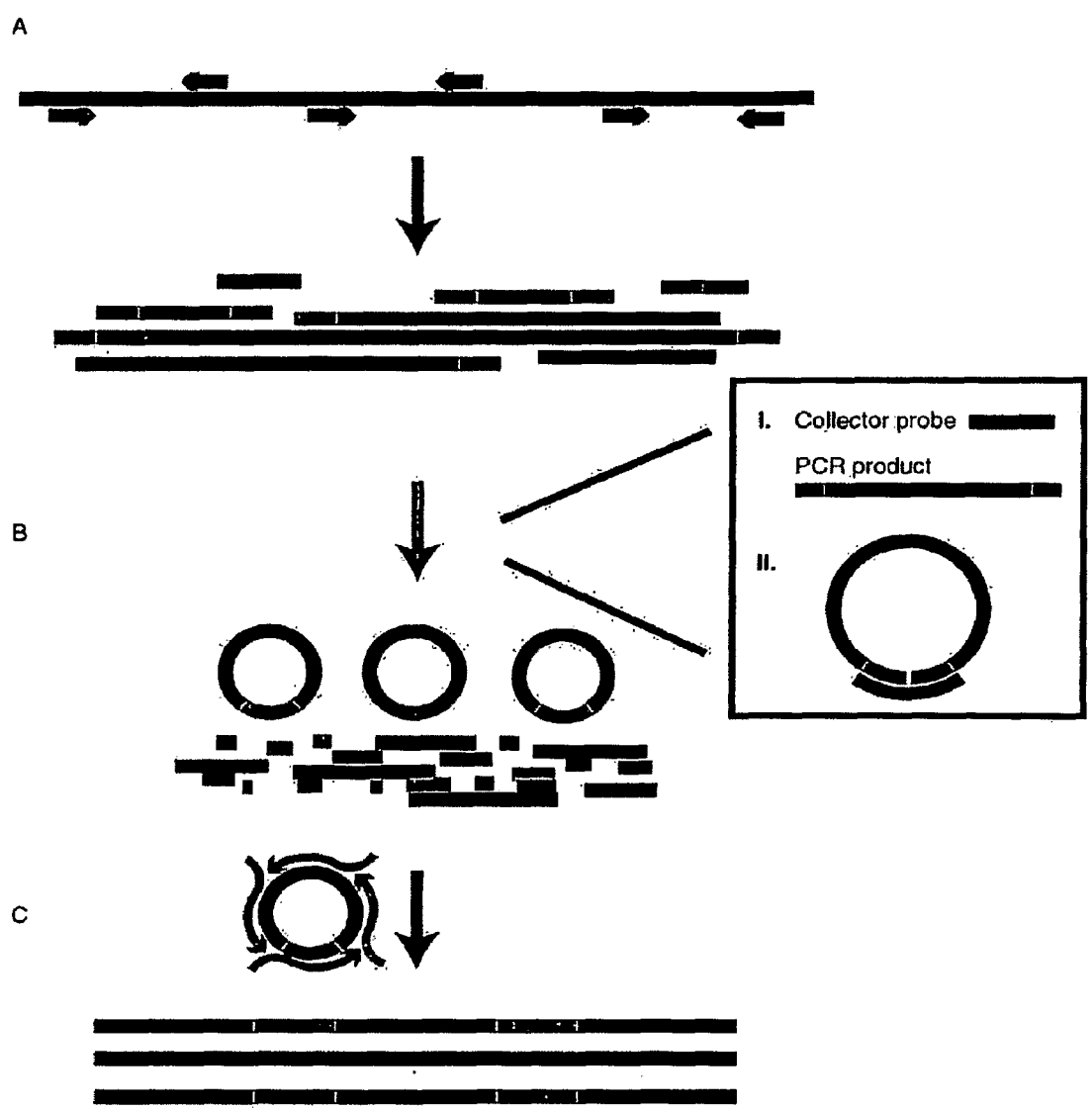
FIG. 10 is a diagrammatic representation of the multiplex amplification protocol of Example 4. (A) A multiplex PCR is carried out using target specific primer pairs, generating both correct and incorrect products. For clarity, only three of the 170 primer pairs are shown. (B) Guided by the collector probe, targets that contain matched primer pairs are circularized, leaving non-cognate products linear and thus susceptible to exonuclease degradation. In detail, (I) a collector probe contains complementary sequences to a cognate primer pair (shaded regions). (II) The collector probe and the DNA ligase enable circularization of correctly amplified targets. (C) A universal amplification is then carried out using a randomly primed rolling circle amplification, generating a final product of concatemers of correct target sequences.

Coding-sequence-specific PCR primer pairs were designed using ExonPrimer [see http(colon)//ihg(dot)gsf(dot)de/ihg/ExonPrimer(dot)html] for 10 cancer-related genes (see FIG. 12). The resulting 170 primer pairs were synthesized and pooled into one tube. A multiplexed PCR was then run for eight cycles using pfu polymerase which generates blunt-end PCR products suitable for circularization by ligation: Excess primers were then removed using a single strand-specific exonuclease followed by a Qiagen PCR product purification column. A pool of Collector probes, each specific to one correct amplicon (shown in FIG. 12) then guided a circularization reaction of matched PCR primer pair ends and closed circles were formed by a DNA ligase enzyme. The ligation reaction also involved a pre-step at 37° C. for phosphorylation of 5'-ends by a kinase enzyme prior to ligation. Circularization was then followed by the addition of an exonuclease cocktail to degrade linear DNA such as amplification artifacts, genomic DNA and excess Collector probes. The circularized sequences were finally amplified using hyper-branched rolling circle amplification with random hexamers and phi-29 polymerase (TempliPhi). An outline of the above described multiplex amplification procedure (the Gene-Collector procedure) is displayed in shown in FIG. 10.

The success rate of the amplification was assessed by hybridizing the final product on an Affymetrix custom-designed resequencing array containing probes scanning the coding sequence of these 10 genes with four variant probes for each nucleotide position, A, T, G and C. The array revealed that 90% of the target sequences had been successfully amplified as assessed by providing accurately read sequence for at least 30% of the nucleotides in each individual amplicon located in continuous stretches of sequence.

Figure 11:
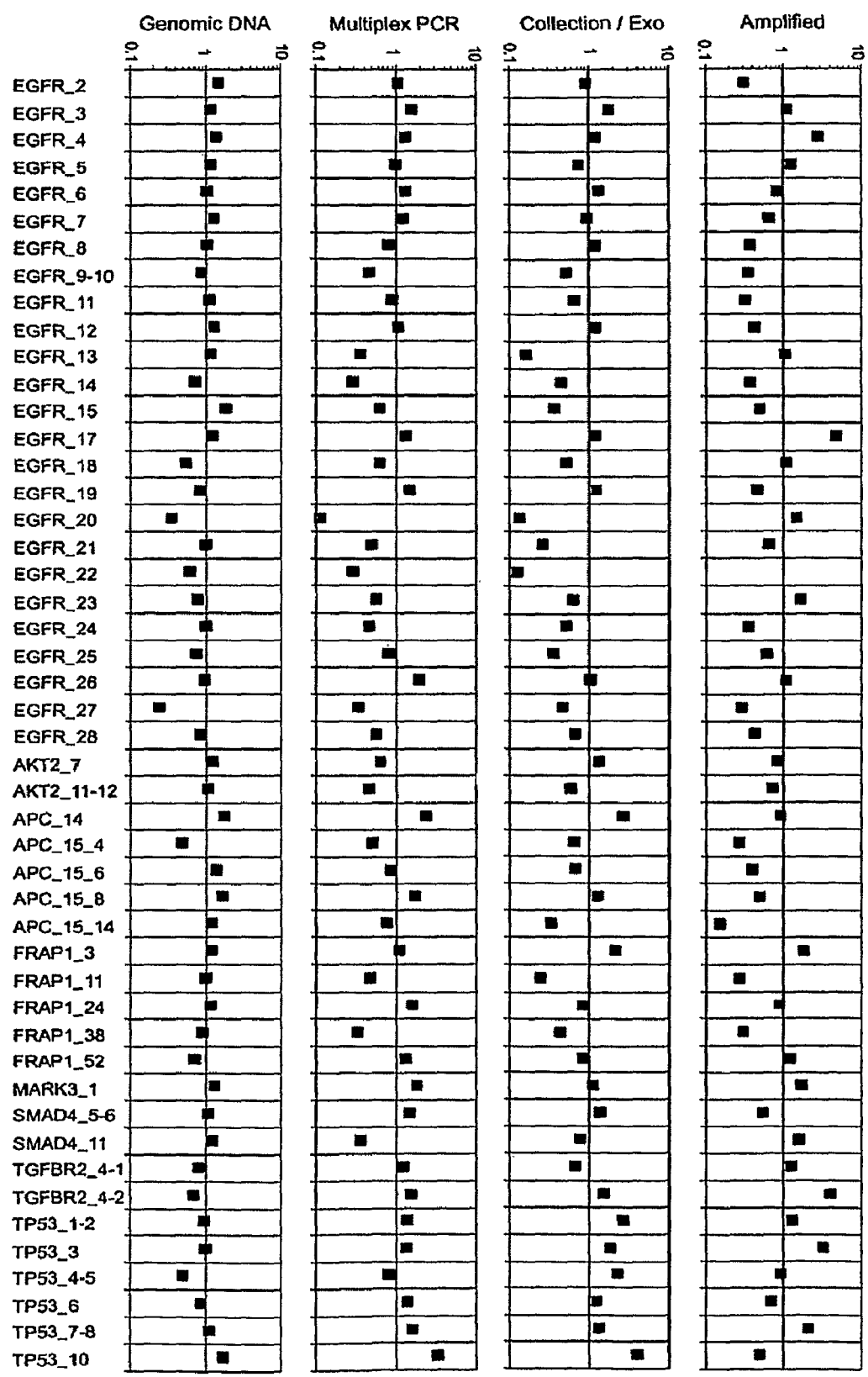
FIG. 11 demonstrates the evenness measurements of at various stages of the multiplex amplification process assessed by quantitative PCR. A subset of 48 targets, all successfully amplified according to the resequencing array, was chosen to represent the overall variation in amplification efficiency. The starting material of human genomic DNA, assumed to be perfectly uniform, is compared to the evenness after the multiplex PCR, the ligation and exonuclease treatment and finally the rolling circle amplified material. The Y-axis represents a log-scale with deviations from 1 being relative differences from the average abundance. No compensation for differences in real-time PCR efficiency between reactions was used. However, the genomic DNA starting material represents a measure of this variation and the general imprecision of the real-time PCRs. Here, 96% of the final amplicons analyzed was no less than one-fourth of the average abundance.

The initial multiplex PCR is conducted under very non-stringent conditions in order to give all target sequences the best chance of efficient amplification. This would normally generate many amplification artifkts but these are efficiently removed by circularization and exonuclease degradation. To ensure uniformity of the multiplex-PCR, extension times were long (i.e., 8 min.), with primer hybridizations conducted at 55° C. for 2 min. Each stage of the reaction was analyzed for evenness by quantitative PCR (see FIG. 11). As shown in FIG. 11, the multiplex Gene-Collector protocol amplifies target sequences in a substantially uniform manner (i.e., the Gene-Collector protocol does not lead to significant over- or under-sampling of the target amplicons).

It is noted here that a number of primer pairs that did not work in individual PCRs under standard conditions (e.g., as analyzed by agarose gel) did produce the correct product with the Gene-Collector procedure (data not shown).

The final amplification by TempliPhi was supplemented with a 10% final DMSO concentration to reduce potential skewing effects of varied amplicon GC content. The average abundance of each final product was estimated to be at 10 nM in a 10 µl reaction volume with 96% of all amplicons having no less than one-fourth of the average abundance.

In order to measure the levels of false amplification products generated by the Gene-Collector protocol, the final product was cloned and sequenced. The Tempi'Phi reaction produces concatemeric products of 10 kb each, which were fragmented by sonication, gel purified and cloned into a sequencing vector. When 96 colonies were picked and Sanger sequenced, 93 reads showed that 58% of the reads were of expected products (see Table 6). As cloning selects the sequence representation randomly, it provides an additional measure of frequency distribution. Most amplicons appeared only once showing even representation. Nine amplicons appeared twice and two of the targets three times. No non-specific products appeared more than once. The fraction of paired matched primers found among the non-specific products was much lower than for the specific ones. As can be seen in Table 6, few non-specific products were formed by two matched primer pairs amplifying a non-target sequence. This type of false product would still become circularized by the Collector probe but are not the main source of errors. As expected from cloned rolling-circle-amplified material, many sequencing reactions produced concatemeric reads of repeated elements. Interestingly, this provided redundant sequencing within one and the same read with up to 3-fold coverage.

TABLE 6

Analysis of amplification product by cloning and sequencing.

| | Reads | % of total | Fraction |
|---|---|---|---|
| Total sequence reads | 93 | | |
| Correct products | 54 | 58% | 54/93 |
| two matched primers | 52 | | |
| one primer | 52 | | |
| Non-specific products | 39 | 42% | 39/93 |
| two matched primers | 4 | | |

TABLE 6-continued

Analysis of amplification product by cloning and sequencing.

| | Reads | % of total | Fraction |
|---|---|---|---|
| one primer | 8 | | |
| two non matched primers | 2 | | |
| not found in human genome | 1 | | |

From the 93 total reads produced, 58% of these were of the expected products. Primer sequences were only rarely found within the non-specific products either as single primers, non-matched pairs or as matched pairs suggesting that the TempliPhi reaction produced the majority of the artifacts or that they were simply caused by remaining genomic DNA We have amplified all the coding sequences located in 10 cancer genes using a multiplexed amplification procedure (termed Gene-Collector). Resequencing of large numbers of cancer-related genes has recently shown to provide important biological insights into the disease (see, e.g., Sjoblom et al. (2006) The consensus coding sequences of human breast and colorectal cancers Science, 314, 268-274). Even with extensive optimization, standard multiplex PCR is not a feasible approach to large-scale genetic studies as the failure rate is too high due to the many false amplicons out competing the'correct ones for the amplification reagents. However, even though these false amplicons do result, the correct products are also present and at uniform abundance early in the amplification. The present invention reduces the presence of false products enabling further amplification of the correct ones.

The presented initial multiplex PCR had very relaxed conditions in order to give all primer pairs the ability to hybridize through the use of low hybridization temperature and long duration. Polymerization of all templates was assured by a long extension time and an ample amount of DNA polymerase. This condition was suitable for all amplicons as the Collector procedure removes artifacts by exonuclease degradation. Primer-dimer artifacts, which are a major problem in traditional multiplexed PCR, are of little concern for Gene-Collector as the circularization process is impossible of such short DNA strands due to the lower limit size constraints of partially double stranded circular DNA (Baneret al. (1998) Signal amplification of padlock probes by rolling circle replication Nucleic Acids Res, 26, 5073-5078). As shown above, the relative abundance of products from the rolling circle reaction was very even.

Alternatively, one may use PCR in the final amplification of the circularized amplicons, which then gives distinct bands on standard agarose gel (see, e.g., FIG. 6B). Certain embodiments of the Gene-Collector protocol employ a general primer pair motif within the Collector probe and as such can generate a purer product than the randomly primed rolling circle amplification. This could, for example, be suitable for rapid multiplex pathogen detection using electrophoretic separation.

It is noted that target sequences could be arrayed if the circularization is performed on immobilized Collector probes.

The present invention finds use in a wide range of amplification-based applications, particularly in combination with highly parallel DNA analysis platforms. One class of parallel DNA analysis is large-scale sequencing and resequencing platforms [see, e.g., Shendure et al. (2004) Advanced sequencing technologies: methods and goals Nat. Rev, 5, 335-344], such as sequencing by hybridization, sequencing by ligation or sequencing by synthesis systems [see, e.g., Ghee et al. (1996) Accessing genetic information with high-density DNA arrays Science, 274, 610-614; Patil et al. (2001) Blocks of limited haplotype diversity revealed by high-resolution scanning of human chromosome 21 Science, 294, 1719-1723; Margulies et al. (2005) Genome sequencing in microfabricated high-density picolitre reactors Nature, 437, 376-380; and Shendure et al. (2005) Accurate multiplex polony sequencing of an evolved bacterial genome Science, 309:1728-32]. The multiplex amplification technology disclosed herein also finds use in combination with PCR-intense genotyping methods, like mini-sequencing [see, e.g., Syvanen et al. (1990) A primer-guided nucleotide incorporation assay in the genotyping of apolipoprotein E Genomics, 8, 684-692; and Pastinen et al. (2000) A system for specific, high-throughput genotyping by allele-specific primer extension on microarrays Genome Res, 10, 1031-1042] and primer extension-based methods in concert with mass spectrometry analysis [see, e.g., Tost, J and Gut, I G. (2002) Genotyping single nucleotide polymorphisms by mass spectrometry Mass Spectrom. Rev, 21, 388-418], as well as high throughput pathogen detection. Gene-Collector can be combined with genetic variation detection techniques that require many single PCRs [see, e.g., Faham et al. (2001) Mismatch repair detection (MRD): high-throughput scanning for DNA variations Hum. Mol. Genet, 10, 1657-1664; and Fakhrai-Rad et al. (2004) SNP discovery in pooled samples with mismatch repair detection Genome Res, 14, 1404-1412] to increase assay throughput.

The present invention also enables analysis of small and precious sample materials, reduces enzyme consumption and offers higher throughput of DNA amplification.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method of selectively amplifying two or more target nucleic acids of a nucleic acid sample, said method comprising: (a) contacting said nucleic acid sample with primer pairs specific for two or more target nucleic acid sequences of interest to produce a first reaction mixture; (b) subjecting said first reaction mixture to template-dependent primer extension reaction conditions to produce an amplified composition comprising target amplicons; (c) circularizing said target amplicons in said amplified composition; wherein said circularizing comprises:
   (i) contacting said amplified composition under hybridization conditions with circularization template oligonucleotides specific for each of said target amplicons to produce circularization complexes; and
   (ii) contacting said circularization complexes with a circularizing agent to circularize said target amplicon; and (d) selecting for said circularized target amplicons in said amplified composition.

2. The method according to claim 1, wherein said template dependent primer extension reaction conditions are polymerase chain reaction conditions (PCR).

3. The method according to claim 1, wherein said amplified composition further comprises non-target amplicons.

4. The method according to claim 1, wherein each of said circularization template oligonucleotides comprises a first domain and a second domain, wherein said first domain and said second domain comprise sequences complementary to a 5' end sequence and a 3' end sequence of the same strand of its corresponding target amplicon, respectively.

5. The method according to claim 4, wherein each of said circularization template oligonucleotides comprises an intervening domain between said first domain and said second domain.

6. The method according to claim 1, wherein said circularizing agent is a DNA ligase.

7. The method according to claim 1, wherein each of said circularization template oligonucleotides is immobilized on a solid support.

8. The method according to claim 1, wherein said method employs primer pairs specific for 5 or more different target nucleic acid sequences.

9. The method according to claim 1, wherein said selecting step comprises contacting said amplified composition comprising circularized target amplicons to an exonuclease.

10. The method according to claim 1, wherein said selecting step further comprises amplifying said circularized target amplicons.

11. The method according to claim 10, wherein said amplifying is by rolling circle amplification.

12. The method according to claim 10, wherein said amplifying is by PCR.

13. The method according to claim 12, wherein said method further comprises linearizing said circularized target nucleic acids prior to said amplifying.

14. The method according to claim 1, wherein said method produces an amplified composition comprising less than about 50% by weight non target-amplicons.

15. The method according to claim 7, wherein the method comprises removing circularized target amplicons from the solid support.

* * * * *